US011066450B2

(12) United States Patent
Bottomley et al.

(10) Patent No.: US 11,066,450 B2
(45) Date of Patent: Jul. 20, 2021

(54) MODIFIED MENINGOCOCCAL FHBP POLYPEPTIDES

(71) Applicant: GLAXOSMITHKLINE BIOLOGICALS, SA, Rixensart (BE)

(72) Inventors: Matthew Bottomley, Siena (IT); Vega Masignani, Siena (IT)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 15/319,651

(22) PCT Filed: Jul. 16, 2015

(86) PCT No.: PCT/EP2015/066228
§ 371 (c)(1),
(2) Date: Dec. 16, 2016

(87) PCT Pub. No.: WO2016/008960
PCT Pub. Date: Jan. 21, 2016

(65) Prior Publication Data
US 2017/0226161 A1    Aug. 10, 2017

(30) Foreign Application Priority Data

Jul. 17, 2014    (EP) ..................... 14177564

(51) Int. Cl.
    *C07K 14/22*    (2006.01)
    *A61K 39/095*    (2006.01)
    *A61K 39/00*    (2006.01)

(52) U.S. Cl.
    CPC ............ *C07K 14/22* (2013.01); *A61K 39/095* (2013.01); *A61K 2039/575* (2013.01); *C07K 2319/33* (2013.01)

(58) Field of Classification Search
None
See application file for complete search history.

(56) References Cited

U.S. PATENT DOCUMENTS

2017/0008933 A1    1/2017 Bottomley et al.
2018/0214531 A1    8/2018 Biolchi et al.

FOREIGN PATENT DOCUMENTS

| WO | 2004/048404 A2 | 6/2004 |
| WO | 2006/024954 A2 | 3/2006 |
| WO | WO 2006/024954 | 3/2006 |
| WO | 2007/060548 A2 | 5/2007 |
| WO | 2011/110634 A1 | 9/2011 |
| WO | 2011/126863 A1 | 10/2011 |
| WO | 2013/186753 A1 | 12/2013 |
| WO | 2014/030003 A1 | 2/2014 |
| WO | WO 2015/128480 | 9/2015 |

OTHER PUBLICATIONS

Greenspan et al. (Nature Biotechnology 17: 936-937, 1999) (Year: 1999).*
Bowie et al (Science, 1990, 257:1306-1310) (Year: 1990).*
Burgess et al (J. of Cell Bio. 111:2129-2138, 1990) (Year: 1990).*
Lazar et al. (Molecular and Cellular Biology, 1988, 8:1247-1252) (Year: 1988).*
Bork (Genome Research, 2000,10:398-400) (Year: 2000).*
R. Pajon et al: "Design of Meningococcal Factor H Binding Protein Mutant Vaccines That Do Not Bind Human Complement Factor H", Infection and Immunity, vol. 80, No. 8, May 21, 2012 (May 21, 2012), pp. 2667-2677.
Muriel C Schneider et al: "Neisseria meningitidis recruits factor H using protein mimicry of host carbohydrates", Nature, Nature Publishing Group, United Kingdom, vol. 458, No. 7240, Apr. 16, 2009 (Apr. 16, 2009), pp. 890-893.
Beernink Peter T et al: "Impaired immunogenicity of a meningococcal factor H-binding protein vaccine engineered to eliminate factor h binding" Clinical and Vaccine Immunology, American Society for Microbiology, Washington, DC, US, vol. 17, No. 7, Jul. 1, 2010 (Jul. 1, 2010), pp. 1074-1078.
D. M. Granoff et al: "Does Binding of Complement Factor H to the Meningococcal Vaccine Antigen, Factor H Binding Protein, Decrease Protective Serum Antibody Responses?", Clinical and Vaccine Immunology, vol. 20, No. 8, Jun. 5, 2013 (Jun. 5, 2013), pp. 1099-1107.
Rossi Raffaella et al: "Meningococci factor H-binding protein vaccines with decreased binding to human complement factor H have enhanced immunogenicity in human factor H transgenic mice", Vaccine, vol. 31, No. 46, 2013, pp. 5451-5457.
S. Van Der Veen et al: "Nonfunctional Variant 3 Factor H Binding Proteins as Meningococcal Vaccine Candidates", Infection and Immunity, vol . 82, No. 3, Dec. 30, 2013 (Dec. 30, 2013), pp. 1157-1163.
The sequence available as UniProtKB Accession No. L0GGE0, entitled Factor H binding protein, submitted Mar. 6, 2013, available at http://www.uniprot.org/uniprot/L0GGE0.txt?version=1.
The sequence available as UniProtKB Accession No. L0GFA3, entitled Factor H binding protein, submitted Mar. 6, 2013, available at http://www.uniprot.org/uniprot/L0GFA3.txt?version=1.
International Search Report and Written Opinion for Application No. PCT/EP2015/066228 dated Aug. 26, 2015, by the European Patent Office as International Searching Authority, 14 total pages.
Esposito Susanna et al: "A phase I I randomized controlled trial of a multicomponent meningococcal serogroup B vaccine, 4CMenB, in infants (II)", Human Vaccines & Immunotherapeutics July 2014, vol. 10, No. 7, Jul. 11, 2014 (Jul. 11, 2014), pp. 2005-2014.
D. M. Granoff et al: "Does Binding of Complement Factor H to the Meningococcal Vaccine Antigen, Factor H Binding Protein, Decrease Protective Serum Antibody Responses?", Clinical and Vaccine Immunology, vol. 20, No. 8, Jun. 5, 2013, pp. 1099-1107.
Peter T. Beernink et al: "The Effect of Human Factor H on Immunogenicity of Meningococcal Native Outer Membrane Vesicle Vaccines with Over-Expressed Factor H Binding Protein", PLOS Pathogens, vol. 8, No. 5, May 10, 2012, pp. e1002688-e1002688 (9 total pages).

(Continued)

*Primary Examiner* — Robert A Zeman

(57) ABSTRACT

The inventors have identified residues within variant 2 and variant 3 of meningococcal fHbp which can be modified to enhance their properties.

3 Claims, 8 Drawing Sheets

Specification includes a Sequence Listing.

(56) References Cited

OTHER PUBLICATIONS

Koeberling Oliver et al: "Meningococcal outer membrane vesicle vaccines derived from mutant strains engineered to express factor H binding proteins from antigenic variant groups 1 and 2", Clinical and Vaccine Immunology, American Society for Microbiology, Washington, DC, US, vol. 16, No. 2, Feb. 1, 2009, pp. 156-162.
Assessment report of Bexsero (common name "Meningococcal group B Vaccine (rDNA, component, adsorbed)") by the European Medicines Agency (Committee for Medicinal Products for Human Use (CHMP)); Procedure No. EMEA/H/C/002333; dated Nov. 15, 2012, available online at http://www.ema.europa.eu/docs/en GB/document library/EPAR_-_Public_ assessment_report/human/002333/ WC500137883.pdf; retrieved on Dec. 16, 2016; 102 total pages.
Dan M Granoff et al: "Chapter 21 Section: Two: Licensed vaccines— Meningococcal vaccines" in "Vaccines (6th Edition)", Jan. 1, 2013 (Jan. 1, 2013), Elsevier, XP055150061, ISBN: 978-1-45-570090-5; pp. 388-418.
International Search Report and Written Opinion for Application No. PCT/EP2015/066229 dated Jan. 10, 2015, by the European Patent Office as International Searching Authority, 15 total pages.
Intellectual Property Office of Singapore, Written Opinion dated Jan. 26, 2018 for Singapore Appl. No. 11201610945P (based on Int'l Appl. No. PCT/EP2015/066229 filed Jul. 16, 2015); 8 total pages.
Beernink et al., *Rapid Genetic Grouping of Factor H-Binding Protein (Genome-Derived Neisserial Antigen 1870), a Promising Group B Meningococcal Vaccine Candidate*, 2006 Clinical and Vaccine Immunology 13(7): 758-763.
Johnson et al., *Design and Evaluation of Meningococcal Vaccines through Structure-Based Modification of Host and Pathogen Molecules* 2012 PLoS Pathogen 8(10):e1002981; 13 total pages.
Van Der Veen et al., *Nonfunctional Variant 3 Factor H Binding Proteins as Meningococcal Vaccine Candidates*, 2014 Infection and Immunity 82(3):1157-1163.
Masignani et al., *Vaccination against Neisseria meningitidis Using Three Variants of the Lipoprotein GNA1870* 2003 J. Exp. Med 197(6):789-799.

\* cited by examiner

SEQUENCE LISTING

<160> NUMBER OF SEQ ID NOS: 60

<210> SEQ ID NO 1
<211> LENGTH: 274
<212> TYPE: PRT
<213> ORGANISM: Neisseria meningitidis

<400> SEQUENCE: 1

```
Met Asn Arg Thr Ala Phe Cys Cys Leu Ser Leu Thr Thr Ala Leu Ile
 1               5                  10                  15

Leu Thr Ala Cys Ser Ser Gly Gly Gly Gly Val Ala Ala Asp Ile Gly
                20                  25                  30

Ala Gly Leu Ala Asp Ala Leu Thr Ala Pro Leu Asp His Lys Asp Lys
            35                  40                  45

Gly Leu Gln Ser Leu Thr Leu Asp Gln Ser Val Arg Lys Asn Glu Lys
        50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Phe
        115                 120                 125

Gln Thr Glu Gln Ile Gln Asp Ser Glu His Ser Gly Lys Met Val Ala
    130                 135                 140

Lys Arg Gln Phe Arg Ile Gly Asp Ile Ala Gly Glu His Thr Ser Phe
145                 150                 155                 160
```

Asp Lys Leu Pro Glu Gly Gly Arg Ala Thr Tyr Arg Gly Thr Ala Phe
            165                 170                 175

Gly Ser Asp Asp Ala Gly Gly Lys Leu Thr Tyr Thr Ile Asp Phe Ala
            180                 185                 190

Ala Lys Gln Gly Asn Gly Lys Ile Glu His Leu Lys Ser Pro Glu Leu
            195                 200                 205

Asn Val Asp Leu Ala Ala Ala Asp Ile Lys Pro Asp Gly Lys Arg His
            210                 215                 220

Ala Val Ile Ser Gly Ser Val Leu Tyr Asn Gln Ala Glu Lys Gly Ser
225                 230                 235                 240

Tyr Ser Leu Gly Ile Phe Gly Gly Lys Ala Gln Glu Val Ala Gly Ser
            245                 250                 255

Ala Glu Val Lys Thr Val Asn Gly Ile Arg His Ile Gly Leu Ala Ala
            260                 265                 270

Lys Gln

<210> SEQ ID NO 2
<211> LENGTH: 273
<212> TYPE: PRT
<213> ORGANISM: Neisseria meningitidis

<400> SEQUENCE: 2

Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
            35                  40                  45

Ser Leu Gln Ser Leu Thr Leu Asp Gln Ser Val Arg Lys Asn Glu Lys
        50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
            115                 120                 125

Gln Ile Glu Lys Ile Asn Asn Pro Asp Lys Ile Asp Ser Leu Ile Asn
        130                 135                 140

Gln Arg Ser Phe Leu Val Ser Gly Leu Gly Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
            195                 200                 205

Val Glu Leu Ala Ala Ala Glu Leu Lys Ala Asp Glu Lys Ser His Ala
            210                 215                 220

Val Ile Leu Gly Asp Thr Arg Tyr Gly Ser Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Gly Glu Lys Val His Glu Ile Gly Ile Ala Gly Lys
            260                 265                 270

Gln

<210> SEQ ID NO 3
<211> LENGTH: 281
<212> TYPE: PRT
<213> ORGANISM: Neisseria meningitidis

<400> SEQUENCE: 3

Met Asn Arg Thr Ala Phe Cys Cys Leu Ser Leu Thr Thr Ala Leu Ile
1               5                   10                  15

Leu Thr Ala Cys Ser Ser Gly Gly Gly Ser Gly Gly Gly Gly Gly Val
            20                  25                  30

Ala Ala Asp Ile Gly Thr Gly Leu Ala Asp Ala Leu Thr Ala Pro Leu
        35                  40                  45

Asp His Lys Asp Lys Gly Leu Lys Ser Leu Thr Leu Glu Asp Ser Ile
    50                  55                  60

Pro Gln Asn Gly Thr Leu Thr Leu Ser Ala Gln Gly Ala Glu Lys Thr
65                  70                  75                  80

Phe Lys Ala Gly Asp Lys Asp Asn Ser Leu Asn Thr Gly Lys Leu Lys
                85                  90                  95

Asn Asp Lys Ile Ser Arg Phe Asp Phe Val Gln Lys Ile Glu Val Asp
            100                 105                 110

Gly Gln Thr Ile Thr Leu Ala Ser Gly Glu Phe Gln Ile Tyr Lys Gln
        115                 120                 125

Asn His Ser Ala Val Val Ala Leu Gln Ile Glu Lys Ile Asn Asn Pro
    130                 135                 140

Asp Lys Thr Asp Ser Leu Ile Asn Gln Arg Ser Phe Leu Val Ser Gly
145                 150                 155                 160

Leu Gly Gly Glu His Thr Ala Phe Asn Gln Leu Pro Gly Gly Lys Ala
                165                 170                 175

Glu Tyr His Gly Lys Ala Phe Ser Ser Asp Pro Asn Gly Arg Leu
            180                 185                 190

His Tyr Ser Ile Asp Phe Thr Lys Lys Gln Gly Tyr Gly Arg Ile Glu
        195                 200                 205

His Leu Lys Thr Leu Glu Gln Asn Val Glu Leu Ala Ala Ala Glu Leu
    210                 215                 220

Lys Ala Asp Glu Lys Ser His Ala Val Ile Leu Gly Asp Thr Arg Tyr
225                 230                 235                 240

Gly Ser Glu Glu Lys Gly Thr Tyr His Leu Ala Leu Phe Gly Asp Arg
                245                 250                 255

Ala Gln Glu Ile Ala Gly Ser Ala Thr Val Lys Ile Gly Glu Lys Val
            260                 265                 270

His Glu Ile Gly Ile Ala Gly Lys Gln
        275                 280

<210> SEQ ID NO 4
<211> LENGTH: 254
<212> TYPE: PRT
<213> ORGANISM: Neisseria meningitidis

<400> SEQUENCE: 4

Cys Ser Ser Gly Gly Gly Gly Val Ala Ala Asp Ile Gly Ala Gly Leu
1               5                   10                  15

```
Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
130                 135                 140

Pro Asp Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
                245                 250

<210> SEQ ID NO 5
<211> LENGTH: 247
<212> TYPE: PRT
<213> ORGANISM: Neisseria meningitidis

<400> SEQUENCE: 5

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Leu Val Ser Gly Leu Gly
        115                 120                 125

Gly Glu His Thr Ala Phe Asn Gln Leu Pro Asp Gly Lys Ala Glu Tyr
    130                 135                 140
```

His Gly Lys Ala Phe Ser Ser Asp Asp Ala Gly Lys Leu Thr Tyr
145                 150                 155                 160

Thr Ile Asp Phe Ala Ala Lys Gln Gly His Gly Lys Ile Glu His Leu
            165                 170                 175

Lys Thr Pro Glu Gln Asn Val Glu Leu Ala Ala Ala Glu Leu Lys Ala
        180                 185                 190

Asp Glu Lys Ser His Ala Val Ile Leu Gly Asp Thr Arg Tyr Gly Ser
    195                 200                 205

Glu Glu Lys Gly Thr Tyr His Leu Ala Leu Phe Gly Asp Arg Ala Gln
210                 215                 220

Glu Ile Ala Gly Ser Ala Thr Val Lys Ile Gly Glu Lys Val His Glu
225                 230                 235                 240

Ile Gly Ile Ala Gly Lys Gln
                245

<210> SEQ ID NO 6
<211> LENGTH: 488
<212> TYPE: PRT
<213> ORGANISM: Neisseria meningitidis

<400> SEQUENCE: 6

Met Phe Lys Arg Ser Val Ile Ala Met Ala Cys Ile Phe Ala Leu Ser
1               5                   10                  15

Ala Cys Gly Gly Gly Gly Gly Ser Pro Asp Val Lys Ser Ala Asp
            20                  25                  30

Thr Leu Ser Lys Pro Ala Ala Pro Val Val Ser Glu Lys Glu Thr Glu
            35                  40                  45

Ala Lys Glu Asp Ala Pro Gln Ala Gly Ser Gln Gly Gln Gly Ala Pro
    50                  55                  60

Ser Ala Gln Gly Ser Gln Asp Met Ala Ala Val Ser Glu Glu Asn Thr
65                  70                  75                  80

Gly Asn Gly Gly Ala Val Thr Ala Asp Asn Pro Lys Asn Glu Asp Glu
                85                  90                  95

Val Ala Gln Asn Asp Met Pro Gln Asn Ala Ala Gly Thr Asp Ser Ser
            100                 105                 110

Thr Pro Asn His Thr Pro Asp Pro Asn Met Leu Ala Gly Asn Met Glu
        115                 120                 125

Asn Gln Ala Thr Asp Ala Gly Glu Ser Ser Gln Pro Ala Asn Gln Pro
    130                 135                 140

Asp Met Ala Asn Ala Ala Asp Gly Met Gln Gly Asp Asp Pro Ser Ala
145                 150                 155                 160

Gly Gly Gln Asn Ala Gly Asn Thr Ala Ala Gln Gly Ala Asn Gln Ala
                165                 170                 175

Gly Asn Asn Gln Ala Ala Gly Ser Ser Asp Pro Ile Pro Ala Ser Asn
            180                 185                 190

Pro Ala Pro Ala Asn Gly Gly Ser Asn Phe Gly Arg Val Asp Leu Ala
        195                 200                 205

Asn Gly Val Leu Ile Asp Gly Pro Ser Gln Asn Ile Thr Leu Thr His
    210                 215                 220

Cys Lys Gly Asp Ser Cys Ser Gly Asn Asn Phe Leu Asp Glu Glu Val
225                 230                 235                 240

Gln Leu Lys Ser Glu Phe Glu Lys Leu Ser Asp Ala Asp Lys Ile Ser
                245                 250                 255

Asn Tyr Lys Lys Asp Gly Lys Asn Asp Lys Phe Val Gly Leu Val Ala

```
                    260                 265                 270
Asp Ser Val Gln Met Lys Gly Ile Asn Gln Tyr Ile Ile Phe Tyr Lys
        275                 280                 285

Pro Lys Pro Thr Ser Phe Ala Arg Phe Arg Arg Ser Ala Arg Ser Arg
        290                 295                 300

Arg Ser Leu Pro Ala Glu Met Pro Leu Ile Pro Val Asn Gln Ala Asp
305                 310                 315                 320

Thr Leu Ile Val Asp Gly Glu Ala Val Ser Leu Thr Gly His Ser Gly
                325                 330                 335

Asn Ile Phe Ala Pro Glu Gly Asn Tyr Arg Tyr Leu Thr Tyr Gly Ala
            340                 345                 350

Glu Lys Leu Pro Gly Gly Ser Tyr Ala Leu Arg Val Gln Gly Glu Pro
        355                 360                 365

Ala Lys Gly Glu Met Leu Ala Gly Ala Val Tyr Asn Gly Glu Val
        370                 375                 380

Leu His Phe His Thr Glu Asn Gly Arg Pro Tyr Pro Thr Arg Gly Arg
385                 390                 395                 400

Phe Ala Ala Lys Val Asp Phe Gly Ser Lys Ser Val Asp Gly Ile Ile
                405                 410                 415

Asp Ser Gly Asp Asp Leu His Met Gly Thr Gln Lys Phe Lys Ala Ala
            420                 425                 430

Ile Asp Gly Asn Gly Phe Lys Gly Thr Trp Thr Glu Asn Gly Ser Gly
        435                 440                 445

Asp Val Ser Gly Lys Phe Tyr Gly Pro Ala Gly Glu Glu Val Ala Gly
        450                 455                 460

Lys Tyr Ser Tyr Arg Pro Thr Asp Ala Glu Lys Gly Gly Phe Gly Val
465                 470                 475                 480

Phe Ala Gly Lys Lys Glu Gln Asp
                485

<210> SEQ ID NO 7
<211> LENGTH: 364
<212> TYPE: PRT
<213> ORGANISM: Neisseria meningitidis

<400> SEQUENCE: 7

Met Ser Met Lys His Phe Pro Ser Lys Val Leu Thr Thr Ala Ile Leu
1               5                   10                  15

Ala Thr Phe Cys Ser Gly Ala Leu Ala Ala Thr Ser Asp Asp Asp Val
                20                  25                  30

Lys Lys Ala Ala Thr Val Ala Ile Val Ala Ala Tyr Asn Asn Gly Gln
            35                  40                  45

Glu Ile Asn Gly Phe Lys Ala Gly Glu Thr Ile Tyr Asp Ile Gly Glu
        50                  55                  60

Asp Gly Thr Ile Thr Gln Lys Asp Ala Thr Ala Ala Asp Val Glu Ala
65                  70                  75                  80

Asp Asp Phe Lys Gly Leu Gly Leu Lys Lys Val Val Thr Asn Leu Thr
                85                  90                  95

Lys Thr Val Asn Glu Asn Lys Gln Asn Val Asp Ala Lys Val Lys Ala
            100                 105                 110

Ala Glu Ser Glu Ile Glu Lys Leu Thr Thr Lys Leu Ala Asp Thr Asp
        115                 120                 125

Ala Ala Leu Ala Asp Thr Asp Ala Ala Leu Asp Glu Thr Thr Asn Ala
    130                 135                 140
```

Leu Asn Lys Leu Gly Glu Asn Ile Thr Thr Phe Ala Glu Glu Thr Lys
145                 150                 155                 160

Thr Asn Ile Val Lys Ile Asp Glu Lys Leu Glu Ala Val Ala Asp Thr
            165                 170                 175

Val Asp Lys His Ala Glu Ala Phe Asn Asp Ile Ala Asp Ser Leu Asp
            180                 185                 190

Glu Thr Asn Thr Lys Ala Asp Glu Ala Val Lys Thr Ala Asn Glu Ala
            195                 200                 205

Lys Gln Thr Ala Glu Glu Thr Lys Gln Asn Val Asp Ala Lys Val Lys
    210                 215                 220

Ala Ala Glu Thr Ala Ala Gly Lys Ala Glu Ala Ala Gly Thr Ala
225                 230                 235                 240

Asn Thr Ala Ala Asp Lys Ala Glu Ala Val Ala Lys Val Thr Asp
                245                 250                 255

Ile Lys Ala Asp Ile Ala Thr Asn Lys Ala Asp Ile Ala Lys Asn Ser
        260                 265                 270

Ala Arg Ile Asp Ser Leu Asp Lys Asn Val Ala Asn Leu Arg Lys Glu
    275                 280                 285

Thr Arg Gln Gly Leu Ala Glu Gln Ala Ala Leu Ser Gly Leu Phe Gln
290                 295                 300

Pro Tyr Asn Val Gly Arg Phe Asn Val Thr Ala Ala Val Gly Tyr
305                 310                 315                 320

Lys Ser Glu Ser Ala Val Ala Ile Gly Thr Gly Phe Arg Phe Thr Glu
                325                 330                 335

Asn Phe Ala Ala Lys Ala Gly Val Ala Val Gly Thr Ser Ser Gly Ser
            340                 345                 350

Ser Ala Ala Tyr His Val Gly Val Asn Tyr Glu Trp
        355                 360

<210> SEQ ID NO 8
<211> LENGTH: 174
<212> TYPE: PRT
<213> ORGANISM: Neisseria meningitidis

<400> SEQUENCE: 8

Met Lys Lys Ala Leu Ala Thr Leu Ile Ala Leu Ala Leu Pro Ala Ala
1               5                   10                  15

Ala Leu Ala Glu Gly Ala Ser Gly Phe Tyr Val Gln Ala Asp Ala Ala
                20                  25                  30

His Ala Lys Ala Ser Ser Ser Leu Gly Ser Ala Lys Gly Phe Ser Pro
            35                  40                  45

Arg Ile Ser Ala Gly Tyr Arg Ile Asn Asp Leu Arg Phe Ala Val Asp
    50                  55                  60

Tyr Thr Arg Tyr Lys Asn Tyr Lys Ala Pro Ser Thr Asp Phe Lys Leu
65                  70                  75                  80

Tyr Ser Ile Gly Ala Ser Ala Ile Tyr Asp Phe Asp Thr Gln Ser Pro
                85                  90                  95

Val Lys Pro Tyr Leu Gly Ala Arg Leu Ser Leu Asn Arg Ala Ser Val
            100                 105                 110

Asp Leu Gly Gly Ser Asp Ser Phe Ser Gln Thr Ser Ile Gly Leu Gly
        115                 120                 125

Val Leu Thr Gly Val Ser Tyr Ala Val Thr Pro Asn Val Asp Leu Asp
    130                 135                 140

Ala Gly Tyr Arg Tyr Asn Tyr Ile Gly Lys Val Asn Thr Val Lys Asn
145                 150                 155                 160

Val Arg Ser Gly Glu Leu Ser Ala Gly Val Arg Val Lys Phe
            165                 170

<210> SEQ ID NO 9
<211> LENGTH: 792
<212> TYPE: PRT
<213> ORGANISM: Neisseria meningitidis

<400> SEQUENCE: 9

Met Lys Pro Leu Gln Met Leu Pro Ile Ala Ala Leu Val Gly Ser Ile
1               5                   10                  15

Phe Gly Asn Pro Val Leu Ala Ala Asp Glu Ala Ala Thr Glu Thr Thr
            20                  25                  30

Pro Val Lys Ala Glu Ile Lys Ala Val Arg Val Lys Gly Gln Arg Asn
        35                  40                  45

Ala Pro Ala Ala Val Glu Arg Val Asn Leu Asn Arg Ile Lys Gln Glu
    50                  55                  60

Met Ile Arg Asp Asn Lys Asp Leu Val Arg Tyr Ser Thr Asp Val Gly
65                  70                  75                  80

Leu Ser Asp Ser Gly Arg His Gln Lys Gly Phe Ala Val Arg Gly Val
                85                  90                  95

Glu Gly Asn Arg Val Gly Val Ser Ile Asp Gly Val Asn Leu Pro Asp
            100                 105                 110

Ser Glu Glu Asn Ser Leu Tyr Ala Arg Tyr Gly Asn Phe Asn Ser Ser
        115                 120                 125

Arg Leu Ser Ile Asp Pro Glu Leu Val Arg Asn Ile Glu Ile Val Lys
    130                 135                 140

Gly Ala Asp Ser Phe Asn Thr Gly Ser Gly Ala Leu Gly Gly Gly Val
145                 150                 155                 160

Asn Tyr Gln Thr Leu Gln Gly Arg Asp Leu Leu Asp Asp Arg Gln
                165                 170                 175

Phe Gly Val Met Met Lys Asn Gly Tyr Ser Thr Arg Asn Arg Glu Trp
            180                 185                 190

Thr Asn Thr Leu Gly Phe Gly Val Ser Asn Asp Arg Val Asp Ala Ala
        195                 200                 205

Leu Leu Tyr Ser Gln Arg Arg Gly His Glu Thr Glu Ser Ala Gly Asn
    210                 215                 220

Arg Gly Tyr Ala Val Glu Gly Glu Gly Ser Gly Ala Asn Ile Arg Gly
225                 230                 235                 240

Ser Ala Arg Gly Ile Pro Asp Ser Ser Lys His Lys Tyr Asn His His
                245                 250                 255

Ala Leu Gly Lys Ile Ala Tyr Gln Ile Asn Asp Asn His Arg Ile Gly
            260                 265                 270

Ala Ser Leu Asn Gly Gln Gln Gly His Asn Tyr Thr Val Glu Glu Ser
        275                 280                 285

Tyr Asn Leu Thr Ala Ser Ser Trp Arg Glu Ala Asp Val Asn Arg
    290                 295                 300

Arg Arg Asn Ala Asn Leu Phe Tyr Glu Trp Met Pro Asp Ser Asn Trp
305                 310                 315                 320

Leu Ser Ser Leu Lys Ala Asp Phe Asp Tyr Gln Lys Thr Lys Val Ala
                325                 330                 335

Ala Val Asn Asn Lys Gly Ser Phe Pro Met Asp Tyr Ser Thr Trp Thr
            340                 345                 350

Arg Asn Tyr Asn Gln Lys Asp Leu Asp Glu Ile Tyr Asn Arg Ser Met

```
            355                 360                 365
Asp Thr Arg Phe Lys Arg Phe Thr Leu Arg Leu Asp Ser His Pro Leu
370                 375                 380

Gln Leu Gly Gly Gly Arg His Arg Leu Ser Phe Lys Thr Phe Val Ser
385                 390                 395                 400

Arg Arg Asp Phe Glu Asn Leu Asn Arg Asp Tyr Tyr Phe Ser Gly
                    405                 410                 415

Arg Val Val Arg Thr Thr Ser Ser Ile Gln His Pro Val Lys Thr Thr
                420                 425                 430

Asn Tyr Gly Phe Ser Leu Ser Asp Gln Ile Gln Trp Asn Asp Val Phe
            435                 440                 445

Ser Ser Arg Ala Gly Ile Arg Tyr Asp His Thr Lys Met Thr Pro Gln
450                 455                 460

Glu Leu Asn Ala Glu Cys His Ala Cys Asp Lys Thr Pro Pro Ala Ala
465                 470                 475                 480

Asn Thr Tyr Lys Gly Trp Ser Gly Phe Val Gly Leu Ala Ala Gln Leu
                485                 490                 495

Asn Gln Ala Trp Arg Val Gly Tyr Asp Ile Thr Ser Gly Tyr Arg Val
            500                 505                 510

Pro Asn Ala Ser Glu Val Tyr Phe Thr Tyr Asn His Gly Ser Gly Asn
        515                 520                 525

Trp Leu Pro Asn Pro Asn Leu Lys Ala Glu Arg Ser Thr Thr His Thr
    530                 535                 540

Leu Ser Leu Gln Gly Arg Ser Glu Lys Gly Met Leu Asp Ala Asn Leu
545                 550                 555                 560

Tyr Gln Ser Asn Tyr Arg Asn Phe Leu Ser Glu Gln Lys Leu Thr
                565                 570                 575

Thr Ser Gly Thr Pro Gly Cys Thr Glu Glu Asn Ala Tyr Tyr Gly Ile
                580                 585                 590

Cys Ser Asp Pro Tyr Lys Glu Lys Leu Asp Trp Gln Met Lys Asn Ile
            595                 600                 605

Asp Lys Ala Arg Ile Arg Gly Ile Glu Leu Thr Gly Arg Leu Asn Val
    610                 615                 620

Asp Lys Val Ala Ser Phe Val Pro Glu Gly Trp Lys Leu Phe Gly Ser
625                 630                 635                 640

Leu Gly Tyr Ala Lys Ser Lys Leu Ser Gly Asp Asn Ser Leu Leu Ser
                645                 650                 655

Thr Gln Pro Leu Lys Val Ile Ala Gly Ile Asp Tyr Glu Ser Pro Ser
            660                 665                 670

Glu Lys Trp Gly Val Phe Ser Arg Leu Thr Tyr Leu Gly Ala Lys Lys
        675                 680                 685

Val Lys Asp Ala Gln Tyr Thr Val Tyr Glu Asn Lys Gly Trp Gly Thr
    690                 695                 700

Pro Leu Gln Lys Lys Val Lys Asp Tyr Pro Trp Leu Asn Lys Ser Ala
705                 710                 715                 720

Tyr Val Phe Asp Met Tyr Gly Phe Tyr Lys Pro Ala Lys Asn Leu Thr
                725                 730                 735

Leu Arg Ala Gly Val Tyr Asn Leu Phe Asn Arg Lys Tyr Thr Thr Trp
            740                 745                 750

Asp Ser Leu Arg Gly Leu Tyr Ser Tyr Ser Thr Thr Asn Ala Val Asp
        755                 760                 765

Arg Asp Gly Lys Gly Leu Asp Arg Tyr Arg Ala Pro Gly Arg Asn Tyr
    770                 775                 780
```

```
Ala Val Ser Leu Glu Trp Lys Phe
785             790

<210> SEQ ID NO 10
<211> LENGTH: 591
<212> TYPE: PRT
<213> ORGANISM: Neisseria meningitidis

<400> SEQUENCE: 10

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
                20                  25                  30

Thr Val Lys Thr Ala Val Leu Ala Thr Leu Leu Phe Ala Thr Val Gln
            35                  40                  45

Ala Ser Ala Asn Asn Glu Glu Gln Glu Glu Asp Leu Tyr Leu Asp Pro
        50                  55                  60

Val Gln Arg Thr Val Ala Val Leu Ile Val Asn Ser Asp Lys Glu Gly
65                  70                  75                  80

Thr Gly Glu Lys Glu Lys Val Glu Glu Asn Ser Asp Trp Ala Val Tyr
                85                  90                  95

Phe Asn Glu Lys Gly Val Leu Thr Ala Arg Glu Ile Thr Leu Lys Ala
                100                 105                 110

Gly Asp Asn Leu Lys Ile Lys Gln Asn Gly Thr Asn Phe Thr Tyr Ser
            115                 120                 125

Leu Lys Lys Asp Leu Thr Asp Leu Thr Ser Val Gly Thr Glu Lys Leu
        130                 135                 140

Ser Phe Ser Ala Asn Gly Asn Lys Val Asn Ile Thr Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Leu Asn
                180                 185                 190

Thr Gly Ala Thr Thr Asn Val Thr Asn Asp Asn Val Thr Asp Asp Glu
            195                 200                 205

Lys Lys Arg Ala Ala Ser Val Lys Asp Val Leu Asn Ala Gly Trp Asn
        210                 215                 220

Ile Lys Gly Val Lys Pro Gly Thr Thr Ala Ser Asp Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Lys Thr Glu Val
                260                 265                 270

Lys Ile Gly Ala Lys Thr Ser Val Ile Lys Glu Lys Asp Gly Lys Leu
            275                 280                 285

Val Thr Gly Lys Asp Lys Gly Glu Asn Gly Ser Ser Thr Asp Glu Gly
        290                 295                 300

Glu Gly Leu Val Thr Ala Lys Glu Val Ile Asp Ala Val Asn Lys Ala
305                 310                 315                 320

Gly Trp Arg Met Lys Thr Thr Ala Asn Gly Gln Thr Gly Gln Ala
                325                 330                 335

Asp Lys Phe Glu Thr Val Thr Ser Gly Thr Asn Val Thr Phe Ala Ser
            340                 345                 350

Gly Lys Gly Thr Thr Ala Thr Val Ser Lys Asp Asp Gln Gly Asn Ile
```

```
                355                 360                 365
Thr Val Met Tyr Asp Val Asn Val Gly Asp Ala Leu Asn Val Asn Gln
    370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
                405                 410                 415

Asp Glu Thr Val Asn Ile Asn Ala Gly Asn Asn Ile Glu Ile Thr Arg
            420                 425                 430

Asn Gly Lys Asn Ile Asp Ile Ala Thr Ser Met Thr Pro Gln Phe Ser
        435                 440                 445

Ser Val Ser Leu Gly Ala Gly Ala Asp Ala Pro Thr Leu Ser Val Asp
    450                 455                 460

Gly Asp Ala Leu Asn Val Gly Ser Lys Lys Asp Asn Lys Pro Val Arg
465                 470                 475                 480

Ile Thr Asn Val Ala Pro Gly Val Lys Glu Gly Asp Val Thr Asn Val
                485                 490                 495

Ala Gln Leu Lys Gly Val Ala Gln Asn Leu Asn Asn Arg Ile Asp Asn
            500                 505                 510

Val Asp Gly Asn Ala Arg Ala Gly Ile Ala Gln Ala Ile Ala Thr Ala
        515                 520                 525

Gly Leu Val Gln Ala Tyr Leu Pro Gly Lys Ser Met Met Ala Ile Gly
    530                 535                 540

Gly Gly Thr Tyr Arg Gly Glu Ala Gly Tyr Ala Ile Gly Tyr Ser Ser
545                 550                 555                 560

Ile Ser Asp Gly Gly Asn Trp Ile Ile Lys Gly Thr Ala Ser Gly Asn
                565                 570                 575

Ser Arg Gly His Phe Gly Ala Ser Ala Ser Val Gly Tyr Gln Trp
            580                 585                 590

<210> SEQ ID NO 11
<211> LENGTH: 1457
<212> TYPE: PRT
<213> ORGANISM: Neisseria meningitidis

<400> SEQUENCE: 11

Met Lys Thr Thr Asp Lys Arg Thr Thr Glu Thr His Arg Lys Ala Pro
1               5                   10                  15

Lys Thr Gly Arg Ile Arg Phe Ser Pro Ala Tyr Leu Ala Ile Cys Leu
            20                  25                  30

Ser Phe Gly Ile Leu Pro Gln Ala Trp Ala Gly His Thr Tyr Phe Gly
        35                  40                  45

Ile Asn Tyr Gln Tyr Tyr Arg Asp Phe Ala Glu Asn Lys Gly Lys Phe
    50                  55                  60

Ala Val Gly Ala Lys Asp Ile Glu Val Tyr Asn Lys Lys Gly Glu Leu
65                  70                  75                  80

Val Gly Lys Ser Met Thr Lys Ala Pro Met Ile Asp Phe Ser Val Val
                85                  90                  95

Ser Arg Asn Gly Val Ala Ala Leu Val Gly Asp Gln Tyr Ile Val Ser
            100                 105                 110

Val Ala His Asn Gly Gly Tyr Asn Asn Val Asp Phe Gly Ala Glu Gly
        115                 120                 125

Arg Asn Pro Asp Gln His Arg Phe Thr Tyr Lys Ile Val Lys Arg Asn
    130                 135                 140
```

Asn Tyr Lys Ala Gly Thr Lys Gly His Pro Tyr Gly Gly Asp Tyr His
145                 150                 155                 160

Met Pro Arg Leu His Lys Phe Val Thr Asp Ala Glu Pro Val Glu Met
                165                 170                 175

Thr Ser Tyr Met Asp Gly Arg Lys Tyr Ile Asp Gln Asn Asn Tyr Pro
            180                 185                 190

Asp Arg Val Arg Ile Gly Ala Gly Arg Gln Tyr Trp Arg Ser Asp Glu
        195                 200                 205

Asp Glu Pro Asn Asn Arg Glu Ser Ser Tyr His Ile Ala Ser Ala Tyr
    210                 215                 220

Ser Trp Leu Val Gly Gly Asn Thr Phe Ala Gln Asn Gly Ser Gly Gly
225                 230                 235                 240

Gly Thr Val Asn Leu Gly Ser Glu Lys Ile Lys His Ser Pro Tyr Gly
                245                 250                 255

Phe Leu Pro Thr Gly Gly Ser Phe Gly Asp Ser Gly Ser Pro Met Phe
            260                 265                 270

Ile Tyr Asp Ala Gln Lys Gln Lys Trp Leu Ile Asn Gly Val Leu Gln
        275                 280                 285

Thr Gly Asn Pro Tyr Ile Gly Lys Ser Asn Gly Phe Gln Leu Val Arg
    290                 295                 300

Lys Asp Trp Phe Tyr Asp Glu Ile Phe Ala Gly Asp Thr His Ser Val
305                 310                 315                 320

Phe Tyr Glu Pro Arg Gln Asn Gly Lys Tyr Ser Phe Asn Asp Asp Asn
                325                 330                 335

Asn Gly Thr Gly Lys Ile Asn Ala Lys His Glu His Asn Ser Leu Pro
            340                 345                 350

Asn Arg Leu Lys Thr Arg Thr Val Gln Leu Phe Asn Val Ser Leu Ser
        355                 360                 365

Glu Thr Ala Arg Glu Pro Val Tyr His Ala Ala Gly Gly Val Asn Ser
    370                 375                 380

Tyr Arg Pro Arg Leu Asn Asn Gly Glu Asn Ile Ser Phe Ile Asp Glu
385                 390                 395                 400

Gly Lys Gly Glu Leu Ile Leu Thr Ser Asn Ile Asn Gln Gly Ala Gly
                405                 410                 415

Gly Leu Tyr Phe Gln Gly Asp Phe Thr Val Ser Pro Glu Asn Asn Glu
            420                 425                 430

Thr Trp Gln Gly Ala Gly Val His Ile Ser Glu Asp Ser Thr Val Thr
        435                 440                 445

Trp Lys Val Asn Gly Val Ala Asn Asp Arg Leu Ser Lys Ile Gly Lys
450                 455                 460

Gly Thr Leu His Val Gln Ala Lys Gly Glu Asn Gln Gly Ser Ile Ser
465                 470                 475                 480

Val Gly Asp Gly Thr Val Ile Leu Asp Gln Gln Ala Asp Lys Gly
                485                 490                 495

Lys Lys Gln Ala Phe Ser Glu Ile Gly Leu Val Ser Gly Arg Gly Thr
            500                 505                 510

Val Gln Leu Asn Ala Asp Asn Gln Phe Asn Pro Asp Lys Leu Tyr Phe
        515                 520                 525

Gly Phe Arg Gly Gly Arg Leu Asp Leu Asn Gly His Ser Leu Ser Phe
    530                 535                 540

His Arg Ile Gln Asn Thr Asp Glu Gly Ala Met Ile Val Asn His Asn
545                 550                 555                 560

Gln Asp Lys Glu Ser Thr Val Thr Ile Thr Gly Asn Lys Asp Ile Ala

```
                        565                 570                 575
Thr Thr Gly Asn Asn Asn Ser Leu Asp Ser Lys Lys Glu Ile Ala Tyr
                580                 585                 590

Asn Gly Trp Phe Gly Glu Lys Asp Thr Thr Lys Thr Asn Gly Arg Leu
                595                 600             605

Asn Leu Val Tyr Gln Pro Ala Ala Glu Asp Arg Thr Leu Leu Leu Ser
            610                 615                 620

Gly Gly Thr Asn Leu Asn Gly Asn Ile Thr Gln Thr Asn Gly Lys Leu
625                 630                 635                 640

Phe Phe Ser Gly Arg Pro Thr Pro His Ala Tyr Asn His Leu Asn Asp
                645                 650                 655

His Trp Ser Gln Lys Glu Gly Ile Pro Arg Gly Glu Ile Val Trp Asp
                660                 665                 670

Asn Asp Trp Ile Asn Arg Thr Phe Lys Ala Glu Asn Phe Gln Ile Lys
                675                 680                 685

Gly Gly Gln Ala Val Val Ser Arg Asn Val Ala Lys Val Lys Gly Asp
            690                 695                 700

Trp His Leu Ser Asn His Ala Gln Ala Val Phe Gly Val Ala Pro His
705                 710                 715                 720

Gln Ser His Thr Ile Cys Thr Arg Ser Asp Trp Thr Gly Leu Thr Asn
                    725                 730                 735

Cys Val Glu Lys Thr Ile Thr Asp Asp Lys Val Ile Ala Ser Leu Thr
                740                 745                 750

Lys Thr Asp Ile Ser Gly Asn Val Asp Leu Ala Asp His Ala His Leu
                755                 760                 765

Asn Leu Thr Gly Leu Ala Thr Leu Asn Gly Asn Leu Ser Ala Asn Gly
            770                 775                 780

Asp Thr Arg Tyr Thr Val Ser His Asn Ala Thr Gln Asn Gly Asn Leu
785                 790                 795                 800

Ser Leu Val Gly Asn Ala Gln Ala Thr Phe Asn Gln Ala Thr Leu Asn
                805                 810                 815

Gly Asn Thr Ser Ala Ser Gly Asn Ala Ser Phe Asn Leu Ser Asp His
                820                 825                 830

Ala Val Gln Asn Gly Ser Leu Thr Leu Ser Gly Asn Ala Lys Ala Asn
                835                 840                 845

Val Ser His Ser Ala Leu Asn Gly Asn Val Ser Leu Ala Asp Lys Ala
850                 855                 860

Val Phe His Phe Glu Ser Ser Arg Phe Thr Gly Gln Ile Ser Gly Gly
865                 870                 875                 880

Lys Asp Thr Ala Leu His Leu Lys Asp Ser Glu Trp Thr Leu Pro Ser
                885                 890                 895

Gly Thr Glu Leu Gly Asn Leu Asn Leu Asp Asn Ala Thr Ile Thr Leu
                900                 905                 910

Asn Ser Ala Tyr Arg His Asp Ala Ala Gly Ala Gln Thr Gly Ser Ala
                915                 920                 925

Thr Asp Ala Pro Arg Arg Ser Arg Arg Ser Arg Ser Leu Leu
930                 935                 940

Ser Val Thr Pro Pro Thr Ser Val Glu Ser Arg Phe Asn Thr Leu Thr
945                 950                 955                 960

Val Asn Gly Lys Leu Asn Gly Gln Gly Thr Phe Arg Phe Met Ser Glu
                965                 970                 975

Leu Phe Gly Tyr Arg Ser Asp Lys Leu Lys Leu Ala Glu Ser Ser Glu
                980                 985                 990
```

```
Gly Thr Tyr Thr Leu Ala Val Asn  Asn Thr Gly Asn Glu  Pro Ala Ser
        995                 1000                 1005

Leu Glu  Gln Leu Thr Val  Val  Glu Gly Lys Asp Asn  Lys Pro Leu
    1010                 1015                 1020

Ser Glu  Asn Leu Asn Phe Thr  Leu Gln Asn Glu His  Val Asp Ala
    1025                 1030                 1035

Gly Ala  Trp Arg Tyr Gln Leu  Ile Arg Lys Asp Gly  Glu Phe Arg
    1040                 1045                 1050

Leu His  Asn Pro Val Lys Glu  Gln Glu Leu Ser Asp  Lys Leu Gly
    1055                 1060                 1065

Lys Ala  Glu Ala Lys Lys Gln  Ala Glu Lys Asp Asn  Ala Gln Ser
    1070                 1075                 1080

Leu Asp  Ala Leu Ile Ala Ala  Gly Arg Asp Ala Val  Glu Lys Thr
    1085                 1090                 1095

Glu Ser  Val Ala Glu Pro Ala  Arg Gln Ala Gly Gly  Glu Asn Val
    1100                 1105                 1110

Gly Ile  Met Gln Ala Glu Glu  Glu Lys Lys Arg Val  Gln Ala Asp
    1115                 1120                 1125

Lys Asp  Thr Ala Leu Ala Lys  Gln Arg Glu Ala Glu  Thr Arg Pro
    1130                 1135                 1140

Ala Thr  Thr Ala Phe Pro Arg  Ala Arg Arg Ala Arg  Arg Asp Leu
    1145                 1150                 1155

Pro Gln  Leu Gln Pro Gln Pro  Gln Pro Gln Pro Gln  Arg Asp Leu
    1160                 1165                 1170

Ile Ser  Arg Tyr Ala Asn Ser  Gly Leu Ser Glu Phe  Ser Ala Thr
    1175                 1180                 1185

Leu Asn  Ser Val Phe Ala Val  Gln Asp Glu Leu Asp  Arg Val Phe
    1190                 1195                 1200

Ala Glu  Asp Arg Arg Asn Ala  Val Trp Thr Ser Gly  Ile Arg Asp
    1205                 1210                 1215

Thr Lys  His Tyr Arg Ser Gln  Asp Phe Arg Ala Tyr  Arg Gln Gln
    1220                 1225                 1230

Thr Asp  Leu Arg Gln Ile Gly  Met Gln Lys Asn Leu  Gly Ser Gly
    1235                 1240                 1245

Arg Val  Gly Ile Leu Phe Ser  His Asn Arg Thr Glu  Asn Thr Phe
    1250                 1255                 1260

Asp Asp  Gly Ile Gly Asn Ser  Ala Arg Leu Ala His  Gly Ala Val
    1265                 1270                 1275

Phe Gly  Gln Tyr Gly Ile Asp  Arg Phe Tyr Ile Gly  Ile Ser Ala
    1280                 1285                 1290

Gly Ala  Gly Phe Ser Ser Gly  Ser Leu Ser Asp Gly  Ile Gly Gly
    1295                 1300                 1305

Lys Ile  Arg Arg Arg Val Leu  His Tyr Gly Ile Gln  Ala Arg Tyr
    1310                 1315                 1320

Arg Ala  Gly Phe Gly Gly Phe  Gly Ile Glu Pro His  Ile Gly Ala
    1325                 1330                 1335

Thr Arg  Tyr Phe Val Gln Lys  Ala Asp Tyr Arg Tyr  Glu Asn Val
    1340                 1345                 1350

Asn Ile  Ala Thr Pro Gly Leu  Ala Phe Asn Arg Tyr  Arg Ala Gly
    1355                 1360                 1365

Ile Lys  Ala Asp Tyr Ser Phe  Lys Pro Ala Gln His  Ile Ser Ile
    1370                 1375                 1380
```

```
Thr Pro Tyr Leu Ser Leu Ser Tyr Thr Asp Ala Ala Ser Gly Lys
    1385                1390                1395

Val Arg Thr Arg Val Asn Thr Ala Val Leu Ala Gln Asp Phe Gly
1400                1405                1410

Lys Thr Arg Ser Ala Glu Trp Gly Val Asn Ala Glu Ile Lys Gly
    1415                1420                1425

Phe Thr Leu Ser Leu His Ala Ala Ala Lys Gly Pro Gln Leu
    1430                1435                1440

Glu Ala Gln His Ser Ala Gly Ile Lys Leu Gly Tyr Arg Trp
    1445                1450                1455

<210> SEQ ID NO 12
<211> LENGTH: 797
<212> TYPE: PRT
<213> ORGANISM: Neisseria meningitidis

<400> SEQUENCE: 12

Met Lys Leu Lys Gln Ile Ala Ser Ala Leu Met Met Leu Gly Ile Ser
1               5                   10                  15

Pro Leu Ala Leu Ala Asp Phe Thr Ile Gln Asp Ile Arg Val Glu Gly
                20                  25                  30

Leu Gln Arg Thr Glu Pro Ser Thr Val Phe Asn Tyr Leu Pro Val Lys
            35                  40                  45

Val Gly Asp Thr Tyr Asn Asp Thr His Gly Ser Ala Ile Ile Lys Ser
        50                  55                  60

Leu Tyr Ala Thr Gly Phe Phe Asp Asp Val Arg Val Glu Thr Ala Asp
65                  70                  75                  80

Gly Gln Leu Leu Leu Thr Val Ile Glu Arg Pro Thr Ile Gly Ser Leu
                85                  90                  95

Asn Ile Thr Gly Ala Lys Met Leu Gln Asn Asp Ala Ile Lys Lys Asn
                100                 105                 110

Leu Glu Ser Phe Gly Leu Ala Gln Ser Gln Tyr Phe Asn Gln Ala Thr
            115                 120                 125

Leu Asn Gln Ala Val Ala Gly Leu Lys Glu Glu Tyr Leu Gly Arg Gly
        130                 135                 140

Lys Leu Asn Ile Gln Ile Thr Pro Lys Val Thr Lys Leu Ala Arg Asn
145                 150                 155                 160

Arg Val Asp Ile Asp Ile Thr Ile Asp Glu Gly Lys Ser Ala Lys Ile
                165                 170                 175

Thr Asp Ile Glu Phe Glu Gly Asn Gln Val Tyr Ser Asp Arg Lys Leu
                180                 185                 190

Met Arg Gln Met Ser Leu Thr Glu Gly Gly Ile Trp Thr Trp Leu Thr
            195                 200                 205

Arg Ser Asn Gln Phe Asn Gln Lys Phe Ala Gln Asp Met Glu Lys
        210                 215                 220

Val Thr Asp Phe Tyr Gln Asn Asn Gly Tyr Phe Asp Phe Arg Ile Leu
225                 230                 235                 240

Asp Thr Asp Ile Gln Thr Asn Glu Asp Lys Thr Lys Gln Thr Ile Lys
                245                 250                 255

Ile Thr Val His Glu Gly Gly Arg Phe Arg Trp Gly Lys Val Ser Ile
                260                 265                 270

Glu Gly Asp Thr Asn Glu Val Pro Lys Ala Glu Leu Glu Lys Leu Leu
            275                 280                 285

Thr Met Lys Pro Gly Lys Trp Tyr Glu Arg Gln Gln Met Thr Ala Val
        290                 295                 300
```

```
Leu Gly Glu Ile Gln Asn Arg Met Gly Ser Ala Gly Tyr Ala Tyr Ser
305                 310                 315                 320

Glu Ile Ser Val Gln Pro Leu Pro Asn Ala Glu Thr Lys Thr Val Asp
                325                 330                 335

Phe Val Leu His Ile Glu Pro Gly Arg Lys Ile Tyr Val Asn Glu Ile
            340                 345                 350

His Ile Thr Gly Asn Asn Lys Thr Arg Asp Glu Val Val Arg Arg Glu
        355                 360                 365

Leu Arg Gln Met Glu Ser Ala Pro Tyr Asp Thr Ser Lys Leu Gln Arg
    370                 375                 380

Ser Lys Glu Arg Val Glu Leu Leu Gly Tyr Phe Asp Asn Val Gln Phe
385                 390                 395                 400

Asp Ala Val Pro Leu Ala Gly Thr Pro Asp Lys Val Asp Leu Asn Met
                405                 410                 415

Ser Leu Thr Glu Arg Ser Thr Gly Ser Leu Asp Leu Ser Ala Gly Trp
            420                 425                 430

Val Gln Asp Thr Gly Leu Val Met Ser Ala Gly Val Ser Gln Asp Asn
        435                 440                 445

Leu Phe Gly Thr Gly Lys Ser Ala Ala Leu Arg Ala Ser Arg Ser Lys
    450                 455                 460

Thr Thr Leu Asn Gly Ser Leu Ser Phe Thr Asp Pro Tyr Phe Thr Ala
465                 470                 475                 480

Asp Gly Val Ser Leu Gly Tyr Asp Val Tyr Gly Lys Ala Phe Asp Pro
                485                 490                 495

Arg Lys Ala Ser Thr Ser Ile Lys Gln Tyr Lys Thr Thr Thr Ala Gly
            500                 505                 510

Ala Gly Ile Arg Met Ser Val Pro Val Thr Glu Tyr Asp Arg Val Asn
        515                 520                 525

Phe Gly Leu Val Ala Glu His Leu Thr Val Asn Thr Tyr Asn Lys Ala
    530                 535                 540

Pro Lys His Tyr Ala Asp Phe Ile Lys Lys Tyr Gly Lys Thr Asp Gly
545                 550                 555                 560

Thr Asp Gly Ser Phe Lys Gly Trp Leu Tyr Lys Gly Thr Val Gly Trp
                565                 570                 575

Gly Arg Asn Lys Thr Asp Ser Ala Leu Trp Pro Thr Arg Gly Tyr Leu
            580                 585                 590

Thr Gly Val Asn Ala Glu Ile Ala Leu Pro Gly Ser Lys Leu Gln Tyr
        595                 600                 605

Tyr Ser Ala Thr His Asn Gln Thr Trp Phe Phe Pro Leu Ser Lys Thr
    610                 615                 620

Phe Thr Leu Met Leu Gly Gly Glu Val Gly Ile Ala Gly Gly Tyr Gly
625                 630                 635                 640

Arg Thr Lys Glu Ile Pro Phe Phe Glu Asn Phe Tyr Gly Gly Gly Leu
                645                 650                 655

Gly Ser Val Arg Gly Tyr Glu Ser Gly Thr Leu Gly Pro Lys Val Tyr
            660                 665                 670

Asp Glu Tyr Gly Glu Lys Ile Ser Tyr Gly Gly Asn Lys Lys Ala Asn
        675                 680                 685

Val Ser Ala Glu Leu Leu Phe Pro Met Pro Gly Ala Lys Asp Ala Arg
    690                 695                 700

Thr Val Arg Leu Ser Leu Phe Ala Asp Ala Gly Ser Val Trp Asp Gly
705                 710                 715                 720
```

```
Lys Thr Tyr Asp Asp Asn Ser Ser Ala Thr Gly Gly Arg Val Gln
                725                 730                 735

Asn Ile Tyr Gly Ala Gly Asn Thr His Lys Ser Thr Phe Thr Asn Glu
            740                 745                 750

Leu Arg Tyr Ser Ala Gly Gly Ala Val Thr Trp Leu Ser Pro Leu Gly
                755                 760                 765

Pro Met Lys Phe Ser Tyr Ala Tyr Pro Leu Lys Lys Pro Glu Asp
        770                 775                 780

Glu Ile Gln Arg Phe Gln Phe Gln Leu Gly Thr Thr Phe
785                 790                 795
```

<210> SEQ ID NO 13
<211> LENGTH: 180
<212> TYPE: PRT
<213> ORGANISM: Neisseria meningitidis

<400> SEQUENCE: 13

```
Met Val Ser Ala Val Ile Gly Ser Ala Ala Val Gly Ala Lys Ser Ala
1               5                   10                  15

Val Asp Arg Arg Thr Thr Gly Ala Gln Thr Asp Asp Asn Val Met Ala
            20                  25                  30

Leu Arg Ile Glu Thr Thr Ala Arg Ser Tyr Leu Arg Gln Asn Asn Gln
        35                  40                  45

Thr Lys Gly Tyr Thr Pro Gln Ile Ser Val Val Gly Tyr Asp Arg His
    50                  55                  60

Leu Leu Leu Leu Gly Gln Val Ala Thr Glu Gly Glu Lys Gln Phe Val
65                  70                  75                  80

Gly Gln Ile Ala Arg Ser Glu Gln Ala Ala Glu Gly Val Tyr Asn Tyr
                85                  90                  95

Ile Thr Val Ala Ser Leu Pro Arg Thr Ala Gly Asp Ile Ala Gly Asp
            100                 105                 110

Thr Trp Asn Thr Ser Lys Val Arg Ala Thr Leu Leu Gly Ile Ser Pro
        115                 120                 125

Ala Thr Arg Ala Arg Val Lys Ile Val Thr Tyr Gly Asn Val Thr Tyr
    130                 135                 140

Val Met Gly Ile Leu Thr Pro Glu Glu Gln Ala Gln Ile Thr Gln Lys
145                 150                 155                 160

Val Ser Thr Thr Val Gly Val Gln Lys Val Ile Thr Leu Tyr Gln Asn
                165                 170                 175

Tyr Val Gln Arg
        180
```

<210> SEQ ID NO 14
<211> LENGTH: 644
<212> TYPE: PRT
<213> ORGANISM: Neisseria meningitidis

<400> SEQUENCE: 14

```
Met Ala Ser Pro Asp Val Lys Ser Ala Asp Thr Leu Ser Lys Pro Ala
1               5                   10                  15

Ala Pro Val Val Ser Glu Lys Glu Thr Glu Ala Lys Glu Asp Ala Pro
            20                  25                  30

Gln Ala Gly Ser Gln Gly Gln Gly Ala Pro Ser Ala Gln Gly Gly Gln
        35                  40                  45

Asp Met Ala Ala Val Ser Glu Glu Asn Thr Gly Asn Gly Gly Ala Ala
    50                  55                  60
```

```
Ala Thr Asp Lys Pro Lys Asn Glu Asp Glu Gly Ala Gln Asn Asp Met
 65                  70                  75                  80

Pro Gln Asn Ala Ala Asp Thr Asp Ser Leu Thr Pro Asn His Thr Pro
             85                  90                  95

Ala Ser Asn Met Pro Ala Gly Asn Met Glu Asn Gln Ala Pro Asp Ala
            100                 105                 110

Gly Glu Ser Glu Gln Pro Ala Asn Gln Pro Asp Met Ala Asn Thr Ala
        115                 120                 125

Asp Gly Met Gln Gly Asp Pro Ser Ala Gly Glu Asn Ala Gly
    130                 135                 140

Asn Thr Ala Ala Gln Gly Thr Asn Gln Ala Glu Asn Asn Gln Thr Ala
145                 150                 155                 160

Gly Ser Gln Asn Pro Ala Ser Ser Thr Asn Pro Ser Ala Thr Asn Ser
                165                 170                 175

Gly Gly Asp Phe Gly Arg Thr Asn Val Gly Asn Ser Val Val Ile Asp
            180                 185                 190

Gly Pro Ser Gln Asn Ile Thr Leu Thr His Cys Lys Gly Asp Ser Cys
        195                 200                 205

Ser Gly Asn Asn Phe Leu Asp Glu Glu Val Gln Leu Lys Ser Glu Phe
    210                 215                 220

Glu Lys Leu Ser Asp Ala Asp Lys Ile Ser Asn Tyr Lys Lys Asp Gly
225                 230                 235                 240

Lys Asn Asp Gly Lys Asn Asp Lys Phe Val Gly Leu Val Ala Asp Ser
                245                 250                 255

Val Gln Met Lys Gly Ile Asn Gln Tyr Ile Ile Phe Tyr Lys Pro Lys
            260                 265                 270

Pro Thr Ser Phe Ala Arg Phe Arg Arg Ser Ala Arg Ser Arg Arg Ser
        275                 280                 285

Leu Pro Ala Glu Met Pro Leu Ile Pro Val Asn Gln Ala Asp Thr Leu
    290                 295                 300

Ile Val Asp Gly Glu Ala Val Ser Leu Thr Gly His Ser Gly Asn Ile
305                 310                 315                 320

Phe Ala Pro Glu Gly Asn Tyr Arg Tyr Leu Thr Tyr Gly Ala Glu Lys
                325                 330                 335

Leu Pro Gly Gly Ser Tyr Ala Leu Arg Val Gln Gly Glu Pro Ser Lys
            340                 345                 350

Gly Glu Met Leu Ala Gly Thr Ala Val Tyr Asn Gly Glu Val Leu His
        355                 360                 365

Phe His Thr Glu Asn Gly Arg Pro Ser Pro Ser Arg Gly Arg Phe Ala
    370                 375                 380

Ala Lys Val Asp Phe Gly Ser Lys Ser Val Asp Gly Ile Ile Asp Ser
385                 390                 395                 400

Gly Asp Gly Leu His Met Gly Thr Gln Lys Phe Lys Ala Ala Ile Asp
                405                 410                 415

Gly Asn Gly Phe Lys Gly Thr Trp Thr Glu Asn Gly Gly Asp Val
            420                 425                 430

Ser Gly Lys Phe Tyr Gly Pro Ala Gly Glu Glu Val Ala Gly Lys Tyr
        435                 440                 445

Ser Tyr Arg Pro Thr Asp Ala Glu Lys Gly Gly Phe Gly Val Phe Ala
    450                 455                 460

Gly Lys Lys Glu Gln Asp Gly Ser Gly Gly Gly Ala Thr Tyr Lys
465                 470                 475                 480

Val Asp Glu Tyr His Ala Asn Ala Arg Phe Ala Ile Asp His Phe Asn
```

```
            485                 490                 495
Thr Ser Thr Asn Val Gly Gly Phe Tyr Gly Leu Thr Gly Ser Val Glu
            500                 505                 510

Phe Asp Gln Ala Lys Arg Asp Gly Lys Ile Asp Ile Thr Ile Pro Val
            515                 520                 525

Ala Asn Leu Gln Ser Gly Ser Gln His Phe Thr Asp His Leu Lys Ser
            530                 535                 540

Ala Asp Ile Phe Asp Ala Ala Gln Tyr Pro Asp Ile Arg Phe Val Ser
545                 550                 555                 560

Thr Lys Phe Asn Phe Asn Gly Lys Lys Leu Val Ser Val Asp Gly Asn
            565                 570                 575

Leu Thr Met His Gly Lys Thr Ala Pro Val Lys Leu Lys Ala Glu Lys
            580                 585                 590

Phe Asn Cys Tyr Gln Ser Pro Met Ala Lys Thr Glu Val Cys Gly Gly
            595                 600                 605

Asp Phe Ser Thr Thr Ile Asp Arg Thr Lys Trp Gly Val Asp Tyr Leu
            610                 615                 620

Val Asn Val Gly Met Thr Lys Ser Val Arg Ile Asp Ile Gln Ile Glu
625                 630                 635                 640

Ala Ala Lys Gln

<210> SEQ ID NO 15
<211> LENGTH: 327
<212> TYPE: PRT
<213> ORGANISM: Neisseria meningitidis

<400> SEQUENCE: 15

Ala Thr Asn Asp Asp Val Lys Lys Ala Ala Thr Val Ala Ile Ala
1               5                   10                  15

Ala Ala Tyr Asn Asn Gly Gln Glu Ile Asn Gly Phe Lys Ala Gly Glu
                20                  25                  30

Thr Ile Tyr Asp Ile Asp Glu Asp Gly Thr Ile Thr Lys Lys Asp Ala
            35                  40                  45

Thr Ala Ala Asp Val Glu Ala Asp Asp Phe Lys Gly Leu Gly Leu Lys
        50                  55                  60

Lys Val Val Thr Asn Leu Thr Lys Thr Val Asn Glu Asn Lys Gln Asn
65                  70                  75                  80

Val Asp Ala Lys Val Lys Ala Ala Glu Ser Glu Ile Glu Lys Leu Thr
                85                  90                  95

Thr Lys Leu Ala Asp Thr Asp Ala Ala Leu Ala Asp Thr Asp Ala Ala
            100                 105                 110

Leu Asp Ala Thr Thr Asn Ala Leu Asn Lys Leu Gly Glu Asn Ile Thr
        115                 120                 125

Thr Phe Ala Glu Glu Thr Lys Thr Asn Ile Val Lys Ile Asp Glu Lys
    130                 135                 140

Leu Glu Ala Val Ala Asp Thr Val Asp Lys His Ala Glu Ala Phe Asn
145                 150                 155                 160

Asp Ile Ala Asp Ser Leu Asp Glu Thr Asn Thr Lys Ala Asp Glu Ala
                165                 170                 175

Val Lys Thr Ala Asn Glu Ala Lys Gln Thr Ala Glu Glu Thr Lys Gln
            180                 185                 190

Asn Val Asp Ala Lys Val Lys Ala Ala Glu Thr Ala Ala Gly Lys Ala
        195                 200                 205

Glu Ala Ala Ala Gly Thr Ala Asn Thr Ala Ala Asp Lys Ala Glu Ala
```

```
            210                 215                 220
Val Ala Lys Val Thr Asp Ile Lys Ala Asp Ile Ala Thr Asn Lys
225                 230                 235                 240

Asp Asn Ile Ala Lys Lys Ala Asn Ser Ala Asp Val Tyr Thr Arg Glu
                245                 250                 255

Glu Ser Asp Ser Lys Phe Val Arg Ile Asp Gly Leu Asn Ala Thr Thr
                260                 265                 270

Glu Lys Leu Asp Thr Arg Leu Ala Ser Ala Glu Lys Ser Ile Ala Asp
                275                 280                 285

His Asp Thr Arg Leu Asn Gly Leu Asp Lys Thr Val Ser Asp Leu Arg
                290                 295                 300

Lys Glu Thr Arg Gln Gly Leu Ala Glu Gln Ala Ala Leu Ser Gly Leu
305                 310                 315                 320

Phe Gln Pro Tyr Asn Val Gly
                325

<210> SEQ ID NO 16
<211> LENGTH: 248
<212> TYPE: PRT
<213> ORGANISM: Neisseria meningitidis

<400> SEQUENCE: 16

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
                20                  25                  30

Val Arg Lys Asn Glu Lys Leu Lys Leu Ala Ala Gln Gly Ala Glu Lys
                35                  40                  45

Thr Tyr Gly Asn Gly Asp Ser Leu Asn Thr Gly Lys Leu Lys Asn Asp
50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
                100                 105                 110

Ser Gly Lys Met Val Ala Lys Arg Gln Phe Arg Ile Gly Asp Ile Ala
                115                 120                 125

Gly Glu His Thr Ser Phe Asp Lys Leu Pro Glu Gly Gly Arg Ala Thr
                130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Asp Leu Ala Ala Ala Asp Ile Lys
                180                 185                 190

Pro Asp Gly Lys Arg His Ala Val Ile Ser Gly Ser Val Leu Tyr Asn
                195                 200                 205

Gln Ala Glu Lys Gly Ser Tyr Ser Leu Gly Ile Phe Gly Gly Lys Ala
                210                 215                 220

Gln Glu Val Ala Gly Ser Ala Glu Val Lys Thr Val Asn Gly Ile Arg
225                 230                 235                 240

His Ile Gly Leu Ala Ala Lys Gln
                245
```

<210> SEQ ID NO 17
<211> LENGTH: 250
<212> TYPE: PRT
<213> ORGANISM: Neisseria meningitidis

<400> SEQUENCE: 17

Val Ala Ala Asp Ile Gly Thr Gly Leu Ala Asp Ala Leu Thr Ala Pro
1               5                   10                  15

Leu Asp His Lys Asp Lys Gly Leu Lys Ser Leu Thr Leu Glu Asp Ser
            20                  25                  30

Ile Pro Gln Asn Gly Thr Leu Thr Leu Ser Ala Gln Gly Ala Glu Lys
        35                  40                  45

Thr Phe Lys Ala Gly Asp Lys Asp Asn Ser Leu Asn Thr Gly Lys Leu
    50                  55                  60

Lys Asn Asp Lys Ile Ser Arg Phe Asp Phe Val Gln Lys Ile Glu Val
65                  70                  75                  80

Asp Gly Gln Thr Ile Thr Leu Ala Ser Gly Glu Phe Gln Ile Tyr Lys
                85                  90                  95

Gln Asn His Ser Ala Val Val Ala Leu Gln Ile Glu Lys Ile Asn Asn
            100                 105                 110

Pro Asp Lys Thr Asp Ser Leu Ile Asn Gln Arg Ser Phe Leu Val Ser
        115                 120                 125

Gly Leu Gly Gly Glu His Thr Ala Phe Asn Gln Leu Pro Gly Gly Lys
    130                 135                 140

Ala Glu Tyr His Gly Lys Ala Phe Ser Ser Asp Asp Pro Asn Gly Arg
145                 150                 155                 160

Leu His Tyr Ser Ile Asp Phe Thr Lys Lys Gln Gly Tyr Gly Arg Ile
                165                 170                 175

Glu His Leu Lys Thr Leu Glu Gln Asn Val Glu Leu Ala Ala Ala Glu
            180                 185                 190

Leu Lys Ala Asp Glu Lys Ser His Ala Val Ile Leu Gly Asp Thr Arg
        195                 200                 205

Tyr Gly Ser Glu Glu Lys Gly Thr Tyr His Leu Ala Leu Phe Gly Asp
    210                 215                 220

Arg Ala Gln Glu Ile Ala Gly Ser Ala Thr Val Lys Ile Gly Glu Lys
225                 230                 235                 240

Val His Glu Ile Gly Ile Ala Gly Lys Gln
                245                 250

<210> SEQ ID NO 18
<211> LENGTH: 776
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Met Gly Pro Asp Ser Asp Arg Leu Gln Gln Arg Arg Val Ala Asp
1               5                   10                  15

Ile Gly Ala Gly Leu Ala Asp Ala Leu Thr Ala Pro Leu Asp His Lys
            20                  25                  30

Asp Lys Ser Leu Gln Ser Leu Thr Leu Asp Gln Ser Val Arg Lys Asn
        35                  40                  45

Glu Lys Leu Lys Leu Ala Ala Gln Gly Ala Glu Lys Thr Tyr Gly Asn
    50                  55                  60

```
Gly Asp Ser Leu Asn Thr Gly Lys Leu Lys Asn Asp Lys Val Ser Arg
65                  70                  75                  80

Phe Asp Phe Ile Arg Gln Ile Glu Val Asp Gly Gln Leu Ile Thr Leu
                85                  90                  95

Glu Ser Gly Glu Phe Gln Ile Tyr Lys Gln Asp His Ser Ala Val Val
                100                 105                 110

Ala Leu Gln Ile Glu Lys Ile Asn Asn Pro Asp Lys Ile Asp Ser Leu
                115                 120                 125

Ile Asn Gln Arg Ser Phe Leu Val Ser Gly Leu Gly Gly Glu His Thr
130                 135                 140

Ala Phe Asn Gln Leu Pro Asp Gly Lys Ala Glu Tyr His Gly Lys Ala
145                 150                 155                 160

Phe Ser Ser Asp Asp Ala Gly Gly Lys Leu Thr Tyr Thr Ile Asp Phe
                165                 170                 175

Ala Ala Lys Gln Gly His Gly Lys Ile Glu His Leu Lys Thr Pro Glu
                180                 185                 190

Gln Asn Val Glu Leu Ala Ala Ala Glu Leu Lys Ala Asp Glu Lys Ser
                195                 200                 205

His Ala Val Ile Leu Gly Asp Thr Arg Tyr Gly Ser Glu Glu Lys Gly
210                 215                 220

Thr Tyr His Leu Ala Leu Phe Gly Asp Arg Ala Gln Glu Ile Ala Gly
225                 230                 235                 240

Ser Ala Thr Val Lys Ile Gly Glu Lys Val His Glu Ile Gly Ile Ala
                245                 250                 255

Gly Lys Gln Gly Ser Gly Pro Asp Ser Asp Arg Leu Gln Arg Arg
                260                 265                 270

Val Ala Ala Asp Ile Gly Thr Gly Leu Ala Asp Ala Leu Thr Ala Pro
                275                 280                 285

Leu Asp His Lys Asp Lys Gly Leu Lys Ser Leu Thr Leu Glu Asp Ser
                290                 295                 300

Ile Pro Gln Asn Gly Thr Leu Thr Leu Ser Ala Gln Gly Ala Glu Lys
305                 310                 315                 320

Thr Phe Lys Ala Gly Asp Lys Asp Asn Ser Leu Asn Thr Gly Lys Leu
                325                 330                 335

Lys Asn Asp Lys Ile Ser Arg Phe Asp Phe Val Gln Lys Ile Glu Val
                340                 345                 350

Asp Gly Gln Thr Ile Thr Leu Ala Ser Gly Glu Phe Gln Ile Tyr Lys
                355                 360                 365

Gln Asn His Ser Ala Val Val Ala Leu Gln Ile Glu Lys Ile Asn Asn
                370                 375                 380

Pro Asp Lys Thr Asp Ser Leu Ile Asn Gln Arg Ser Phe Leu Val Ser
385                 390                 395                 400

Gly Leu Gly Gly Glu His Thr Ala Phe Asn Gln Leu Pro Gly Gly Lys
                405                 410                 415

Ala Glu Tyr His Gly Lys Ala Phe Ser Ser Asp Pro Asn Gly Arg
                420                 425                 430

Leu His Tyr Ser Ile Asp Phe Thr Lys Lys Gln Gly Tyr Gly Arg Ile
                435                 440                 445

Glu His Leu Lys Thr Leu Glu Gln Asn Val Glu Leu Ala Ala Ala Glu
                450                 455                 460

Leu Lys Ala Asp Glu Lys Ser His Ala Val Ile Leu Gly Asp Thr Arg
465                 470                 475                 480
```

```
Tyr Gly Ser Glu Glu Lys Gly Thr Tyr His Leu Ala Leu Phe Gly Asp
                485                 490                 495

Arg Ala Gln Glu Ile Ala Gly Ser Ala Thr Val Lys Ile Gly Glu Lys
            500                 505                 510

Val His Glu Ile Gly Ile Ala Gly Lys Gln Gly Ser Gly Gly Gly Gly
        515                 520                 525

Val Ala Ala Asp Ile Gly Ala Gly Leu Ala Asp Ala Leu Thr Ala Pro
    530                 535                 540

Leu Asp His Lys Asp Lys Gly Leu Gln Ser Leu Thr Leu Asp Gln Ser
545                 550                 555                 560

Val Arg Lys Asn Glu Lys Leu Lys Leu Ala Ala Gln Gly Ala Glu Lys
                565                 570                 575

Thr Tyr Gly Asn Gly Asp Ser Leu Asn Thr Gly Lys Leu Lys Asn Asp
            580                 585                 590

Lys Val Ser Arg Phe Asp Phe Ile Arg Gln Ile Glu Val Asp Gly Gln
        595                 600                 605

Leu Ile Thr Leu Glu Ser Gly Glu Phe Gln Val Tyr Lys Gln Ser His
    610                 615                 620

Ser Ala Leu Thr Ala Phe Gln Thr Glu Gln Ile Gln Asp Ser Glu His
625                 630                 635                 640

Ser Gly Lys Met Val Ala Lys Arg Gln Phe Arg Ile Gly Asp Ile Ala
                645                 650                 655

Gly Glu His Thr Ser Phe Asp Lys Leu Pro Glu Gly Gly Arg Ala Thr
            660                 665                 670

Tyr Arg Gly Thr Ala Phe Gly Ser Asp Asp Ala Gly Lys Leu Thr
        675                 680                 685

Tyr Thr Ile Asp Phe Ala Ala Lys Gln Gly Asn Gly Lys Ile Glu His
    690                 695                 700

Leu Lys Ser Pro Glu Leu Asn Val Asp Leu Ala Ala Ala Asp Ile Lys
705                 710                 715                 720

Pro Asp Gly Lys Arg His Ala Val Ile Ser Gly Ser Val Leu Tyr Asn
                725                 730                 735

Gln Ala Glu Lys Gly Ser Tyr Ser Leu Gly Ile Phe Gly Gly Lys Ala
            740                 745                 750

Gln Glu Val Ala Gly Ser Ala Glu Val Lys Thr Val Asn Gly Ile Arg
        755                 760                 765

His Ile Gly Leu Ala Ala Lys Gln
    770                 775

<210> SEQ ID NO 19
<211> LENGTH: 273
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Met Asn Arg Thr Ala Phe Cys Cys Leu Ser Leu Thr Ala Ala Leu Ile
1               5                   10                  15

Leu Thr Ala Cys Ser Ser Gly Gly Gly Val Ala Ala Asp Ile Gly
            20                  25                  30

Ala Gly Leu Ala Asp Ala Leu Thr Ala Pro Leu Asp His Lys Asp Lys
        35                  40                  45

Ser Leu Gln Ser Leu Thr Leu Asp Gln Val Val Arg Lys Asn Glu Lys
```

```
            50                  55                  60
Leu Lys Leu Ala Ala Gln Gly Ala Glu Lys Thr Tyr Gly Asn Gly Asp
 65                  70                  75                  80

Ser Leu Asn Thr Gly Lys Leu Lys Asn Asp Lys Val Ser Arg Phe Asp
                 85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
        115                 120                 125

Gln Ile Glu Lys Ile Asn Asn Pro Asp Lys Ile Asp Ser Leu Ile Asn
130                 135                 140

Gln Arg Ser Phe Arg Val Ser Gly Leu Gly Gly Glu His Thr Ala Phe
145                 150                 155                 160

Asn Gln Leu Pro Asp Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
            180                 185                 190

Lys Gln Gly His Gly Lys Ile Glu His Leu Lys Thr Pro Glu Gln Asn
        195                 200                 205

Val Glu Leu Ala Ala Ala Glu Leu Lys Ala Asp Glu Lys Ser His Ala
210                 215                 220

Val Ile Leu Gly Asp Thr Arg Tyr Gly Ser Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Gly Glu Lys Val His Glu Ile Gly Ile Ala Gly Lys
            260                 265                 270

Gln

<210> SEQ ID NO 20
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Gly Ser Gly Gly Gly Gly
1               5

<210> SEQ ID NO 21
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Gly Pro Asp Ser Asp Arg Leu Gln Gln Arg Arg
1               5                   10

<210> SEQ ID NO 22
<211> LENGTH: 13
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 22

Gly Ser Gly Pro Asp Ser Asp Arg Leu Gln Gln Arg Arg
1               5                   10

<210> SEQ ID NO 23
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Gly Lys Gly Pro Asp Ser Asp Arg Leu Gln Gln Arg Arg
1               5                   10

<210> SEQ ID NO 24
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Met Gly Pro Asp Ser Asp Arg Leu Gln Gln Arg Arg
1               5                   10

<210> SEQ ID NO 25
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Met Ala Ser
1

<210> SEQ ID NO 26
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Leu Glu His His His His His His
1               5

<210> SEQ ID NO 27
<211> LENGTH: 769
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 27

```
Met Gly Pro Asp Ser Asp Arg Leu Gln Gln Arg Val Ala Ala Asp
1               5                   10                  15

Ile Gly Ala Gly Leu Ala Asp Ala Leu Thr Ala Pro Leu Asp His Lys
            20                  25                  30

Asp Lys Ser Leu Gln Ser Leu Thr Leu Asp Gln Val Val Arg Lys Asn
        35                  40                  45

Glu Lys Leu Lys Leu Ala Ala Gln Gly Ala Lys Thr Tyr Gly Asn
    50                  55                  60

Gly Asp Ser Leu Asn Thr Gly Lys Leu Lys Asn Asp Lys Val Ser Arg
65                  70                  75                  80

Phe Asp Phe Ile Arg Gln Ile Glu Val Asp Gly Gln Leu Ile Thr Leu
                85                  90                  95

Glu Ser Gly Glu Phe Gln Ile Tyr Lys Gln Asp His Ser Ala Val Val
                100                 105                 110

Ala Leu Gln Ile Glu Lys Ile Asn Asn Pro Asp Lys Ile Asp Ser Leu
            115                 120                 125

Ile Asn Gln Arg Ser Phe Arg Val Ser Gly Leu Gly Gly Glu His Thr
        130                 135                 140

Ala Phe Asn Gln Leu Pro Asp Gly Lys Ala Glu Tyr His Gly Lys Ala
145                 150                 155                 160

Phe Ser Ser Asp Asp Ala Gly Gly Lys Leu Thr Tyr Thr Ile Asp Phe
                165                 170                 175

Ala Ala Lys Gln Gly His Gly Lys Ile Glu His Leu Lys Thr Pro Glu
            180                 185                 190

Gln Asn Val Glu Leu Ala Ala Ala Glu Leu Lys Ala Asp Glu Lys Ser
        195                 200                 205

His Ala Val Ile Leu Gly Asp Thr Arg Tyr Gly Ser Glu Glu Lys Gly
    210                 215                 220

Thr Tyr His Leu Ala Leu Phe Gly Asp Arg Ala Gln Glu Ile Ala Gly
225                 230                 235                 240

Ser Ala Thr Val Lys Ile Gly Glu Lys Val His Ala Ile Gly Ile Ala
                245                 250                 255

Gly Lys Gln Gly Ser Gly Gly Gly Val Ala Ala Asp Ile Gly Thr
            260                 265                 270

Gly Leu Ala Asp Ala Leu Thr Ala Pro Leu Asp His Lys Asp Lys Gly
            275                 280                 285

Leu Lys Ser Leu Thr Leu Glu Asp Val Ile Pro Gln Asn Gly Thr Leu
    290                 295                 300

Thr Leu Ser Ala Gln Gly Ala Glu Lys Thr Phe Lys Ala Gly Asp Lys
305                 310                 315                 320

Asp Asn Ser Leu Asn Thr Gly Lys Leu Lys Asn Asp Lys Ile Ser Arg
                325                 330                 335

Phe Asp Phe Val Gln Lys Ile Glu Val Asp Gly Gln Thr Ile Thr Leu
                340                 345                 350

Ala Ser Gly Glu Phe Gln Ile Tyr Lys Gln Asn His Ser Ala Val Val
            355                 360                 365

Ala Leu Gln Ile Glu Lys Ile Asn Asn Pro Asp Lys Thr Asp Ser Leu
        370                 375                 380

Ile Asn Gln Arg Ser Phe Arg Val Ser Gly Leu Gly Gly Glu His Thr
385                 390                 395                 400

Ala Phe Asn Gln Leu Pro Gly Gly Lys Ala Glu Tyr His Gly Lys Ala
                405                 410                 415
```

```
Phe Ser Ser Asp Asp Pro Asn Gly Arg Leu His Tyr Ser Ile Asp Phe
                420                 425                 430

Thr Lys Lys Gln Gly Tyr Gly Arg Ile Glu His Leu Lys Thr Leu Glu
            435                 440                 445

Gln Asn Val Glu Leu Ala Ala Ala Glu Leu Lys Ala Asp Glu Lys Ser
        450                 455                 460

His Ala Val Ile Leu Gly Asp Thr Arg Tyr Gly Ser Glu Glu Lys Gly
465                 470                 475                 480

Thr Tyr His Leu Ala Leu Phe Gly Asp Arg Ala Gln Glu Ile Ala Gly
                485                 490                 495

Ser Ala Thr Val Lys Ile Gly Glu Lys Val His Ala Ile Gly Ile Ala
            500                 505                 510

Gly Lys Gln Gly Ser Gly Gly Gly Val Ala Ala Asp Ile Gly Ala
        515                 520                 525

Gly Leu Ala Asp Ala Leu Thr Ala Pro Leu Asp His Lys Asp Lys Gly
    530                 535                 540

Leu Gln Ser Leu Thr Leu Asp Gln Ser Val Ser Lys Asn Glu Lys Leu
545                 550                 555                 560

Lys Leu Ala Ala Gln Gly Ala Glu Lys Thr Tyr Gly Asn Gly Asp Ser
                565                 570                 575

Leu Asn Thr Gly Lys Leu Lys Asn Asp Lys Val Ser Arg Phe Asp Phe
            580                 585                 590

Ile Arg Gln Ile Glu Val Asp Gly Gln Leu Ile Thr Leu Glu Ser Gly
        595                 600                 605

Glu Phe Gln Val Tyr Lys Gln Ser His Ser Ala Leu Thr Ala Phe Gln
    610                 615                 620

Thr Glu Gln Ile Gln Asp Ser Glu His Ser Gly Lys Met Val Ala Lys
625                 630                 635                 640

Arg Gln Phe Arg Ile Gly Asp Ile Ala Gly Glu His Thr Ser Phe Asp
                645                 650                 655

Lys Leu Pro Glu Gly Gly Arg Ala Thr Tyr Arg Gly Thr Ala Phe Gly
            660                 665                 670

Ser Asp Asp Ala Gly Gly Lys Leu Thr Tyr Thr Ile Asp Phe Ala Ala
        675                 680                 685

Lys Gln Gly Asn Gly Lys Ile Glu His Leu Lys Ser Pro Glu Leu Asn
    690                 695                 700

Val Asp Leu Ala Ala Ala Asp Ile Lys Pro Asp Gly Lys Arg His Ala
705                 710                 715                 720

Val Ile Ser Gly Ser Val Leu Tyr Asn Gln Ala Glu Lys Gly Ser Tyr
                725                 730                 735

Ser Leu Gly Ile Phe Gly Gly Lys Ala Gln Glu Val Ala Gly Ser Ala
            740                 745                 750

Glu Val Lys Thr Val Asn Gly Ile Arg His Ile Gly Leu Ala Ala Lys
        755                 760                 765

Gln

<210> SEQ ID NO 28
<211> LENGTH: 757
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

```
<400> SEQUENCE: 28

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Val
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Arg Val Ser Gly Leu Gly
            115                 120                 125

Gly Glu His Thr Ala Phe Asn Gln Leu Pro Asp Gly Lys Ala Glu Tyr
        130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Ala
225                 230                 235                 240

Ile Gly Ile Ala Gly Lys Gln Gly Ser Gly Gly Gly Val Ala Ala
                245                 250                 255

Asp Ile Gly Thr Gly Leu Ala Asp Ala Leu Thr Ala Pro Leu Asp His
            260                 265                 270

Lys Asp Lys Gly Leu Lys Ser Leu Thr Leu Glu Asp Val Ile Pro Gln
        275                 280                 285

Asn Gly Thr Leu Thr Leu Ser Ala Gln Gly Ala Glu Lys Thr Phe Lys
    290                 295                 300

Ala Gly Asp Lys Asp Asn Ser Leu Asn Thr Gly Lys Leu Lys Asn Asp
305                 310                 315                 320

Lys Ile Ser Arg Phe Asp Phe Val Gln Lys Ile Glu Val Asp Gly Gln
                325                 330                 335

Thr Ile Thr Leu Ala Ser Gly Glu Phe Gln Ile Tyr Lys Gln Asn His
            340                 345                 350

Ser Ala Val Val Ala Leu Gln Ile Glu Lys Ile Asn Asn Pro Asp Lys
        355                 360                 365

Thr Asp Ser Leu Ile Asn Gln Arg Ser Phe Arg Val Ser Gly Leu Gly
    370                 375                 380

Gly Glu His Thr Ala Phe Asn Gln Leu Pro Gly Gly Lys Ala Glu Tyr
385                 390                 395                 400

His Gly Lys Ala Phe Ser Ser Asp Asp Pro Asn Gly Arg Leu His Tyr
                405                 410                 415
```

Ser Ile Asp Phe Thr Lys Lys Gln Gly Tyr Gly Arg Ile Glu His Leu
              420                 425                 430

Lys Thr Leu Glu Gln Asn Val Glu Leu Ala Ala Ala Glu Leu Lys Ala
          435                 440                 445

Asp Glu Lys Ser His Ala Val Ile Leu Gly Asp Thr Arg Tyr Gly Ser
450                 455                 460

Glu Glu Lys Gly Thr Tyr His Leu Ala Leu Phe Gly Asp Arg Ala Gln
465                 470                 475                 480

Glu Ile Ala Gly Ser Ala Thr Val Lys Ile Gly Lys Val His Ala
              485                 490                 495

Ile Gly Ile Ala Gly Lys Gln Gly Ser Gly Gly Gly Val Ala Ala
              500                 505                 510

Asp Ile Gly Ala Gly Leu Ala Asp Ala Leu Thr Ala Pro Leu Asp His
              515                 520                 525

Lys Asp Lys Gly Leu Gln Ser Leu Thr Leu Asp Gln Ser Val Ser Lys
530                 535                 540

Asn Glu Lys Leu Lys Leu Ala Ala Gln Gly Ala Glu Lys Thr Tyr Gly
545                 550                 555                 560

Asn Gly Asp Ser Leu Asn Thr Gly Lys Leu Lys Asn Asp Lys Val Ser
              565                 570                 575

Arg Phe Asp Phe Ile Arg Gln Ile Glu Val Asp Gly Gln Leu Ile Thr
              580                 585                 590

Leu Glu Ser Gly Glu Phe Gln Val Tyr Lys Gln Ser His Ser Ala Leu
              595                 600                 605

Thr Ala Phe Gln Thr Glu Gln Ile Gln Asp Ser Glu His Ser Gly Lys
              610                 615                 620

Met Val Ala Lys Arg Gln Phe Arg Ile Gly Asp Ile Ala Gly Glu His
625                 630                 635                 640

Thr Ser Phe Asp Lys Leu Pro Glu Gly Gly Arg Ala Thr Tyr Arg Gly
              645                 650                 655

Thr Ala Phe Gly Ser Asp Asp Ala Gly Gly Lys Leu Thr Tyr Thr Ile
              660                 665                 670

Asp Phe Ala Ala Lys Gln Gly Asn Gly Lys Ile Glu His Leu Lys Ser
              675                 680                 685

Pro Glu Leu Asn Val Asp Leu Ala Ala Ala Asp Ile Lys Pro Asp Gly
              690                 695                 700

Lys Arg His Ala Val Ile Ser Gly Ser Val Leu Tyr Asn Gln Ala Glu
705                 710                 715                 720

Lys Gly Ser Tyr Ser Leu Gly Ile Phe Gly Lys Ala Gln Glu Val
              725                 730                 735

Ala Gly Ser Ala Glu Val Lys Thr Val Asn Gly Ile Arg His Ile Gly
              740                 745                 750

Leu Ala Ala Lys Gln
        755

<210> SEQ ID NO 29
<211> LENGTH: 769
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

-continued

```
Met Gly Pro Asp Ser Asp Arg Leu Gln Gln Arg Val Ala Ala Asp
1               5                   10                  15

Ile Gly Ala Gly Leu Ala Asp Ala Leu Thr Ala Pro Leu Asp His Lys
            20                  25                  30

Asp Lys Ser Leu Gln Ser Leu Thr Leu Asp Gln Val Val Arg Lys Asn
            35                  40                  45

Glu Lys Leu Lys Leu Ala Ala Gln Gly Ala Glu Lys Thr Tyr Gly Asn
        50                  55                  60

Gly Asp Ser Leu Asn Thr Gly Lys Leu Lys Asn Asp Lys Val Ser Arg
65                  70                  75                  80

Phe Asp Phe Ile Arg Gln Ile Glu Val Asp Gly Gln Leu Ile Thr Leu
                85                  90                  95

Glu Ser Gly Glu Phe Gln Ile Tyr Lys Gln Asp His Ser Ala Val Val
                100                 105                 110

Ala Leu Gln Ile Glu Lys Ile Asn Asn Pro Asp Lys Ile Asp Ser Leu
            115                 120                 125

Ile Asn Gln Arg Ser Phe Arg Val Ser Gly Leu Gly Gly Glu His Thr
            130                 135                 140

Ala Phe Asn Gln Leu Pro Asp Gly Lys Ala Glu Tyr His Gly Lys Ala
145                 150                 155                 160

Phe Ser Ser Asp Asp Ala Gly Gly Lys Leu Thr Tyr Thr Ile Asp Phe
                165                 170                 175

Ala Ala Lys Gln Gly His Gly Lys Ile Glu His Leu Lys Thr Pro Glu
            180                 185                 190

Gln Asn Val Glu Leu Ala Ala Ala Glu Leu Lys Ala Asp Glu Lys Ser
            195                 200                 205

His Ala Val Ile Leu Gly Asp Thr Arg Tyr Gly Ser Glu Glu Lys Gly
    210                 215                 220

Thr Tyr His Leu Ala Leu Phe Gly Asp Arg Ala Gln Glu Ile Ala Gly
225                 230                 235                 240

Ser Ala Thr Val Lys Ile Gly Glu Lys Val His Glu Ile Gly Ile Ala
                245                 250                 255

Gly Lys Gln Gly Ser Gly Gly Gly Val Ala Ala Asp Ile Gly Thr
            260                 265                 270

Gly Leu Ala Asp Ala Leu Thr Ala Pro Leu Asp His Lys Asp Lys Gly
            275                 280                 285

Leu Lys Ser Leu Thr Leu Glu Asp Val Ile Pro Gln Asn Gly Thr Leu
            290                 295                 300

Thr Leu Ser Ala Gln Gly Ala Glu Lys Thr Phe Lys Ala Gly Asp Lys
305                 310                 315                 320

Asp Asn Ser Leu Asn Thr Gly Lys Leu Lys Asn Asp Lys Ile Ser Arg
            325                 330                 335

Phe Asp Phe Val Gln Lys Ile Glu Val Asp Gly Gln Thr Ile Thr Leu
            340                 345                 350

Ala Ser Gly Glu Phe Gln Ile Tyr Lys Gln Asn His Ser Ala Val Val
            355                 360                 365

Ala Leu Gln Ile Glu Lys Ile Asn Asn Pro Asp Lys Thr Asp Ser Leu
            370                 375                 380

Ile Asn Gln Arg Ser Phe Arg Val Ser Gly Leu Gly Gly Glu His Thr
385                 390                 395                 400

Ala Phe Asn Gln Leu Pro Gly Gly Lys Ala Glu Tyr His Gly Lys Ala
            405                 410                 415

Phe Ser Ser Asp Asp Pro Asn Gly Arg Leu His Tyr Ser Ile Asp Phe
```

```
                420             425             430
Thr Lys Lys Gln Gly Tyr Gly Arg Ile Glu His Leu Lys Thr Leu Glu
            435                 440                 445

Gln Asn Val Glu Leu Ala Ala Glu Leu Lys Ala Asp Glu Lys Ser
450                 455                 460

His Ala Val Ile Leu Gly Asp Thr Arg Tyr Gly Ser Glu Glu Lys Gly
465                 470                 475                 480

Thr Tyr His Leu Ala Leu Phe Gly Asp Arg Ala Gln Glu Ile Ala Gly
            485                 490                 495

Ser Ala Thr Val Lys Ile Gly Glu Lys Val His Glu Ile Gly Ile Ala
            500                 505                 510

Gly Lys Gln Gly Ser Gly Gly Gly Val Ala Ala Asp Ile Gly Ala
            515                 520                 525

Gly Leu Ala Asp Ala Leu Thr Ala Pro Leu Asp His Lys Asp Lys Gly
            530                 535                 540

Leu Gln Ser Leu Thr Leu Asp Gln Ser Val Ser Lys Asn Glu Lys Leu
545                 550                 555                 560

Lys Leu Ala Ala Gln Gly Ala Glu Lys Thr Tyr Gly Asn Gly Asp Ser
            565                 570                 575

Leu Asn Thr Gly Lys Leu Lys Asn Asp Lys Val Ser Arg Phe Asp Phe
            580                 585                 590

Ile Arg Gln Ile Glu Val Asp Gly Gln Leu Ile Thr Leu Glu Ser Gly
            595                 600                 605

Glu Phe Gln Val Tyr Lys Gln Ser His Ser Ala Leu Thr Ala Phe Gln
            610                 615                 620

Thr Glu Gln Ile Gln Asp Ser Glu His Ser Gly Lys Met Val Ala Lys
625                 630                 635                 640

Arg Gln Phe Arg Ile Gly Asp Ile Ala Gly Glu His Thr Ser Phe Asp
            645                 650                 655

Lys Leu Pro Glu Gly Gly Arg Ala Thr Tyr Arg Gly Thr Ala Phe Gly
            660                 665                 670

Ser Asp Asp Ala Gly Gly Lys Leu Thr Tyr Thr Ile Asp Phe Ala Ala
            675                 680                 685

Lys Gln Gly Asn Gly Lys Ile Glu His Leu Lys Ser Pro Glu Leu Asn
            690                 695                 700

Val Asp Leu Ala Ala Ala Asp Ile Lys Pro Asp Gly Lys Arg His Ala
705                 710                 715                 720

Val Ile Ser Gly Ser Val Leu Tyr Asn Gln Ala Glu Lys Gly Ser Tyr
            725                 730                 735

Ser Leu Gly Ile Phe Gly Gly Lys Ala Gln Glu Val Ala Gly Ser Ala
            740                 745                 750

Glu Val Lys Thr Val Asn Gly Ile Arg His Ile Gly Leu Ala Ala Lys
            755                 760                 765

Gln
```

<210> SEQ ID NO 30
<211> LENGTH: 757
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 30

```
Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Val
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Arg Val Ser Gly Leu Gly
            115                 120                 125

Gly Glu His Thr Ala Phe Asn Gln Leu Pro Asp Gly Lys Ala Glu Tyr
        130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Glu
225                 230                 235                 240

Ile Gly Ile Ala Gly Lys Gln Gly Ser Gly Gly Gly Val Ala Ala
                245                 250                 255

Asp Ile Gly Thr Gly Leu Ala Asp Ala Leu Thr Ala Pro Leu Asp His
            260                 265                 270

Lys Asp Lys Gly Leu Lys Ser Leu Thr Leu Glu Asp Val Ile Pro Gln
        275                 280                 285

Asn Gly Thr Leu Thr Leu Ser Ala Gln Gly Ala Glu Lys Thr Phe Lys
    290                 295                 300

Ala Gly Asp Lys Asp Asn Ser Leu Asn Thr Gly Lys Leu Lys Asn Asp
305                 310                 315                 320

Lys Ile Ser Arg Phe Asp Phe Val Gln Lys Ile Glu Val Asp Gly Gln
                325                 330                 335

Thr Ile Thr Leu Ala Ser Gly Glu Phe Gln Ile Tyr Lys Gln Asn His
            340                 345                 350

Ser Ala Val Val Ala Leu Gln Ile Glu Lys Ile Asn Asn Pro Asp Lys
        355                 360                 365

Thr Asp Ser Leu Ile Asn Gln Arg Ser Phe Arg Val Ser Gly Leu Gly
    370                 375                 380

Gly Glu His Thr Ala Phe Asn Gln Leu Pro Gly Gly Lys Ala Glu Tyr
385                 390                 395                 400

His Gly Lys Ala Phe Ser Ser Asp Asp Pro Asn Gly Arg Leu His Tyr
                405                 410                 415

Ser Ile Asp Phe Thr Lys Lys Gln Gly Tyr Gly Arg Ile Glu His Leu
```

```
            420                 425                 430
Lys Thr Leu Glu Gln Asn Val Glu Leu Ala Ala Glu Leu Lys Ala
        435                 440                 445
Asp Glu Lys Ser His Ala Val Ile Leu Gly Asp Thr Arg Tyr Gly Ser
    450                 455                 460
Glu Glu Lys Gly Thr Tyr His Leu Ala Leu Phe Gly Asp Arg Ala Gln
465                 470                 475                 480
Glu Ile Ala Gly Ser Ala Thr Val Lys Ile Gly Glu Lys Val His Glu
                485                 490                 495
Ile Gly Ile Ala Gly Lys Gln Gly Ser Gly Gly Gly Val Ala Ala
                500                 505                 510
Asp Ile Gly Ala Gly Leu Ala Asp Ala Leu Thr Ala Pro Leu Asp His
            515                 520                 525
Lys Asp Lys Gly Leu Gln Ser Leu Thr Leu Asp Gln Ser Val Ser Lys
        530                 535                 540
Asn Glu Lys Leu Lys Leu Ala Ala Gln Gly Ala Glu Lys Thr Tyr Gly
545                 550                 555                 560
Asn Gly Asp Ser Leu Asn Thr Gly Lys Leu Lys Asn Asp Lys Val Ser
                565                 570                 575
Arg Phe Asp Phe Ile Arg Gln Ile Glu Val Asp Gly Gln Leu Ile Thr
            580                 585                 590
Leu Glu Ser Gly Glu Phe Gln Val Tyr Lys Gln Ser His Ser Ala Leu
        595                 600                 605
Thr Ala Phe Gln Thr Glu Gln Ile Gln Asp Ser Glu His Ser Gly Lys
    610                 615                 620
Met Val Ala Lys Arg Gln Phe Arg Ile Gly Asp Ile Ala Gly Glu His
625                 630                 635                 640
Thr Ser Phe Asp Lys Leu Pro Glu Gly Gly Arg Ala Thr Tyr Arg Gly
                645                 650                 655
Thr Ala Phe Gly Ser Asp Asp Ala Gly Gly Lys Leu Thr Tyr Thr Ile
            660                 665                 670
Asp Phe Ala Ala Lys Gln Gly Asn Gly Lys Ile Glu His Leu Lys Ser
        675                 680                 685
Pro Glu Leu Asn Val Asp Leu Ala Ala Asp Ile Lys Pro Asp Gly
    690                 695                 700
Lys Arg His Ala Val Ile Ser Gly Ser Val Leu Tyr Asn Gln Ala Glu
705                 710                 715                 720
Lys Gly Ser Tyr Ser Leu Gly Ile Phe Gly Gly Lys Ala Gln Glu Val
                725                 730                 735
Ala Gly Ser Ala Glu Val Lys Thr Val Asn Gly Ile Arg His Ile Gly
            740                 745                 750
Leu Ala Ala Lys Gln
        755

<210> SEQ ID NO 31
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (32)..(32)
<223> OTHER INFORMATION: Any amino acid
<220> FEATURE:
```

```
<221> NAME/KEY: MOD_RES
<222> LOCATION: (123)..(123)
<223> OTHER INFORMATION: Any amino acid except Leu

<400> SEQUENCE: 31
```

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Xaa
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Xaa Val Ser Gly Leu Gly
        115                 120                 125

Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Glu
225                 230                 235                 240

Ile Gly Ile Ala Gly Lys Gln
                245

```
<210> SEQ ID NO 32
<211> LENGTH: 250
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (32)..(32)
<223> OTHER INFORMATION: Any amino acid
<220> FEATURE:
<221> NAME/KEY: MOD_RES
<222> LOCATION: (126)..(126)
<223> OTHER INFORMATION: Any amino acid except Leu

<400> SEQUENCE: 32
```

Val Ala Ala Asp Ile Gly Thr Gly Leu Ala Asp Ala Leu Thr Ala Pro
1               5                   10                  15

Leu Asp His Lys Asp Lys Gly Leu Lys Ser Leu Thr Leu Glu Asp Xaa
            20                  25                  30

Ile Pro Gln Asn Gly Thr Leu Thr Leu Ser Ala Gln Gly Ala Glu Lys
                35                  40                  45

Thr Phe Lys Ala Gly Asp Lys Asp Asn Ser Leu Asn Thr Gly Lys Leu
 50                  55                  60

Lys Asn Asp Lys Ile Ser Arg Phe Asp Phe Val Gln Lys Ile Glu Val
65                  70                  75                  80

Asp Gly Gln Thr Ile Thr Leu Ala Ser Gly Glu Phe Gln Ile Tyr Lys
                85                  90                  95

Gln Asn His Ser Ala Val Val Ala Leu Gln Ile Glu Lys Ile Asn Asn
            100                 105                 110

Pro Asp Lys Thr Asp Ser Leu Ile Asn Gln Arg Ser Phe Xaa Val Ser
            115                 120                 125

Gly Leu Gly Gly Glu His Thr Ala Phe Asn Gln Leu Pro Gly Gly Lys
        130                 135                 140

Ala Glu Tyr His Gly Lys Ala Phe Ser Ser Asp Asp Pro Asn Gly Arg
145                 150                 155                 160

Leu His Tyr Ser Ile Asp Phe Thr Lys Lys Gln Gly Tyr Gly Arg Ile
                165                 170                 175

Glu His Leu Lys Thr Leu Glu Gln Asn Val Glu Leu Ala Ala Ala Glu
            180                 185                 190

Leu Lys Ala Asp Glu Lys Ser His Ala Val Ile Leu Gly Asp Thr Arg
        195                 200                 205

Tyr Gly Ser Glu Glu Lys Gly Thr Tyr His Leu Ala Leu Phe Gly Asp
210                 215                 220

Arg Ala Gln Glu Ile Ala Gly Ser Ala Thr Val Lys Ile Gly Glu Lys
225                 230                 235                 240

Val His Glu Ile Gly Ile Ala Gly Lys Gln
                245                 250

<210> SEQ ID NO 33
<211> LENGTH: 273
<212> TYPE: PRT
<213> ORGANISM: Neisseria meningitidis

<400> SEQUENCE: 33

Met Asn Arg Thr Ala Phe Cys Cys Leu Ser Leu Thr Thr Ala Leu Ile
1               5                   10                  15

Leu Thr Ala Cys Ser Ser Gly Gly Gly Gly Val Ala Ala Asp Ile Gly
                20                  25                  30

Ala Arg Leu Ala Asp Ala Leu Thr Ala Pro Leu Asp His Lys Asp Lys
                35                  40                  45

Ser Leu Gln Ser Leu Thr Leu Asp Gln Ser Val Arg Lys Asn Glu Lys
 50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Ile Tyr Lys Gln Asp His Ser Ala Val Val Ala Leu
            115                 120                 125

Gln Ile Glu Lys Ile Asn Asn Pro Asp Lys Ile Asp Ser Leu Ile Asn
        130                 135                 140

Gln Arg Ser Phe Leu Val Ser Gly Leu Gly Gly Glu His Thr Ala Phe

```
                145                 150                 155                 160
Asn Gln Leu Pro Asp Gly Lys Ala Glu Tyr His Gly Lys Ala Phe Ser
                165                 170                 175

Ser Asp Asp Ala Gly Gly Lys Leu Thr Tyr Thr Ile Asp Phe Ala Ala
                180                 185                 190

Lys Gln Gly His Gly Lys Ile Glu His Leu Lys Thr Pro Glu Gln Asn
                195                 200                 205

Val Glu Leu Ala Ala Ala Glu Leu Lys Ala Asp Glu Lys Ser His Ala
                210                 215                 220

Val Ile Leu Gly Asp Thr Arg Tyr Gly Ser Glu Glu Lys Gly Thr Tyr
225                 230                 235                 240

His Leu Ala Leu Phe Gly Asp Arg Ala Gln Glu Ile Ala Gly Ser Ala
                245                 250                 255

Thr Val Lys Ile Gly Glu Lys Val His Glu Ile Gly Ile Ala Gly Lys
                260                 265                 270

Gln

<210> SEQ ID NO 34
<211> LENGTH: 247
<212> TYPE: PRT
<213> ORGANISM: Neisseria meningitidis

<400> SEQUENCE: 34

Val Ala Ala Asp Ile Gly Ala Arg Leu Ala Asp Ala Leu Thr Ala Pro
1                   5                  10                  15

Leu Asp His Lys Asp Lys Ser Leu Gln Ser Leu Thr Leu Asp Gln Ser
                20                  25                  30

Val Arg Lys Asn Glu Lys Leu Lys Leu Ala Ala Gln Gly Ala Glu Lys
                35                  40                  45

Thr Tyr Gly Asn Gly Asp Ser Leu Asn Thr Gly Lys Leu Lys Asn Asp
                50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
                100                 105                 110

Ile Asp Ser Leu Ile Asn Gln Arg Ser Phe Leu Val Ser Gly Leu Gly
                115                 120                 125

Gly Glu His Thr Ala Phe Asn Gln Leu Pro Asp Gly Lys Ala Glu Tyr
                130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
                180                 185                 190

Asp Glu Lys Ser His Ala Val Ile Leu Gly Asp Thr Arg Tyr Gly Ser
                195                 200                 205

Glu Glu Lys Gly Thr Tyr His Leu Ala Leu Phe Gly Asp Arg Ala Gln
                210                 215                 220

Glu Ile Ala Gly Ser Ala Thr Val Lys Ile Gly Glu Lys Val His Glu
225                 230                 235                 240

Ile Gly Ile Ala Gly Lys Gln
```

<210> SEQ ID NO 35
<211> LENGTH: 247
<212> TYPE: PRT
<213> ORGANISM: Neisseria meningitidis

<400> SEQUENCE: 35

```
Val Ala Ala Asp Ile Gly Ala Arg Leu Ala Asp Ala Leu Thr Ala Pro
1               5                   10                  15

Leu Asp His Lys Asp Lys Ser Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Leu Val Ser Gly Leu Gly
        115                 120                 125

Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Glu
225                 230                 235                 240

Ile Gly Ile Ala Gly Lys Gln
                245
```

<210> SEQ ID NO 36
<211> LENGTH: 248
<212> TYPE: PRT
<213> ORGANISM: Neisseria meningitidis

<400> SEQUENCE: 36

```
Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Lys
```

```
        65                  70                  75                  80
Leu Ile Thr Leu Glu Ser Gly Glu Phe Gln Val Tyr Lys Gln Ser His
                85                  90                  95

Ser Ala Leu Thr Ala Leu Gln Thr Glu Gln Val Gln Asp Ser Glu Asp
            100                 105                 110

Ser Gly Lys Met Val Ala Lys Arg Gln Phe Arg Ile Gly Asp Ile Ala
            115                 120                 125

Gly Glu His Thr Ser Phe Asp Lys Leu Pro Lys Gly Gly Ser Ala Thr
            130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly His Gly Lys Ile Glu His
                165                 170                 175

Leu Lys Ser Pro Glu Leu Asn Val Glu Leu Ala Thr Ala Glu Leu Lys
                180                 185                 190

Ala Asp Glu Lys Ser His Ala Val Ile Leu Gly Asp Thr Arg Tyr Gly
                195                 200                 205

Gly Glu Glu Lys Gly Thr Tyr His Leu Ala Leu Phe Gly Asp Arg Ala
            210                 215                 220

Gln Glu Ile Ala Gly Ser Ala Thr Val Lys Ile Arg Glu Lys Val His
225                 230                 235                 240

Glu Ile Gly Ile Ala Gly Lys Gln
                245

<210> SEQ ID NO 37
<211> LENGTH: 250
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (32)..(32)
<223> OTHER INFORMATION: Any amino acid except Ser
<220> FEATURE:
<221> NAME/KEY: MOD_RES
<222> LOCATION: (126)..(126)
<223> OTHER INFORMATION: Any amino acid except Leu

<400> SEQUENCE: 37

Val Ala Ala Asp Ile Gly Thr Gly Leu Ala Asp Ala Leu Thr Ala Pro
1               5                   10                  15

Leu Asp His Lys Asp Lys Gly Leu Lys Ser Leu Thr Leu Glu Asp Xaa
                20                  25                  30

Ile Pro Gln Asn Gly Thr Leu Thr Leu Ser Ala Gln Gly Ala Glu Lys
                35                  40                  45

Thr Phe Lys Ala Gly Asp Lys Asp Asn Ser Leu Asn Thr Gly Lys Leu
50                  55                  60

Lys Asn Asp Lys Ile Ser Arg Phe Asp Phe Val Gln Lys Ile Glu Val
65                  70                  75                  80

Asp Gly Gln Thr Ile Thr Leu Ala Ser Gly Glu Phe Gln Ile Tyr Lys
                85                  90                  95

Gln Asn His Ser Ala Val Val Ala Leu Gln Ile Glu Lys Ile Asn Asn
            100                 105                 110

Pro Asp Lys Thr Asp Ser Leu Ile Asn Gln Arg Ser Phe Xaa Val Ser
            115                 120                 125
```

```
Gly Leu Gly Gly Glu His Thr Ala Phe Asn Gln Leu Pro Gly Gly Lys
            130                 135                 140

Ala Glu Tyr His Gly Lys Ala Phe Ser Ser Asp Asp Pro Asn Gly Arg
145                 150                 155                 160

Leu His Tyr Ser Ile Asp Phe Thr Lys Lys Gln Gly Tyr Gly Arg Ile
                165                 170                 175

Glu His Leu Lys Thr Leu Glu Gln Asn Val Glu Leu Ala Ala Ala Glu
            180                 185                 190

Leu Lys Ala Asp Glu Lys Ser His Ala Val Ile Leu Gly Asp Thr Arg
        195                 200                 205

Tyr Gly Ser Glu Glu Lys Gly Thr Tyr His Leu Ala Leu Phe Gly Asp
210                 215                 220

Arg Ala Gln Glu Ile Ala Gly Ser Ala Thr Val Lys Ile Gly Glu Lys
225                 230                 235                 240

Val His Glu Ile Gly Ile Ala Gly Lys Gln
                245                 250

<210> SEQ ID NO 38
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (32)..(32)
<223> OTHER INFORMATION: Any amino acid except Ser
<220> FEATURE:
<221> NAME/KEY: MOD_RES
<222> LOCATION: (123)..(123)
<223> OTHER INFORMATION: Any amino acid except Leu
<220> FEATURE:
<221> NAME/KEY: MOD_RES
<222> LOCATION: (240)..(240)
<223> OTHER INFORMATION: Any amino acid except Glu

<400> SEQUENCE: 38

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Xaa
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
            85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Xaa Val Ser Gly Leu Gly
            115                 120                 125

Gly Glu His Thr Ala Phe Asn Gln Leu Pro Asp Gly Lys Ala Glu Tyr
            130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
```

```
                    165                 170                 175
Lys Thr Pro Glu Gln Asn Val Glu Leu Ala Ala Ala Glu Leu Lys Ala
                180                 185                 190

Asp Glu Lys Ser His Ala Val Ile Leu Gly Asp Thr Arg Tyr Gly Ser
            195                 200                 205

Glu Glu Lys Gly Thr Tyr His Leu Ala Leu Phe Gly Asp Arg Ala Gln
        210                 215                 220

Glu Ile Ala Gly Ser Ala Thr Val Lys Ile Gly Glu Lys Val His Xaa
225                 230                 235                 240

Ile Gly Ile Ala Gly Lys Gln
                245

<210> SEQ ID NO 39
<211> LENGTH: 262
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (32)..(32)
<223> OTHER INFORMATION: Any amino acid except Ser
<220> FEATURE:
<221> NAME/KEY: MOD_RES
<222> LOCATION: (123)..(123)
<223> OTHER INFORMATION: Any amino acid except Leu
<220> FEATURE:
<221> NAME/KEY: MOD_RES
<222> LOCATION: (240)..(240)
<223> OTHER INFORMATION: Any amino acid except Glu

<400> SEQUENCE: 39

Cys Ser Ser Gly Gly Gly Ser Gly Gly Gly Val Ala Ala Asp
1               5                   10                  15

Ile Gly Thr Gly Leu Ala Asp Ala Leu Thr Ala Pro Leu Asp His Xaa
            20                  25                  30

Asp Lys Gly Leu Lys Ser Leu Thr Leu Glu Asp Ser Ile Pro Gln Asn
        35                  40                  45

Gly Thr Leu Thr Leu Ser Ala Gln Gly Ala Glu Lys Thr Phe Lys Ala
    50                  55                  60

Gly Asp Lys Asp Asn Ser Leu Asn Thr Gly Lys Leu Lys Asn Asp Lys
65                  70                  75                  80

Ile Ser Arg Phe Asp Phe Val Gln Lys Ile Glu Val Asp Gly Gln Thr
                85                  90                  95

Ile Thr Leu Ala Ser Gly Glu Phe Gln Ile Tyr Lys Gln Asn His Ser
            100                 105                 110

Ala Val Val Ala Leu Gln Ile Glu Lys Ile Xaa Asn Pro Asp Lys Thr
        115                 120                 125

Asp Ser Leu Ile Asn Gln Arg Ser Phe Leu Val Ser Gly Leu Gly Gly
    130                 135                 140

Glu His Thr Ala Phe Asn Gln Leu Pro Gly Gly Lys Ala Glu Tyr His
145                 150                 155                 160

Gly Lys Ala Phe Ser Ser Asp Asp Pro Asn Gly Arg Leu His Tyr Ser
                165                 170                 175

Ile Asp Phe Thr Lys Lys Gln Gly Tyr Gly Arg Ile Glu His Leu Lys
            180                 185                 190

Thr Leu Glu Gln Asn Val Glu Leu Ala Ala Ala Glu Leu Lys Ala Asp
        195                 200                 205
```

```
Glu Lys Ser His Ala Val Ile Leu Gly Asp Thr Arg Tyr Gly Ser Glu
    210                 215                 220

Glu Lys Gly Thr Tyr His Leu Ala Leu Phe Gly Asp Arg Ala Gln Xaa
225                 230                 235                 240

Ile Ala Gly Ser Ala Thr Val Lys Ile Gly Glu Lys Val His Glu Ile
                245                 250                 255

Gly Ile Ala Gly Lys Gln
            260

<210> SEQ ID NO 40
<211> LENGTH: 262
<212> TYPE: PRT
<213> ORGANISM: Neisseria meningitidis

<400> SEQUENCE: 40

Cys Ser Ser Gly Gly Gly Ser Gly Gly Gly Val Ala Ala Asp
1               5                   10                  15

Ile Gly Thr Gly Leu Ala Asp Ala Leu Thr Ala Pro Leu Asp His Lys
                20                  25                  30

Asp Lys Gly Leu Lys Ser Leu Thr Leu Glu Asp Ser Ile Pro Gln Asn
            35                  40                  45

Gly Thr Leu Thr Leu Ser Ala Gln Gly Ala Glu Lys Thr Phe Lys Ala
50                  55                  60

Gly Asp Lys Asp Asn Ser Leu Asn Thr Gly Lys Leu Lys Asn Asp Lys
65                  70                  75                  80

Ile Ser Arg Phe Asp Phe Val Gln Lys Ile Glu Val Asp Gly Gln Thr
                85                  90                  95

Ile Thr Leu Ala Ser Gly Glu Phe Gln Ile Tyr Lys Gln Asn His Ser
            100                 105                 110

Ala Val Val Ala Leu Gln Ile Glu Lys Ile Asn Asn Pro Asp Lys Thr
        115                 120                 125

Asp Ser Leu Ile Asn Gln Arg Ser Phe Leu Val Ser Gly Leu Gly Gly
    130                 135                 140

Glu His Thr Ala Phe Asn Gln Leu Pro Gly Gly Lys Ala Glu Tyr His
145                 150                 155                 160

Gly Lys Ala Phe Ser Ser Asp Asp Pro Asn Gly Arg Leu His Tyr Ser
                165                 170                 175

Ile Asp Phe Thr Lys Lys Gln Gly Tyr Gly Arg Ile Glu His Leu Lys
            180                 185                 190

Thr Leu Glu Gln Asn Val Glu Leu Ala Ala Ala Glu Leu Lys Ala Asp
        195                 200                 205

Glu Lys Ser His Ala Val Ile Leu Gly Asp Thr Arg Tyr Gly Ser Glu
    210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                245                 250                 255

Gly Ile Ala Gly Lys Gln
            260

<210> SEQ ID NO 41
<211> LENGTH: 250
<212> TYPE: PRT
<213> ORGANISM: Artificial Sequence
<220> FEATURE:
<221> NAME/KEY: source
```

<223> OTHER INFORMATION: /note="Description of Artificial Sequence:
Synthetic polypeptide"

<400> SEQUENCE: 41

Val Ala Ala Asp Ile Gly Thr Gly Leu Ala Asp Ala Leu Thr Ala Pro
1               5                   10                  15

Leu Asp His Lys Asp Lys Gly Leu Lys Ser Leu Thr Leu Glu Asp Ser
            20                  25                  30

Ile Pro Gln Asn Gly Thr Leu Thr Leu Ser Ala Gln Gly Ala Glu Lys
        35                  40                  45

Thr Phe Lys Ala Gly Asp Lys Asp Asn Ser Leu Asn Thr Gly Lys Leu
    50                  55                  60

Lys Asn Asp Lys Ile Ser Arg Phe Asp Phe Val Gln Lys Ile Glu Val
65                  70                  75                  80

Asp Gly Gln Thr Ile Thr Leu Ala Ser Gly Glu Phe Gln Ile Tyr Lys
                85                  90                  95

Gln Asn His Ser Ala Val Val Ala Leu Gln Ile Glu Lys Ile Asn Asn
            100                 105                 110

Pro Asp Lys Thr Asp Ser Leu Ile Asn Gln Arg Ser Phe Leu Val Ser
        115                 120                 125

Gly Leu Gly Gly Glu His Thr Ala Phe Asn Gln Leu Pro Gly Gly Lys
    130                 135                 140

Ala Glu Tyr His Gly Lys Ala Phe Ser Ser Asp Asp Pro Asn Gly Arg
145                 150                 155                 160

Leu His Tyr Ser Ile Asp Phe Thr Lys Lys Gln Gly Tyr Gly Arg Ile
                165                 170                 175

Glu His Leu Lys Thr Leu Glu Gln Asn Val Glu Leu Ala Ala Ala Glu
            180                 185                 190

Leu Lys Ala Asp Glu Lys Ser His Ala Val Ile Leu Gly Asp Thr Arg
        195                 200                 205

Tyr Gly Ser Glu Glu Lys Gly Thr Tyr His Leu Ala Leu Phe Gly Asp
    210                 215                 220

Arg Ala Gln Glu Ile Ala Gly Ser Ala Thr Val Lys Ile Gly Glu Lys
225                 230                 235                 240

Val His Ala Ile Gly Ile Ala Gly Lys Gln
                245                 250

<210> SEQ ID NO 42
<211> LENGTH: 250
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 42

Val Ala Ala Asp Ile Gly Thr Gly Leu Ala Asp Ala Leu Thr Ala Pro
1               5                   10                  15

Leu Asp His Lys Asp Lys Gly Leu Lys Ser Leu Thr Leu Glu Asp Val
            20                  25                  30

Ile Pro Gln Asn Gly Thr Leu Thr Leu Ser Ala Gln Gly Ala Glu Lys
        35                  40                  45

Thr Phe Lys Ala Gly Asp Lys Asp Asn Ser Leu Asn Thr Gly Lys Leu
    50                  55                  60

Lys Asn Asp Lys Ile Ser Arg Phe Asp Phe Val Gln Lys Ile Glu Val
65                  70                  75                  80

Asp Gly Gln Thr Ile Thr Leu Ala Ser Gly Glu Phe Gln Ile Tyr Lys
            85                  90                  95

Gln Asn His Ser Ala Val Val Ala Leu Gln Ile Glu Lys Ile Asn Asn
        100                 105                 110

Pro Asp Lys Thr Asp Ser Leu Ile Asn Gln Arg Ser Phe Leu Val Ser
        115                 120                 125

Gly Leu Gly Gly Glu His Thr Ala Phe Asn Gln Leu Pro Gly Gly Lys
    130                 135                 140

Ala Glu Tyr His Gly Lys Ala Phe Ser Ser Asp Asp Pro Asn Gly Arg
145                 150                 155                 160

Leu His Tyr Ser Ile Asp Phe Thr Lys Lys Gln Gly Tyr Gly Arg Ile
                165                 170                 175

Glu His Leu Lys Thr Leu Glu Gln Asn Val Glu Leu Ala Ala Ala Glu
            180                 185                 190

Leu Lys Ala Asp Glu Lys Ser His Ala Val Ile Leu Gly Asp Thr Arg
        195                 200                 205

Tyr Gly Ser Glu Glu Lys Gly Thr Tyr His Leu Ala Leu Phe Gly Asp
    210                 215                 220

Arg Ala Gln Glu Ile Ala Gly Ser Ala Thr Val Lys Ile Gly Glu Lys
225                 230                 235                 240

Val His Ala Ile Gly Ile Ala Gly Lys Gln
                245                 250

<210> SEQ ID NO 43
<211> LENGTH: 250
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Val Ala Ala Asp Ile Gly Thr Gly Leu Ala Asp Ala Leu Thr Ala Pro
1               5                   10                  15

Leu Asp His Lys Asp Lys Gly Leu Lys Ser Leu Thr Leu Glu Asp Val
            20                  25                  30

Ile Pro Gln Asn Gly Thr Leu Thr Leu Ser Ala Gln Gly Ala Glu Lys
        35                  40                  45

Thr Phe Lys Ala Gly Asp Lys Asp Asn Ser Leu Asn Thr Gly Lys Leu
    50                  55                  60

Lys Asn Asp Lys Ile Ser Arg Phe Asp Phe Val Gln Lys Ile Glu Val
65                  70                  75                  80

Asp Gly Gln Thr Ile Thr Leu Ala Ser Gly Glu Phe Gln Ile Tyr Lys
            85                  90                  95

Gln Asn His Ser Ala Val Val Ala Leu Gln Ile Glu Lys Ile Asn Asn
        100                 105                 110

Pro Asp Lys Thr Asp Ser Leu Ile Asn Gln Arg Ser Phe Arg Val Ser
        115                 120                 125

Gly Leu Gly Gly Glu His Thr Ala Phe Asn Gln Leu Pro Gly Gly Lys
    130                 135                 140

Ala Glu Tyr His Gly Lys Ala Phe Ser Ser Asp Asp Pro Asn Gly Arg
145                 150                 155                 160

Leu His Tyr Ser Ile Asp Phe Thr Lys Lys Gln Gly Tyr Gly Arg Ile
                165                 170                 175

```
Glu His Leu Lys Thr Leu Glu Gln Asn Val Glu Leu Ala Ala Ala Glu
            180                 185                 190

Leu Lys Ala Asp Glu Lys Ser His Ala Val Ile Leu Gly Asp Thr Arg
        195                 200                 205

Tyr Gly Ser Glu Glu Lys Gly Thr Tyr His Leu Ala Leu Phe Gly Asp
    210                 215                 220

Arg Ala Gln Glu Ile Ala Gly Ser Ala Thr Val Lys Ile Gly Glu Lys
225                 230                 235                 240

Val His Ala Ile Gly Ile Ala Gly Lys Gln
                245                 250

<210> SEQ ID NO 44
<211> LENGTH: 250
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Val Ala Ala Asp Ile Gly Thr Gly Leu Ala Asp Ala Leu Thr Ala Pro
1               5                   10                  15

Leu Asp His Lys Asp Lys Gly Leu Lys Ser Leu Thr Leu Glu Asp Val
            20                  25                  30

Ile Pro Gln Asn Gly Thr Leu Thr Leu Ser Ala Gln Gly Ala Glu Lys
        35                  40                  45

Thr Phe Lys Ala Gly Asp Lys Asp Asn Ser Leu Asn Thr Gly Lys Leu
    50                  55                  60

Lys Asn Asp Lys Ile Ser Arg Phe Asp Phe Val Gln Lys Ile Glu Val
65                  70                  75                  80

Asp Gly Gln Thr Ile Thr Leu Ala Ser Gly Glu Phe Gln Ile Tyr Lys
            85                  90                  95

Gln Asn His Ser Ala Val Val Ala Leu Gln Ile Glu Lys Ile Asn Asn
            100                 105                 110

Pro Asp Lys Thr Asp Ser Leu Ile Asn Gln Arg Ser Phe Arg Val Ser
        115                 120                 125

Gly Leu Gly Gly Glu His Thr Ala Phe Asn Gln Leu Pro Gly Gly Lys
    130                 135                 140

Ala Glu Tyr His Gly Lys Ala Phe Ser Ser Asp Asp Pro Asn Gly Arg
145                 150                 155                 160

Leu His Tyr Ser Ile Asp Phe Thr Lys Lys Gln Gly Tyr Gly Arg Ile
            165                 170                 175

Glu His Leu Lys Thr Leu Glu Gln Asn Val Glu Leu Ala Ala Ala Glu
            180                 185                 190

Leu Lys Ala Asp Glu Lys Ser His Ala Val Ile Leu Gly Asp Thr Arg
        195                 200                 205

Tyr Gly Ser Glu Glu Lys Gly Thr Tyr His Leu Ala Leu Phe Gly Asp
    210                 215                 220

Arg Ala Gln Glu Ile Ala Gly Ser Ala Thr Val Lys Ile Gly Glu Lys
225                 230                 235                 240

Val His Glu Ile Gly Ile Ala Gly Lys Gln
                245                 250

<210> SEQ ID NO 45
<211> LENGTH: 247
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 45

```
Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Val
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Arg Val Ser Gly Leu Gly
        115                 120                 125

Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Glu
225                 230                 235                 240

Ile Gly Ile Ala Gly Lys Gln
                245
```

<210> SEQ ID NO 46
<211> LENGTH: 255
<212> TYPE: PRT
<213> ORGANISM: Neisseria meningitidis

<400> SEQUENCE: 46

```
Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80
```

```
Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255

<210> SEQ ID NO 47
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (32)..(32)
<223> OTHER INFORMATION: Any amino acid
<220> FEATURE:
<221> NAME/KEY: MOD_RES
<222> LOCATION: (123)..(123)
<223> OTHER INFORMATION: Any amino acid except Leu
<220> FEATURE:
<221> NAME/KEY: MOD_RES
<222> LOCATION: (240)..(240)
<223> OTHER INFORMATION: Any amino acid except Glu

<400> SEQUENCE: 47

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Xaa
                20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
        50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Xaa Val Ser Gly Leu Gly
```

```
                    115                 120                 125
Gly Glu His Thr Ala Phe Asn Gln Leu Pro Asp Gly Lys Ala Glu Tyr
    130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
    210                 215                 220

Glu Ile Ala Gly Ser Ala Thr Val Lys Ile Gly Glu Lys Val His Xaa
225                 230                 235                 240

Ile Gly Ile Ala Gly Lys Gln
                245

<210> SEQ ID NO 48
<211> LENGTH: 250
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (32)..(32)
<223> OTHER INFORMATION: Any amino acid
<220> FEATURE:
<221> NAME/KEY: MOD_RES
<222> LOCATION: (126)..(126)
<223> OTHER INFORMATION: Any amino acid except Leu
<220> FEATURE:
<221> NAME/KEY: MOD_RES
<222> LOCATION: (243)..(243)
<223> OTHER INFORMATION: Any amino acid except Glu

<400> SEQUENCE: 48

Val Ala Ala Asp Ile Gly Thr Gly Leu Ala Asp Ala Leu Thr Ala Pro
1               5                   10                  15

Leu Asp His Lys Asp Lys Gly Leu Lys Ser Leu Thr Leu Glu Asp Xaa
                20                  25                  30

Ile Pro Gln Asn Gly Thr Leu Thr Leu Ser Ala Gln Gly Ala Glu Lys
            35                  40                  45

Thr Phe Lys Ala Gly Asp Lys Asp Asn Ser Leu Asn Thr Gly Lys Leu
50                  55                  60

Lys Asn Asp Lys Ile Ser Arg Phe Asp Phe Val Gln Lys Ile Glu Val
65                  70                  75                  80

Asp Gly Gln Thr Ile Thr Leu Ala Ser Gly Glu Phe Gln Ile Tyr Lys
                85                  90                  95

Gln Asn His Ser Ala Val Val Ala Leu Gln Ile Glu Lys Ile Asn Asn
            100                 105                 110

Pro Asp Lys Thr Asp Ser Leu Ile Asn Gln Arg Ser Phe Xaa Val Ser
        115                 120                 125

Gly Leu Gly Gly Glu His Thr Ala Phe Asn Gln Leu Pro Gly Gly Lys
    130                 135                 140

Ala Glu Tyr His Gly Lys Ala Phe Ser Ser Asp Asp Pro Asn Gly Arg
145                 150                 155                 160
```

```
Leu His Tyr Ser Ile Asp Phe Thr Lys Lys Gln Gly Tyr Gly Arg Ile
            165                 170                 175

Glu His Leu Lys Thr Leu Glu Gln Asn Val Glu Leu Ala Ala Ala Glu
        180                 185                 190

Leu Lys Ala Asp Glu Lys Ser His Ala Val Ile Leu Gly Asp Thr Arg
    195                 200                 205

Tyr Gly Ser Glu Glu Lys Gly Thr Tyr His Leu Ala Leu Phe Gly Asp
210                 215                 220

Arg Ala Gln Glu Ile Ala Gly Ser Ala Thr Val Lys Ile Gly Glu Lys
225                 230                 235                 240

Val His Xaa Ile Gly Ile Ala Gly Lys Gln
            245                 250

<210> SEQ ID NO 49
<211> LENGTH: 248
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (34)..(34)
<223> OTHER INFORMATION: Any amino acid except Arg

<400> SEQUENCE: 49

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Xaa Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
            85                  90                  95

Ser Ala Leu Thr Ala Phe Gln Thr Glu Gln Ile Gln Asp Ser Glu His
        100                 105                 110

Ser Gly Lys Met Val Ala Lys Arg Gln Phe Arg Ile Gly Asp Ile Ala
    115                 120                 125

Gly Glu His Thr Ser Phe Asp Lys Leu Pro Glu Gly Gly Arg Ala Thr
130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
            165                 170                 175

Leu Lys Ser Pro Glu Leu Asn Val Asp Leu Ala Ala Ala Asp Ile Lys
        180                 185                 190

Pro Asp Gly Lys Arg His Ala Val Ile Ser Gly Ser Val Leu Tyr Asn
    195                 200                 205

Gln Ala Glu Lys Gly Ser Tyr Ser Leu Gly Ile Phe Gly Gly Lys Ala
210                 215                 220

Gln Glu Val Ala Gly Ser Ala Glu Val Lys Thr Val Asn Gly Ile Arg
225                 230                 235                 240
```

His Ile Gly Leu Ala Ala Lys Gln
                245

<210> SEQ ID NO 50
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Val
                20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
        50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
                100                 105                 110

Ile Asp Ser Leu Ile Asn Gln Arg Ser Phe Arg Val Ser Gly Leu Gly
            115                 120                 125

Gly Glu His Thr Ala Phe Asn Gln Leu Pro Asp Gly Lys Ala Glu Tyr
        130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
                180                 185                 190

Asp Glu Lys Ser His Ala Val Ile Leu Gly Asp Thr Arg Tyr Gly Ser
            195                 200                 205

Glu Glu Lys Gly Thr Tyr His Leu Ala Leu Phe Gly Asp Arg Ala Gln
        210                 215                 220

Glu Ile Ala Gly Ser Ala Thr Val Lys Ile Gly Glu Lys Val His Ala
225                 230                 235                 240

Ile Gly Ile Ala Gly Lys Gln
                245

<210> SEQ ID NO 51
<211> LENGTH: 250
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Val Ala Ala Asp Ile Gly Thr Gly Leu Ala Asp Ala Leu Thr Ala Pro
1               5                   10                  15

```
Leu Asp His Lys Asp Lys Gly Leu Lys Ser Leu Thr Leu Glu Asp Val
            20                  25                  30

Ile Pro Gln Asn Gly Thr Leu Thr Leu Ser Ala Gln Gly Ala Glu Lys
            35                  40                  45

Thr Phe Lys Ala Gly Asp Lys Asp Asn Ser Leu Asn Thr Gly Lys Leu
        50                  55                  60

Lys Asn Asp Lys Ile Ser Arg Phe Asp Phe Val Gln Lys Ile Glu Val
65                  70                  75                  80

Asp Gly Gln Thr Ile Thr Leu Ala Ser Gly Glu Phe Gln Ile Tyr Lys
                85                  90                  95

Gln Asn His Ser Ala Val Val Ala Leu Gln Ile Glu Lys Ile Asn Asn
            100                 105                 110

Pro Asp Lys Thr Asp Ser Leu Ile Asn Gln Arg Ser Phe Arg Val Ser
        115                 120                 125

Gly Leu Gly Gly Glu His Thr Ala Phe Asn Gln Leu Pro Gly Gly Lys
    130                 135                 140

Ala Glu Tyr His Gly Lys Ala Phe Ser Ser Asp Asp Pro Asn Gly Arg
145                 150                 155                 160

Leu His Tyr Ser Ile Asp Phe Thr Lys Lys Gln Gly Tyr Gly Arg Ile
                165                 170                 175

Glu His Leu Lys Thr Leu Glu Gln Asn Val Glu Leu Ala Ala Ala Glu
            180                 185                 190

Leu Lys Ala Asp Glu Lys Ser His Ala Val Ile Leu Gly Asp Thr Arg
        195                 200                 205

Tyr Gly Ser Glu Glu Lys Gly Thr Tyr His Leu Ala Leu Phe Gly Asp
    210                 215                 220

Arg Ala Gln Glu Ile Ala Gly Ser Ala Thr Val Lys Ile Gly Glu Lys
225                 230                 235                 240

Val His Ala Ile Gly Ile Ala Gly Lys Gln
                245                 250

<210> SEQ ID NO 52
<211> LENGTH: 248
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Ser Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
```

```
                115                 120                 125
Gly Glu His Thr Ser Phe Asp Lys Leu Pro Glu Gly Arg Ala Thr
            130                 135                 140
Tyr Arg Gly Thr Ala Phe Gly Ser Asp Asp Ala Gly Gly Lys Leu Thr
145                 150                 155                 160
Tyr Thr Ile Asp Phe Ala Ala Lys Gln Gly Asn Gly Lys Ile Glu His
                165                 170                 175
Leu Lys Ser Pro Glu Leu Asn Val Asp Leu Ala Ala Asp Ile Lys
            180                 185                 190
Pro Asp Gly Lys Arg His Ala Val Ile Ser Gly Ser Val Leu Tyr Asn
            195                 200                 205
Gln Ala Glu Lys Gly Ser Tyr Ser Leu Gly Ile Phe Gly Gly Lys Ala
        210                 215                 220
Gln Glu Val Ala Gly Ser Ala Glu Val Lys Thr Val Asn Gly Ile Arg
225                 230                 235                 240
His Ile Gly Leu Ala Ala Lys Gln
                245

<210> SEQ ID NO 53
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Val Ala Ala Asp Ile Gly Ala Gly Leu Ala Asp Ala Leu Thr Ala Pro
1               5                   10                  15
Leu Asp His Lys Asp Lys Ser Leu Gln Ser Leu Thr Leu Asp Gln Ser
            20                  25                  30
Val Arg Lys Asn Glu Lys Leu Lys Leu Ala Ala Gln Gly Ala Glu Lys
        35                  40                  45
Thr Tyr Gly Asn Gly Asp Ser Leu Asn Thr Gly Lys Leu Lys Asn Asp
50                  55                  60
Lys Val Ser Arg Phe Asp Phe Ile Arg Gln Ile Glu Val Asp Gly Gln
65                  70                  75                  80
Leu Ile Thr Leu Glu Ser Gly Glu Phe Gln Ile Tyr Lys Gln Asp His
                85                  90                  95
Ser Ala Val Val Ala Leu Gln Ile Glu Lys Ile Asn Asn Pro Asp Lys
            100                 105                 110
Ile Asp Ser Leu Ile Asn Gln Arg Ser Phe Arg Val Ser Gly Leu Gly
        115                 120                 125
Gly Glu His Thr Ala Phe Asn Gln Leu Pro Asp Gly Lys Ala Glu Tyr
            130                 135                 140
His Gly Lys Ala Phe Ser Ser Asp Asp Ala Gly Gly Lys Leu Thr Tyr
145                 150                 155                 160
Thr Ile Asp Phe Ala Ala Lys Gln Gly His Gly Lys Ile Glu His Leu
                165                 170                 175
Lys Thr Pro Glu Gln Asn Val Glu Leu Ala Ala Ala Glu Leu Lys Ala
            180                 185                 190
Asp Glu Lys Ser His Ala Val Ile Leu Gly Asp Thr Arg Tyr Gly Ser
        195                 200                 205
Glu Glu Lys Gly Thr Tyr His Leu Ala Leu Phe Gly Asp Arg Ala Gln
            210                 215                 220
```

```
Glu Ile Ala Gly Ser Ala Thr Val Lys Ile Gly Glu Lys Val His Ala
225                 230                 235                 240

Ile Gly Ile Ala Gly Lys Gln
            245
```

<210> SEQ ID NO 54
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

```
Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Ser
                20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
            100                 105                 110

Ile Asp Ser Leu Ile Asn Gln Arg Ser Phe Arg Val Ser Gly Leu Gly
        115                 120                 125

Gly Glu His Thr Ala Phe Asn Gln Leu Pro Asp Gly Lys Ala Glu Tyr
130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
            180                 185                 190

Asp Glu Lys Ser His Ala Val Ile Leu Gly Asp Thr Arg Tyr Gly Ser
        195                 200                 205

Glu Glu Lys Gly Thr Tyr His Leu Ala Leu Phe Gly Asp Arg Ala Gln
210                 215                 220

Glu Ile Ala Gly Ser Ala Thr Val Lys Ile Gly Glu Lys Val His Glu
225                 230                 235                 240

Ile Gly Ile Ala Gly Lys Gln
            245
```

<210> SEQ ID NO 55
<211> LENGTH: 250
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Val Ala Ala Asp Ile Gly Thr Gly Leu Ala Asp Ala Leu Thr Ala Pro
1               5                   10                  15

Leu Asp His Lys Asp Lys Gly Leu Lys Ser Leu Thr Leu Glu Asp Ser
                20                  25                  30

Ile Pro Gln Asn Gly Thr Leu Thr Leu Ser Ala Gln Gly Ala Glu Lys
            35                  40                  45

Thr Phe Lys Ala Gly Asp Lys Asp Asn Ser Leu Asn Thr Gly Lys Leu
        50                  55                  60

Lys Asn Asp Lys Ile Ser Arg Phe Asp Phe Val Gln Lys Ile Glu Val
65                  70                  75                  80

Asp Gly Gln Thr Ile Thr Leu Ala Ser Gly Glu Phe Gln Ile Tyr Lys
                85                  90                  95

Gln Asn His Ser Ala Val Val Ala Leu Gln Ile Glu Lys Ile Asn Asn
                100                 105                 110

Pro Asp Lys Thr Asp Ser Leu Ile Asn Gln Arg Ser Phe Arg Val Ser
            115                 120                 125

Gly Leu Gly Gly Glu His Thr Ala Phe Asn Gln Leu Pro Gly Gly Lys
    130                 135                 140

Ala Glu Tyr His Gly Lys Ala Phe Ser Ser Asp Asp Pro Asn Gly Arg
145                 150                 155                 160

Leu His Tyr Ser Ile Asp Phe Thr Lys Lys Gln Gly Tyr Gly Arg Ile
                165                 170                 175

Glu His Leu Lys Thr Leu Glu Gln Asn Val Glu Leu Ala Ala Ala Glu
                180                 185                 190

Leu Lys Ala Asp Glu Lys Ser His Ala Val Ile Leu Gly Asp Thr Arg
    195                 200                 205

Tyr Gly Ser Glu Glu Lys Gly Thr Tyr His Leu Ala Leu Phe Gly Asp
210                 215                 220

Arg Ala Gln Glu Ile Ala Gly Ser Ala Thr Val Lys Ile Gly Glu Lys
225                 230                 235                 240

Val His Ala Ile Gly Ile Ala Gly Lys Gln
                245                 250

<210> SEQ ID NO 56
<211> LENGTH: 250
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Val Ala Ala Asp Ile Gly Thr Gly Leu Ala Asp Ala Leu Thr Ala Pro
1               5                   10                  15

Leu Asp His Lys Asp Lys Gly Leu Lys Ser Leu Thr Leu Glu Asp Ser
                20                  25                  30

Ile Pro Gln Asn Gly Thr Leu Thr Leu Ser Ala Gln Gly Ala Glu Lys
            35                  40                  45

Thr Phe Lys Ala Gly Asp Lys Asp Asn Ser Leu Asn Thr Gly Lys Leu
        50                  55                  60

Lys Asn Asp Lys Ile Ser Arg Phe Asp Phe Val Gln Lys Ile Glu Val
65                  70                  75                  80

Asp Gly Gln Thr Ile Thr Leu Ala Ser Gly Glu Phe Gln Ile Tyr Lys
                85                  90                  95

Gln Asn His Ser Ala Val Val Ala Leu Gln Ile Glu Lys Ile Asn Asn

```
                    100                 105                 110
Pro Asp Lys Thr Asp Ser Leu Ile Asn Gln Arg Ser Phe Arg Val Ser
            115                 120                 125

Gly Leu Gly Gly Glu His Thr Ala Phe Asn Gln Leu Pro Gly Gly Lys
        130                 135                 140

Ala Glu Tyr His Gly Lys Ala Phe Ser Ser Asp Pro Asn Gly Arg
145                 150                 155                 160

Leu His Tyr Ser Ile Asp Phe Thr Lys Lys Gln Gly Tyr Gly Arg Ile
                165                 170                 175

Glu His Leu Lys Thr Leu Glu Gln Asn Val Glu Leu Ala Ala Ala Glu
                180                 185                 190

Leu Lys Ala Asp Glu Lys Ser His Ala Val Ile Leu Gly Asp Thr Arg
            195                 200                 205

Tyr Gly Ser Glu Glu Lys Gly Thr Tyr His Leu Ala Leu Phe Gly Asp
        210                 215                 220

Arg Ala Gln Glu Ile Ala Gly Ser Ala Thr Val Lys Ile Gly Glu Lys
225                 230                 235                 240

Val His Glu Ile Gly Ile Ala Gly Lys Gln
                245                 250

<210> SEQ ID NO 57
<211> LENGTH: 250
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (32)..(32)
<223> OTHER INFORMATION: Any amino acid except Ser
<220> FEATURE:
<221> NAME/KEY: MOD_RES
<222> LOCATION: (126)..(126)
<223> OTHER INFORMATION: Any amino acid except Leu
<220> FEATURE:
<221> NAME/KEY: MOD_RES
<222> LOCATION: (243)..(243)
<223> OTHER INFORMATION: Any amino acid except Glu

<400> SEQUENCE: 57

Val Ala Ala Asp Ile Gly Thr Gly Leu Ala Asp Ala Leu Thr Ala Pro
1               5                   10                  15

Leu Asp His Lys Asp Lys Gly Leu Lys Ser Leu Thr Leu Glu Asp Xaa
            20                  25                  30

Ile Pro Gln Asn Gly Thr Leu Thr Leu Ser Ala Gln Gly Ala Glu Lys
        35                  40                  45

Thr Phe Lys Ala Gly Asp Lys Asp Asn Ser Leu Asn Thr Gly Lys Leu
    50                  55                  60

Lys Asn Asp Lys Ile Ser Arg Phe Asp Phe Val Gln Lys Ile Glu Val
65                  70                  75                  80

Asp Gly Gln Thr Ile Thr Leu Ala Ser Gly Glu Phe Gln Ile Tyr Lys
                85                  90                  95

Gln Asn His Ser Ala Val Val Ala Leu Gln Ile Glu Lys Ile Asn Asn
            100                 105                 110

Pro Asp Lys Thr Asp Ser Leu Ile Asn Gln Arg Ser Phe Xaa Val Ser
        115                 120                 125

Gly Leu Gly Gly Glu His Thr Ala Phe Asn Gln Leu Pro Gly Gly Lys
    130                 135                 140
```

```
Ala Glu Tyr His Gly Lys Ala Phe Ser Ser Asp Asp Pro Asn Gly Arg
145                 150                 155                 160

Leu His Tyr Ser Ile Asp Phe Thr Lys Lys Gln Gly Tyr Gly Arg Ile
                165                 170                 175

Glu His Leu Lys Thr Leu Glu Gln Asn Val Glu Leu Ala Ala Ala Glu
            180                 185                 190

Leu Lys Ala Asp Glu Lys Ser His Ala Val Ile Leu Gly Asp Thr Arg
        195                 200                 205

Tyr Gly Ser Glu Glu Lys Gly Thr Tyr His Leu Ala Leu Phe Gly Asp
    210                 215                 220

Arg Ala Gln Glu Ile Ala Gly Ser Ala Thr Val Lys Ile Gly Glu Lys
225                 230                 235                 240

Val His Xaa Ile Gly Ile Ala Gly Lys Gln
                245                 250

<210> SEQ ID NO 58
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (3)..(10)
<223> OTHER INFORMATION: /replace=" "
<220> FEATURE:
<221> NAME/KEY: misc_feature
<222> LOCATION: (1)..(10)
<223> OTHER INFORMATION: /note="Variant residues given in the sequence
      have no preference with respect to those in the annotations
      for variant positions"

<400> SEQUENCE: 58

Gly Gly Gly Gly Gly Gly Gly Gly Gly Gly
1               5                   10

<210> SEQ ID NO 59
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (3)..(10)
<223> OTHER INFORMATION: /replace=" "
<220> FEATURE:
<221> NAME/KEY: misc_feature
<222> LOCATION: (1)..(10)
<223> OTHER INFORMATION: /note="Variant residues given in the sequence
      have no preference with respect to those in the annotations
      for variant positions"

<400> SEQUENCE: 59

His His His His His His His His His His
1               5                   10

<210> SEQ ID NO 60
<211> LENGTH: 10
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"
<220> FEATURE:
<221> NAME/KEY: VARIANT
<222> LOCATION: (4)..(10)
<223> OTHER INFORMATION: /replace=" "
<220> FEATURE:
<221> NAME/KEY: misc_feature
<222> LOCATION: (1)..(10)
<223> OTHER INFORMATION: /note="Variant residues given in the sequence
      have no preference with respect to those in the annotations
      for variant positions"

<400> SEQUENCE: 60

His His His His His His His His His His
1               5                   10
```

MODIFIED MENINGOCOCCAL FHBP POLYPEPTIDES

CROSS-REFERENCE TO RELATED APPLICATIONS

This is the U.S. National Stage application submitted under 35 U.S.C. § 371 for International Application No. PCT/EP2015/066228, filed Jul. 16, 2015, which claims priority to non-provisional Application No. EP 14177564.3, filed in the European Patent Office Jul. 17, 2014, all of which are incorporated herein by reference in their entireties.

INCORPORATION-BY-REFERENCE OF SEQUENCE LISTING OR TABLE

The content of the sequence listing submitted electronically via EFS-WEB in International Application No. PCT/EP2015/066228, filed Jul. 16, 2015, is incorporated herein by reference in its entirety.

TECHNICAL FIELD

This invention is in the field of protein engineering, relating in particular to the meningococcal factor H binding protein (fHbp), which is known to be a useful vaccine immunogen.

BACKGROUND

*Neisseria meningitidis* is a Gram-negative encapsulated bacterium which colonises the upper respiratory tract of approximately 10% of human population. Conjugate vaccines are available against serogroups A, C, W135 and Y, but the only vaccine which is available for protecting against serogroup B in general is the BEXSERO™ product which was approved in 2013.

One of the protective immunogens in BEXSERO™ is fHbp, which has also been known as protein '741' (SEQ ID NO: 2536 in ref. 1; SEQ ID 1 herein), 'NMB1870', 'GNA1870' [2-4, 'P2086', 'LP2086' or 'ORF2086' [5-7]. The 3D structure of this protein is known [8,9], and the protein has two β-barrels connected by a short linker. Many publications have reported on the protective efficacy of this protein in meningococcal vaccines e.g. see references 10-14. The fHbp lipoprotein is expressed in various strains across all serogroups. fHbp sequences have been grouped into three variants [2] (referred to herein as v1, v2 and v3), and it has been found in general that serum raised against a given variant is bactericidal against strains which express that variant, but is not active against strains which express one of the other two variants i.e. there is intra-variant cross-protection, but not inter-variant cross-protection (except for some v2 and v3 cross-reactivity).

To increase inter-family cross-reactivity the fHbp sequence has been engineered to contain specificities for all three variants [15]. Protein engineering has also been used to remove fHbp's interaction with siderophores [16] and with human factor H [17-25]. Disruption of the interaction with fH has been reported for all three variants and is postulated to provide a superior vaccine immunogen [22, 26]. For v2 polypeptides, however, references 23 and 24 report an inherent instability which is also seen in mutants with disrupted fH-binding. The instability appears to arise from the N-terminal β-barrel domain, and reference 23 warns that any substitutions in this barrel might promote instability. Mutations which aim to improve the stability of v2 sequences are disclosed in reference 27.

It is an object of the invention to provide fHbp v2 and v3 mutants having enhanced properties.

SUMMARY OF THE INVENTION

In one aspect, the present invention provides a polypeptide comprising an amino acid sequence having at least 80% sequence identity to SEQ ID NO: 5,wherein the amino acid sequence differs from SEQ ID NO: 5 at residues 123 and 240 relative to SEQ ID NO:5, and the polypeptide can, after administration to a human, elicit antibodies which can recognise a polypeptide consisting of SEQ ID NO: 4.

Another aspect of the invention is a polypeptide comprising an amino acid sequence having at least 80% sequence identity to SEQ ID NO: 5, wherein the amino acid sequence differs from SEQ ID NO: 5 at residues 32, 123 and 240 relative to SEQ ID NO:5, and the polypeptide can, after administration to a human, elicit antibodies which can recognise a polypeptide consisting of SEQ ID NO: 4.

Another aspect of the invention is a polypeptide comprising an amino acid sequence having at least 80% sequence identity to SEQ ID NO: 17, wherein the amino acid sequence differs from SEQ ID NO: 17 at residues 126 and 243 relative to SEQ ID NO:17, and the polypeptide can, after administration to a human, elicit antibodies which can recognise a polypeptide consisting of SEQ ID NO: 40.

Another aspect of the invention is a polypeptide comprising an amino acid sequence having at least 80% sequence identity to SEQ ID NO: 17, wherein the amino acid sequence differs from SEQ ID NO: 17 at residues 32, 126 and 243 relative to SEQ ID NO:17, and the polypeptide can, after administration to a human, elicit antibodies which can recognise a polypeptide consisting of SEQ ID NO: 40.

Another aspect of the invention is a polypeptide comprising an amino acid sequence having at least 90% sequence identity to SEQ ID NO: 47, wherein relative to SEQ ID NO:47 residue 123 is not leucine and residue 240 is not glutamate; and wherein when administered to a human the polypeptide can elicit an antibody response that is bactericidal against a meningococcus which expresses a v2 fHbp.

Another aspect of the invention is a polypeptide comprising an amino acid sequence having at least 90% sequence identity to SEQ ID NO: 47, wherein relative to SEQ ID NO:47 residue 32 is not serine, residue 123 is not leucine and residue 240 is not glutamate; and wherein when administered to a human the polypeptide can elicit an antibody response that is bactericidal against a meningococcus which expresses a v2 fHbp.

Another aspect of the invention is a polypeptide comprising an amino acid sequence having at least 90% sequence identity to SEQ ID NO: 48 wherein relative to SEQ ID NO:48 residue 126 is not leucine and residue 243 is not glutamate; and wherein when administered to a human the polypeptide can elicit an antibody response that is bactericidal against a meningococcus which expresses a v3 fHbp.

Another aspect of the invention is a polypeptide comprising an amino acid sequence having at least 90% sequence identity to SEQ ID NO: 48 wherein relative to SEQ ID NO:48 residue 32 is not serine, residue 126 is not leucine and residue 243 is not glutamate; and wherein when administered to a human the polypeptide can elicit an antibody response that is bactericidal against a meningococcus which expresses a v3 fHbp.

Another aspect of the invention is fusion polypeptides which, when administered to a human, elicit an antibody response that is bactericidal against both a meningococcus expressing a v2 fHbp and a meningococcus expressing a v3 fHbp.

Another aspect of the invention is an immunogenic composition comprising a pharmaceutically acceptable carrier and a polypeptide or fusion polypeptide of the invention.

Another aspect of the invention is a method of raising an antibody response in a human, comprising administering to said human an immunogenic composition according to the invention.

BRIEF DESCRIPTION OF THE DRAWINGS

FIG. 8 compares stability of the 'wild-type' fusion (SEQ ID NO: 18) in comparison with the stabilised non-binding fusion (SEQ ID NO: 27) in *E. coli* extracts probed by Western blot.

DETAILED DESCRIPTION

Figure 1:
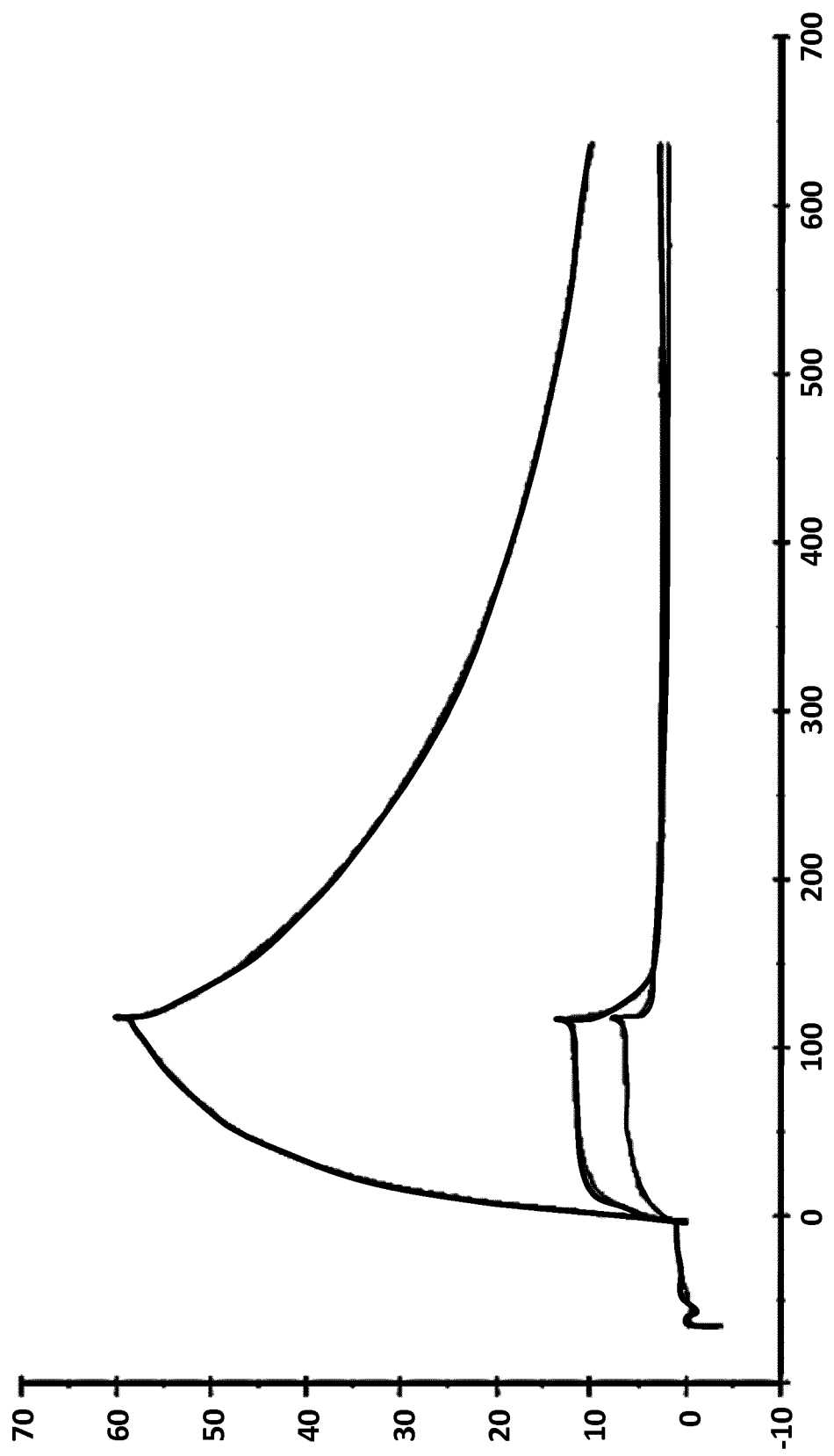
FIG. 1 shows the SPR response for wild-type v2 fHbp (top line), the E266 mutant of v2 (bottom line) and S58V/L149R mutant of v2 (middle line) binding to immobilised fH. The y-axis shows relative units, and the x-axis shows time (seconds, with 0 being sample injection).

Full-length fHbp from strain 2996 in v2 has the following amino acid sequence (SEQ ID NO: 2):

MNRTAFCCLSLTTAALILTACSSGGGGVAADIGAGLADALTAPLDHKDKSL

QSLTLDQSVRKNEKLKLAAQGAEKTYGNGDSLNTGKLKNDKVSRFDFIRQ

IEVDGQLITLESGEFQIYKQDHSAVVALQIEKINNPDKIDSLINQRSFLV

SGLGGEHTAFNQLPDGKAEYHGKAFSSDDAGGKLTYTIDFAAKQGHGKIE

HLKTPEQNVELAAAELKADEKSHAVILGDTRYGSEEKGTYHLALFGDRAQ

EIAGSATVKIGEKVHEIGIAGKQ

The mature lipoprotein lacks the first 19 amino acids of SEQ ID NO: 2 (underlined; provides SEQ ID NO: 4, beginning with Cys-20). It is also known to produce a 'ΔG' form of fHbp in which the N-terminus is truncated up to residue 26 (i.e. to remove the poly-glycine stretch, and beginning instead with Val-27), thus providing SEQ ID NO: 5.

Full-length fHbp from strain M1239 in v3 has the following amino acid sequence (SEQ ID NO: 3):

MNRTAFCCLSLTTALILTACSSGGGGSGGGGVAADIGTGLADALTAPLDH

KDKGLKSLTLEDSIPQNGTLTLSAQGAEKTFKAGDKDNSLNTGKLKNDKI

SREDEVQKIEVDGQTITLASGEFQIYKQNHSAVVALQIEKINNPDKTDSL

INQRSFLVSGLGGEHTAFNQLPGGKAEYHGKAFSSDDPNGRLHYSIDFTK

KQGYGRIEHLKTLEQNVELAAAELKADEKSHAVILGDTRYGSEEKGTYHL

ALFGDRAQEIAGSATVKIGEKVHEIGIAGKQ

The mature lipoprotein lacks the first 19 amino acids of SEQ ID NO: 3 (underlined; provides SEQ ID NO: 40), and the ΔG form of SEQ ID NO: 3 lacks the first 31 amino acids (SEQ ID NO: 17).

The inventors have studied two different types of mutation in v2 and v3. Firstly, they have identified residues within SEQ ID NO: 2 and SEQ ID NO: 3 which can be modified to increase the polypeptide's stability. Secondly, they have identified residues which decrease binding to human factor H (fH). The invention relates to mutant fHbp polypeptides comprising both types of mutation, thereby providing fHbp polypeptides with enhanced properties. Specifically, fHbp mutants that do not bind factor H but which retain immunogenicity are advantageous because the resultant antibody responses are directed towards epitopes in or near the fH-binding site. Following vaccination using wild-type fHbp vaccine antigens, such epitopes may be obscured by factor H binding.

The amino acids of most interest are as follows, numbered according to the full-length sequences (SEQ ID NOs: 1 & 3) and also according to the ΔG sequences (SEQ ID NOs: 5 & 17):

|  |  | Stability** |  | fH binding |
|---|---|---|---|---|
| v2 | SEQ ID NO: 1 | Ser-58 | Leu-149 | Glu-266 |
|  | SEQ ID NO: 5 | Ser-32 | Leu-123 | Glu-240 |
| v3 | SEQ ID NO: 3 | Ser-63 | Leu-157 | Glu-274 |
|  | SEQ ID NO: 17 | Ser-32 | Leu-126 | Glu-243 |

** Where only one of these residues is mutated, it is preferably the leucine

Mutant v2 fHbp

Thus in a first aspect, the invention provides a polypeptide comprising a mutant fHbp v2 amino acid sequence, wherein: (a) the amino acid sequence has at least k % sequence identity to SEQ ID NO: 5, and/or comprises a fragment of SEQ ID NO: 5; but (b) the amino acid sequence differs from SEQ ID NO: 5 at residues L123 and E240 (and, optionally, at residue S32) (numbering of amino acids is relative to SEQ ID NO:5).

Where feature (a) relates to a fragment, the fragment will include the two (or optionally three) residues listed in (b), but those residues will differ when compared to those positions in SEQ ID NO: 5. A mutant fHbp v2 amino acid sequence can have at least k % sequence identity to, and include several fragments of, SEQ ID NO: 5, wherein each such fragment is at least 7 amino acids long. These fragments will typically include at least one epitope from SEQ ID NO: 5. Epitope identification and mapping is established for fHbp [11; 28-32].

The value of k may be selected from 80, 85, 86, 87, 88, 89, 90, 91, 92, 93, 94, 95, 96, 97, 98, 99 or more. It is preferably 90 (i.e. the mutant fHbp v2 amino acid sequence has at least 90% identity to SEQ ID NO: 5) and is more preferably 95.

The polypeptide can, after administration to a suitable host animal (such as a mouse or human), elicit antibodies which can recognise a wild-type meningococcal polypeptide consisting of SEQ ID NO: 4. These antibodies will include some antibodies which do not recognise a v1 or a v3 polypeptide (e.g. will not recognise a wild-type meningococcal polypeptide consisting of SEQ ID NO: 46 and a wild-type meningococcal polypeptide consisting of SEQ ID NO: 40), although they may also include some antibodies which cross-react with v1 and/or v3 polypeptides. The antibodies are ideally bactericidal against a meningococcal strain which expresses a v2 fHbp e.g. against the M2091 strain (see below).

The polypeptide has, under the same experimental conditions, a higher stability than the same polypeptide but without the sequence differences of (b), e.g. higher stability than a wild-type meningococcal polypeptide consisting of SEQ ID NO: 4. The stability enhancement can be assessed using differential scanning calorimetry (DSC) e.g. as discussed in references 33 & 34. DSC has previously been used to assess the stability of v2 fHbp [24]. Suitable conditions for DSC to assess stability can use 20 μM of polypeptide in a buffered solution (e.g. 25 mM Tris) with a pH between 6 and 8 (e.g. 7-7.5) with 100-200 mM NaCl (e.g. 150 mM).

The increase in stability is ideally at least 5° C. e.g. at least 10° C., 15° C., 20° C., 25° C., 30° C., 35° C. or more. These temperatures refer to the increase in thermal transition midpoint (Tm) as assessed by DSC. Wild-type fHbp shows two DSC peaks during unfolding (one for the N-terminal domain and one for the C-terminal domain) and, where a polypeptide of the invention includes both such domains, the increase refers to the stability of the N-terminal domain, which can occur even below 40° C. with wild-type v2 sequences [24] (whereas C-terminal domains can have a Tm of 80° C. or more). Thus the mutant fHbp v2 amino acid sequence of the invention preferably has a N-terminal domain with a Tm of at least 45° C. e.g. ≥50° C., ≥55° C., ≥60° C., ≥65° C., ≥70° C., ≥75° C., or even ≥80° C.

In addition to this increased stability the polypeptide has, under the same experimental conditions, a lower affinity for human fH than the same polypeptide but without the sequence differences of (b), e.g. lower affinity than a wild-type meningococcal polypeptide consisting of SEQ ID NO: 4. The affinity disruption can be quantitatively assessed using surface plasmon resonance (SPR), e.g. as disclosed in references 18 and 21-24 with immobilised human fH. An affinity reduction (i.e. an increase in the dissociation constant, $K_D$) of at least 10-fold, and ideally at least 100-fold, is preferred.

In some embodiments, the polypeptide is truncated relative to SEQ ID NO: 5. Compared to the wild-type mature sequence, SEQ ID NO: 5 is already truncated at the N-terminus up to and including the poly-glycine sequence (compare SEQ ID NOs: 4 and 5), but SEQ ID NO: 5 can be truncated at the C-terminus and/or further truncated at the N-terminus.

Mutant v3 Mbp

In a second aspect, the invention provides a polypeptide comprising a mutant fHbp v3 amino acid sequence, wherein:

(a) the amino acid sequence has at least j % sequence identity to SEQ ID NO: 17, and/or comprises a fragment of SEQ ID NO: 17; but (b) the amino acid sequence differs from SEQ ID NO: 17 at residues L126 and E243 (and, optionally, at residue S32) (numbering of amino acids is relative to SEQ ID NO:17.

Where feature (a) relates to a fragment, the fragment will include the two (or optionally three) residues listed in (b), but those residues will differ when compared to those positions in SEQ ID NO: 17. A mutant fHbp v3 amino acid sequence can have at least j % sequence identity to and include several fragments of SEQ ID NO: 17, wherein each such fragment is at least 7 amino acids long. These fragments will typically include at least one epitope from SEQ ID NO: 17. Epitope identification and mapping is established for fHbp [11; 28-32].

The value of j may be selected from 80, 85, 86, 87, 88, 89, 90, 91, 92, 93, 94, 95, 96, 97, 98, 99 or more. It is preferably 90 (i.e. the mutant fHbp v3 amino acid sequence has at least 90% identity to SEQ ID NO: 17) and is more preferably 95.

The polypeptide can, after administration to a suitable host animal (such as a mouse or human), elicit antibodies which can recognise a wild-type meningococcal polypeptide consisting of SEQ ID NO: 40. These antibodies will include some antibodies which do not recognise a v1 or a v2 polypeptide (e.g. will not recognise a wild-type meningococcal polypeptide consisting of SEQ ID NO: 46 and a wild-type meningococcal polypeptide consisting of SEQ ID NO: 4), although they may also include some antibodies which cross-react with v1 and/or v2 polypeptides. The antibodies are ideally bactericidal against a meningococcal strain which expresses a v3 fHbp e.g. against the M01-240355 strain (see below).

The polypeptide has, under the same experimental conditions, a higher stability than the same polypeptide but without the sequence differences of (b), e.g. higher stability than a wild-type meningococcal polypeptide consisting of SEQ ID NO: 40. The stability enhancement can be assessed using differential scanning calorimetry (DSC) e.g. as discussed in references 33 & 34 DSC has previously been used to assess the stability of v3 fHbp [23]. Suitable conditions for DSC to assess stability can use 20 μM of polypeptide in a buffered solution (e.g. 25 mM Tris) with a pH between 6 and 8 (e.g. 7-7.5) with 100-200 mM NaCl (e.g. 150 mM).

The increase in stability is ideally at least 5° C. e.g. at least 10° C., 15° C., 20° C., 25° C., 30° C., 35° C. or more. These temperatures refer to the increase in thermal transition midpoint (Tm) as assessed by DSC. Wild-type fHbp shows two DSC peaks during unfolding (one for the N-terminal domain and one for the C-terminal domain) and, where a polypeptide of the invention includes both such domains, the increase refers to the stability of the N-terminal domain, which can occur at around 60° C. or less with wild-type v3 sequences [24] (whereas C-terminal domains can have a Tm of 80° C. or more). Thus the mutant fHbp v3 amino acid sequence of the invention preferably has a N-terminal domain with a Tm of at least 65° C. e.g. ≥70° C., ≥75° C., or even ≥80° C.

In addition to this increased stability the polypeptide has, under the same experimental conditions, a lower affinity for human fH than the same polypeptide but without the sequence differences of (b), e.g. lower affinity than a wild-type meningococcal polypeptide consisting of SEQ ID NO: 40. The affinity disruption can be quantitatively assessed using surface plasmon resonance (SPR), e.g. as disclosed in references 18 and 21-24 with immobilised human fH. An affinity reduction (i.e. an increase in the dissociation constant, $K_D$) of at least 10-fold, and ideally at least 100-fold, is preferred.

In some embodiments, the polypeptide is truncated relative to SEQ ID NO: 17. Compared to the wild-type mature sequence, SEQ ID NO: 17 is already truncated at the N-terminus up to and including the poly-glycine sequence (compare SEQ ID NOs: 40 and 17), but SEQ ID NO: 17 can be truncated at the C-terminus and/or further truncated at the N-terminus.

Mutations Relative to SEQ ID NO: 5

Polypeptides of the first aspect of the invention comprise an amino acid sequence which has at least k % identity to SEQ ID NO: 5, and/or comprise a fragment of SEQ ID NO: 5. In comparison to SEQ ID NO: 5, however, this amino sequence has a modification at least at amino acid residues L123 and E240 (and optionally also at residue S32). These residues are numbered according to SEQ ID NO: 5; to match the nascent wild-type sequence (SEQ ID NO: 2), the numbering should change +26 (i.e. Ser-32 of SEQ ID NO: 5 is Ser-58 of SEQ ID NO: 2), and to match the mature wild-type sequence (SEQ ID NO: 4) the numbering should change +7 (which also permits easy comparison with ref. 25).

The three specified residues can be deleted, but preferably they are substituted by a different amino acid. For example, Leu-123 can be substituted by any of the other 19 naturally-occurring amino acids. When a substitution is made, the replacement amino acid in some embodiments may be a simple amino acid such as glycine or alanine. In other instances, the replacement amino acid is a conservative substitution e.g. it is made within the following four groups: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparagine, glutamine, cysteine, serine, threonine, tyrosine. In other embodiments the substitution is non-conservative.

Preferred substitutions at the specified residues are as follows: S32V; L123R; and E240A.

In addition to the mutation(s) noted above, which aim to increase stability and disrupt the polypeptide's ability to bind to fH, a polypeptide can include one or more further mutation(s) e.g. to disrupt the polypeptide's interaction with siderophores. Residues which interact with siderophores can be mutated, using the guidance in references 16 and 35, e.g. by aligning SEQ ID NO: 5 herein with SEQ ID NO: 4 of reference 16 to identify residues which can interact with siderophores e.g. with catecholates, hydroxamates or carboxylates.

Reference 24 reports that certain substitutions in v2 can increase affinity for fH, and so these should usually be avoided e.g. E85 in SEQ ID NO: 5 (residue 157 in ref. 24).

Further residues can also be mutated provided that, compared to the wild-type sequence (e.g. SEQ ID NO: 4), the polypeptide has higher stability, has lower affinity for fH, and when administered to a suitable mammal can elicit an antibody response that is bactericidal against meningococcus.

The polypeptide of the first aspect can comprise SEQ ID NO: 47. In SEQ ID NO: 47, residue 32 is any amino acid, residue 123 is not leucine, and residue 240 is not glutamate. A further option is SEQ ID NO:39, where residue 32 is not serine, residue 123 is not leucine, and residue 240 is not glutamate. In a preferred embodiment of SEQ ID NO: 47, residue 32 is valine, residue 123 is arginine, and residue 240 is alanine (i.e. SEQ ID NO: 50). In another preferred embodiment of SEQ ID NO: 47, residue 32 is serine, residue 123 is arginine, and residue 240 is alanine (i.e. SEQ ID NO: 53).

The polypeptide of the first aspect can comprise SEQ ID NO: 31. In SEQ ID NO: 31, residue 32 is any amino acid, and residue 123 is not leucine. A further option is SEQ ID NO:37, where residue 32 is not serine, and residue 123 is not leucine.In a preferred embodiment of SEQ ID NO: 31, residue 32 is valine, and residue 123 is arginine (i.e. SEQ ID NO: 45). In another preferred embodiment of SEQ ID NO: 31, residue 32 is serine, and residue 123 is arginine (i.e. SEQ ID NO: 54).

The amino acid residues noted for mutation in a v2 sequence are numbered relative to SEQ ID NO: 5 which is from strain 2996. The corresponding amino acid residues in a v2 fHbp from any other strain can be readily identified by sequence alignment e.g. being the amino acid which, when aligned to SEQ ID NO: 5 using a pairwise alignment algorithm (e.g. the Needleman-Wunsch global alignment algorithm, as detailed below), aligns with the amino acid mentioned herein. Often the amino acid will be the same as seen in SEQ ID NO: 5 (e.g. residue 32 will be serine), but the alignment will easily identify if this is not the case.

Mutations Relative to SEQ ID NO: 17

Polypeptides of the second aspect of the invention comprise an amino acid sequence which has at least j % identity to SEQ ID NO: 17, and/or comprise a fragment of SEQ ID NO: 17. In comparison to SEQ ID NO: 17, however, this amino sequence has a modification at least at amino acid residues L126 and E243 (and, optionally, at residue S32). These residues are numbered according to SEQ ID NO: 17; to match the nascent wild-type sequence (SEQ ID NO: 3), the numbering should change +31 (i.e. Ser-32 of SEQ ID NO: 17 is Ser-63 of SEQ ID NO: 3), and to match the mature wild-type sequence (SEQ ID NO: 40) the numbering should change +12.

The two (or three) specified residues can be deleted, but preferably they are substituted by a different amino acid. For example, Leu-126 can be substituted by any of the other 19 naturally-occurring amino acids. When a substitution is made, the replacement amino acid in some embodiments may be a simple amino acid such as glycine or alanine. In other embodiments, the replacement amino acid is a conservative substitution e.g. it is made within the following four groups: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparagine, glutamine, cysteine, serine, threonine, tyrosine. In other embodiments the substitution is non-conservative.

Preferred substitutions at the specified residues are as follows: S32V; L126R; and E243A.

In addition to the mutation(s) noted above, which aim to increase stability and disrupt the polypeptide's ability to bind to fH, a polypeptide can include one or more further mutation(s) e.g. to disrupt the polypeptide's interaction with siderophores. Residues which interact with siderophores can be mutated, using the guidance in references 16 and 35, e.g. by aligning SEQ ID NO: 17 herein with SEQ ID NO: 4 of reference 16 to identify residues which can interact with siderophores e.g. with catecholates, hydroxamates or carboxylates.

Reference 24 reports that certain substitutions in v3 can increase affinity for fH, and so these should usually be avoided e.g. P44 in SEQ ID NO: 17 (residue 106 in ref. 24).

Further residues can also be mutated provided that, compared to the wild-type sequence (e.g. SEQ ID NO: 40), the polypeptide has higher stability, has lower affinity for fH, and when administered to a suitable mammal can elicit an antibody response that is bactericidal against meningococcus.

The polypeptide of the second aspect can comprise SEQ ID NO: 48. In SEQ ID NO: 48, residue 32 is any amino acid, residue 126 is not leucine, and residue 243 is not glutamate. A further option is SEQ ID NO: 57, where residue 32 is not serine, residue 126 is not leucine, and residue 243 is not glutamate. In a preferred embodiment of SEQ ID NO: 48, residue 32 is valine, residue 126 is arginine, and residue 243 is alanine (i.e. SEQ ID NO: 51). In another preferred embodiment of SEQ ID NO: 48, residue 32 is serine, residue 126 is arginine, and residue 243 is alanine (i.e. SEQ ID NO: 55).

The polypeptide of the second aspect can comprise SEQ ID NO: 32. In SEQ ID NO: 32, residue 32 is any amino acid, and residue 126 is not leucine. A further option is SEQ ID NO:38, where residue 32 is not serine, residue 126 is not leucine. In a preferred embodiment of SEQ ID NO: 32, residue 32 is valine, and residue 126 is arginine (i.e. SEQ ID NO: 44). In another preferred embodiment of SEQ ID NO: 32, residue 32 is serine, and residue 126 is arginine (i.e. SEQ ID NO: 56).

The amino acid residues noted for mutation in a v3 sequence are numbered relative to SEQ ID NO: 17 which is from strain M1239. The corresponding amino acid residues in a v3 fHbp from any other strain can be readily identified by sequence alignment e.g. being the amino acid which, when aligned to SEQ ID NO: 17 using a pairwise alignment algorithm (e.g. the Needleman-Wunsch global alignment algorithm, as detailed below), aligns with the amino acid mentioned herein. Often the amino acid will be the same as seen in SEQ ID NO: 17 (e.g. residue 32 will be serine), but the alignment will easily identify if this is not the case.

Mutant Sequences of the Invention

As mentioned above, the polypeptide of the first aspect of the invention can comprise SEQ ID NO: 47 or SEQ ID NO: 37, and the polypeptide of the second aspect can comprise SEQ ID NO: 48 or SEQ ID NO:57.

In a third aspect of the invention, which overlaps with the first aspect, the invention provides a polypeptide comprising an amino acid sequence having at least v % sequence identity to SEQ ID NO: 47, provided that (i) residue 32 is any amino acid, but in some embodiments is not serine (ii) residue 123 is not leucine (iii) residue 240 is not glutamate (iv) compared to the wild-type sequence, e.g.

SEQ ID NO: 4, the polypeptide has higher stability and has lower affinity for fH (v) when administered to a suitable mammal can elicit an antibody response that is bactericidal against a meningococcus which expresses a v2 fHbp. The residue numbering of (i) to (iii) is according to SEQ ID NO: 47.

The value of v may be selected from 80, 85, 86, 87, 88, 89, 90, 91, 92, 93, 94, 95, 96, 97, 98, 99 or more. It is preferably 90 (i.e. the mutant fHbp v2 amino acid sequence has at least 90% identity to SEQ ID NO: 47) and is more preferably 95.

In a fourth aspect of the invention, which overlaps with the second aspect, the invention provides a polypeptide comprising an amino acid sequence having at least w % sequence identity to SEQ ID NO: 48, provided that (i) residue 32 is any amino acid, but in some embodiments is not serine (ii) residue 126 is not leucine (iii) residue 243 is not glutamate (iv) compared to the wild-type sequence, e.g. SEQ ID NO: 40, the polypeptide has higher stability and has lower affinity for fH (v) when administered to a suitable mammal can elicit an antibody response that is bactericidal against a meningococcus which expresses a v3 fHbp. The residue numbering of (i) to (iii) is according to SEQ ID NO: 48.

The value of w may be selected from 80, 85, 86, 87, 88, 89, 90, 91, 92, 93, 94, 95, 96, 97, 98, 99 or more. It is preferably 90 (i.e. the mutant fHbp v3 amino acid sequence has at least 90% identity to SEQ ID NO: 48) and is more preferably 95.

In a fifth aspect, the invention provides a polypeptide comprising amino acid sequence SEQ ID NO: 47, modified by up to 5 single amino acid changes (i.e. 1, 2, 3, 4 or 5 single amino acid substitutions, deletions and/or insertions), provided that (i) residue 32 is any amino acid, but in some embodiments is not serine (ii) residue 123 is not leucine (iii) residue 240 is not glutamate (iv) compared to the wild-type sequence, e.g. SEQ ID NO: 4, the polypeptide has higher stability and has lower affinity for fH (v) when administered to a suitable mammal can elicit an antibody response that is bactericidal against a meningococcus which expresses a v2 fHbp.

In a sixth aspect, the invention provides a polypeptide comprising amino acid sequence SEQ ID NO: 48, modified by up to 5 single amino acid changes (i.e. 1, 2, 3, 4 or 5 single amino acid substitutions, deletions and/or insertions), provided that (i) residue 32 is any amino acid, but in some embodiments is not serine (ii) residue 126 is not leucine (iii) residue 243 is not glutamate (iv) compared to the wild-type sequence, e.g. SEQ ID NO: 40, the polypeptide has higher stability and has lower affinity for fH (v) when administered to a suitable mammal can elicit an antibody response that is bactericidal against a meningococcus which expresses a v3 fHbp. The residue numbering of (i) to (iii) is according to SEQ ID NO: 48.

These various v2 and v3 polypeptides can be combined in fusion polypeptides, thereby providing immune responses against both variants with a single polypeptide. Thus a seventh aspect of the invention provides a polypeptide comprising a fusion of: (i) a polypeptide as defined according to the first, third, or fifth aspects of the invention; and (ii) a polypeptide as defined according to the second, fourth, or sixth aspects of the invention. Advantageously, such fusion polypeptides can, when administered to a suitable mammal, elicit an antibody response that is bactericidal against both a meningococcus which expresses a v2 fHbp and a meningococcus which expresses a v3 fHbp.

Thus, within the seventh aspect, the fusion polypeptide comprises:

(I) a first amino acid sequence selected from:
  a mutant fHbp v2 amino acid sequence, wherein: (a) the amino acid sequence has at least k % sequence identity to SEQ ID NO: 5, and/or comprises a fragment of SEQ ID NO: 5; but
  (b) the amino acid sequence differs from SEQ ID NO: 5 at residues L123 and E240 (and, optionally, also at residue S32);
  an amino acid sequence having at least v % sequence identity to SEQ ID NO: 47, provided that (i) residue 32 is any amino acid, but in some embodiments is not serine (ii) residue 123 is not leucine (iii) residue 240 is not glutamate; or
  the amino acid sequence SEQ ID NO: 47 or SEQ ID NO: 50, optionally modified by up to 5 single amino acid changes (i.e. 1, 2, 3, 4 or 5 single amino acid substitutions, deletions and/or insertions), provided that (i)

residue 32 is any amino acid, but in some embodiments is not serine (ii) residue 123 is not leucine (iii) residue 240 is not glutamate;

and (II) a second amino acid sequence selected from:

a mutant fHbp v3 amino acid sequence, wherein: (a) the amino acid sequence has at least j % sequence identity to SEQ ID NO: 17, and/or comprises a fragment of SEQ ID NO: 17; but (b) the amino acid sequence differs from SEQ ID NO: 17 at residues L126 and E243 (and, in some embodiments, also at residue S32);

an amino acid sequence having at least w % sequence identity to SEQ ID NO: 48, provided that (i) residue 32 is any amino acid, but in some embodiments is not serine (ii) residue 126 is not leucine (iii) residue 243 is not glutamate; or the amino acid sequence SEQ ID NO: 48 or SEQ ID NO: 51, optionally modified by up to 5 single amino acid changes (i.e. 1, 2, 3, 4 or 5 single amino acid substitutions, deletions and/or insertions), provided that (i) residue 32 is any amino acid, but in some embodiments is not serine (ii) residue 126 is not leucine (iii) residue 243 is not glutamate, wherein the fusion polypeptides (a) can, when administered to a suitable mammal, elicit an antibody response that is bactericidal against both a meningococcus which expresses a v2 fHbp and a meningococcus which expresses a v3 fHbp; (b) has higher stability and lower affinity for fH than a wild-type meningococcal fHbp consisting of SEQ ID NO: 4; (c) has higher stability and lower affinity for fH than a wild-type meningococcal fHbp consisting of SEQ ID NO: 40.

The increase in stability is ideally at least 5° C. e.g. at least 10° C., 15° C., 20° C., 25° C., 30° C., 35° C. or more, as discussed above. The lower affinity is preferably at least 10-fold, and ideally at least 100-fold, as discussed above.

In one embodiment of the seventh aspect, the invention provides a polypeptide comprising a first amino acid sequence and a second amino acid sequence, wherein the first amino acid sequence is SEQ ID NO: 47 or SEQ ID NO:39 and the second amino acid sequence is SEQ ID NO: 48 or SEQ ID NO:57.

The first and second amino acid sequences can be in either order from N- to C-terminus, but it is preferred that the first sequence is upstream of the second sequence.

The first and second amino acid sequences can be joined by a linker sequence. Such linker sequence(s) will typically be short (e.g. 20 or fewer amino acids i.e. 19, 18, 17, 16, 15, 14, 13, 12, 11, 10, 9, 8, 7, 6, 5, 4, 3, 2, 1). Examples include short peptide sequences which facilitate cloning, poly-glycine linkers (i.e. $Gly_n$ where n=2, 3, 4, 5, 6, 7, 8, 9, 10 or more (SEQ ID NO: 58)), and histidine tags (i.e. $His_n$ where n=3, 4, 5, 6, 7, 8, 9, 10 or more (SEQ ID NO: 59)). Other suitable linker amino acid sequences will be apparent to those skilled in the art. One useful linker is GSGGGG (SEQ ID NO: 20), with the Gly-Ser dipeptide being formed from a BamHI restriction site, thus aiding cloning and manipulation. Another useful linker is SEQ ID NO: 21, which can optionally be preceded by a Gly-Ser dipeptide (SEQ ID NO: 22, from BamHI) or a Gly-Lys dipeptide (SEQ ID NO: 23, from HindIII).

The fusion polypeptide can also include a v1 fHbp sequence, thereby providing immune responses against all three fHbp variants with a single polypeptide i.e. the polypeptide can, when administered to a suitable mammal, elicit an antibody response that is bactericidal against a meningococcus which expresses a v1 fHbp, a meningococcus which expresses a v2 fHbp, and a meningococcus which expresses a v3 fHbp. Thus a polypeptide of the seventh aspect can also include an amino acid sequence (i) with at least i % sequence identity to SEQ ID NO: 16, and/or (ii) comprising a fragment of SEQ ID NO: 16. The value of i may be selected from 80, 85, 86, 87, 88, 89, 90, 91, 92, 93, 94, 95, 96, 97, 98, 99 or more. It is preferably 90 (i.e. the amino acid sequence has at least 90% identity to SEQ ID NO: 16) and is more preferably 95. The fragment of (ii) will generally be at least 7 amino acids long e.g. 8, 10, 12, 14, 16, 18, 20, 22, 24, 26, 28, 30, 32, 24, 26, 28, 40, 45, 50, 55, 60, 65, 70, 75, 80 or more contiguous amino acids from SEQ ID NO: 16. The fragment will typically include at least one epitope from SEQ ID NO: 16. Sharing at least 30 contiguous amino acids with SEQ ID NO: 16 will be typical, and usually a v1 fHbp amino acid sequence will include several (e.g. 2, 3, 4, 5 or more) fragments from SEQ ID NO: 16. Overall, a v1 fHbp sequence used with the seventh aspect can have at least i % sequence identity to and include several fragments of SEQ ID NO: 16.

Advantageously, the v1 fHbp sequence includes a mutation which gives it a lower affinity (as discussed above) for human fH than the same polypeptide but without the sequence differences of (b), e.g. lower affinity than a wild-type meningococcal polypeptide consisting of SEQ ID NO: 46. For instance, amino acid residue Arg-34 in SEQ ID NO: 16 (residue Arg-60 in SEQ ID NO: 1, and Arg-41 in SEQ ID NO: 46) can be mutated to Ser to disrupt the fHbp/fH interaction [19,21]. Thus a preferred v1 fHbp sequence for use with the invention comprises SEQ ID NO: 49, in which residue 34 is not arginine (e.g. SEQ ID NO: 52, where residue 34 is serine).

Where a polypeptide includes each of a v1, v2 and v3 sequence these can be present in any order from N- to C-terminus i.e. v1-v2-v3, v1-v3-v2, v2-v1-v3, v2-v3-v1, v3-v1-v2, or v3-v2-v1. The most preferred order is v2-v3-v1.

In general a preferred fHbp fusion polypeptide of the invention has an amino acid sequence of formula:

$$NH_2\text{—}A\text{-}[\text{-}X\text{-}L\text{-}]_3\text{-}B\text{—}COOH$$

wherein each X is a different variant fHbp sequence as defined herein, L is an optional linker amino acid sequence, A is an optional N-terminal amino acid sequence, and B is an optional C-terminal amino acid sequence.

The three X moieties are a v1, v2, and v3 sequence as discussed herein, so the polypeptide can, when administered to a suitable mammal, elicit an antibody response that is bactericidal against a meningococcus which expresses a v1 fHbp, a meningococcus which expresses a v2 fHbp, and a meningococcus which expresses a v3 fHbp. As mentioned above, the three variants are preferably in the order from N-terminus to C-terminus v2-v3-v1.

For each instance of [-X-L-], linker amino acid sequence -L- may be present or absent. Suitable linker sequences are discussed above.

-A- is an optional N-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking. If $X_1$ lacks its own N-terminus methionine, -A- may provide such a methionine residue in the translated polypeptide (e.g. -A- is a single Met residue). The Met may be to the N-terminus of a linker sequence such as SEQ ID NO: 21 (i.e. SEQ ID: 24), or at the N-terminus of a short sequence (e.g. SEQ ID NO: 25).

-B- is an optional C-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate cloning or purification (e.g. comprising histidine tags i.e. His$_n$ where n=3, 4, 5, 6, 7, 8, 9, 10 or more (SEQ ID NO: 59)), or sequences which enhance polypeptide stability. Other suitable C-terminal amino acid sequences will be apparent to those skilled in the art. One suitable -B- moiety is SEQ ID NO: 26, in which the Leu-Glu upstream of the histidine tag arises from a XhoI restriction site.

Thus, in one embodiment, the invention provides a polypeptide comprising the amino acid sequence of SEQ ID NO: 28. From N-terminus to C-terminus, this sequence is made up from the following SEQ ID amino acid sequences:

| A | $X_1$ | $L_1$ | $X_2$ | $L_2$ | $X_3$ | $L_3$ | B |
|---|---|---|---|---|---|---|---|
| — | 50 | 20 | 51 | 20 | 52 | — | — |

By including SEQ ID NO: 24 as the N-terminal -A-moiety, the invention also provides a polypeptide comprising the amino acid sequence of SEQ ID NO: 27.

In another embodiment, the invention provides a polypeptide comprising the amino acid sequence of SEQ ID NO: 30. From N-terminus to C-terminus, this sequence is made up from the following SEQ ID amino acid sequences:

| A | $X_1$ | $L_1$ | $X_2$ | $L_2$ | $X_3$ | $L_3$ | B |
|---|---|---|---|---|---|---|---|
| — | 45 | 20 | 44 | 20 | 52 | — | — |

By including SEQ ID NO: 24 as the N-terminal -A-moiety, the invention also provides a polypeptide comprising the amino acid sequence of SEQ ID NO: 29.

Polypeptides

Polypeptides of the invention can be prepared by various means e.g. by chemical synthesis (at least in part), by digesting longer polypeptides using proteases, by translation from RNA, by purification from cell culture (e.g. from recombinant expression or from *N.meningitidis* culture), etc. Heterologous expression in an *E.coli* host is a preferred expression route.

Polypeptides of the invention are ideally at least 100 amino acids long, e.g. 150aa, 175aa, 200aa, 225aa, or longer. They include a mutant fHbp v2 and/or v3 amino acid sequence, and the mutant fHbp v2 or v3 amino acid sequence should similarly be at least 100 amino acids long, e.g. 150aa, 175aa, 200aa, 225aa, or longer.

The fHbp is naturally a lipoprotein in *N.meningitidis*. It has also been found to be lipidated when expressed in *E.coli* with its native leader sequence or with heterologous leader sequences. Polypeptides of the invention may have a N-terminus cysteine residue, which may be lipidated e.g. comprising a palmitoyl group, usually forming tripalmitoyl-S-glyceryl-cysteine. In other embodiments the polypeptides are not lipidated.

Polypeptides are preferably prepared in substantially pure or substantially isolated form (i.e. substantially free from other Neisserial or host cell polypeptides). In general, the polypeptides are provided in a non-naturally occurring environment, e.g. they are separated from their naturally-occurring environment. In certain embodiments, the polypeptide is present in a composition that is enriched for the polypeptide as compared to a starting material. Thus purified polypeptide is provided, whereby purified means that the polypeptide is present in a composition that is substantially free of other expressed polypeptides, whereby substantially free is meant that more than 50% (e.g. ≥75%, ≥80%, ≥90%, ≥95%, or ≥99%) of total polypeptide in the composition is a polypeptide of the invention.

Polypeptides can take various forms (e.g. native, fusions, glycosylated, non-glycosylated, lipidated, disulfide bridges, etc.).

SEQ ID NOs 4, 5, 17 and 40 do not include a N-terminus methionine. If a polypeptide of the invention is produced by translation in a biological host then a start codon is required, which will provide a N-terminus methionine in most hosts. Thus a polypeptide of the invention will, at least at a nascent stage, include a methionine residue upstream of said SEQ ID NO sequence.

Cleavage of nascent sequences means that the mutant fHbp v2 or v3 amino acid sequence might itself provide the polypeptide's N-terminus. In other embodiments, however, a polypeptide of the invention can include a N-terminal sequence upstream of the mutant fHbp v2 or v3 amino acid sequence. In some embodiments the polypeptide has a single methionine at the N-terminus immediately followed by the mutant fHbp v2 or v3 amino acid sequence; in other embodiments a longer upstream sequence may be used. Such an upstream sequence may be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking, or short peptide sequences which facilitate cloning or purification (e.g. a histidine tag i.e. $His_n$ where n=4, 5, 6, 7, 8, 9, 10 or more (SEQ ID NO: 60)). Other suitable N-terminal amino acid sequences will be apparent to those skilled in the art e.g. the native upstream sequences present in SEQ ID NO: 2 or SEQ ID NO: 3.

A polypeptide of the invention may also include amino acids downstream of the final amino acid of the mutant fHbp v2 or v3 amino acid sequence. Such C-terminal extensions may be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate cloning or purification (e.g. comprising a histidine tag i.e. $His_n$ where n=4, 5, 6, 7, 8, 9, 10 or more (SEQ ID NO: 60)), or sequences which enhance polypeptide stability. Other suitable C-terminal amino acid sequences will be apparent to those skilled in the art.

The term "polypeptide" refers to amino acid polymers of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. Polypeptides can occur as single chains or associated chains.

Polypeptides of the invention may be attached or immobilised to a solid support.

Polypeptides of the invention may comprise a detectable label, e.g. a radioactive label, a fluorescent label, or a biotin label. This is particularly useful in immunoassay techniques.

As disclosed in reference 162, fHbp can be split into three domains, referred to as A, B and C. Taking SEQ ID NO: 1, the three domains are (A) 1-119, (B) 120-183 and (C) 184-274:

MNRTAFCCLSLTTALILTACSSGGGGVAADIGAGLADALTAPLDHKDKGL

QSLTLDQSVRKNEKLKLAAQGAEKTYGNGDSLNTGKLKNDKVSRFDFIRQ

IEVDGQLITLESGEFQVYKQSHSALTAFQTEQIQDSEHSGKMVAKRQFRI

GDIAGEHTSFDKLPEGGRATYRGTAFGSDDAGGKLTYTIDFAAKQGNGKI

EHLKSPELNVDLAAADIKPDGKRHAVISGSVLYNQAEKGSYSLGIFGGKA

QEVAGSAEVKTVNGIRHIGLAAKQ

The mature form of domain 'A', from Cys-20 at its N-terminus to Lys-119, is called 'A$_{mature}$'.

Multiple fHbp sequences are known and these can readily be aligned using standard methods. By such alignments the skilled person can identify (a) domains 'A' (and 'A$_{mature}$'), 'B' and 'C' in any given fHbp sequence by comparison to the coordinates in the MC58 sequence, and (b) single residues in multiple fHbp sequences e.g. for identifying substitutions. For ease of reference, however, the domains are defined below:

Domain 'A' in a given fHbp sequence is the fragment of that sequence which, when aligned to SEQ ID NO: 1 using a pairwise alignment algorithm, starts with the amino acid aligned to Met-1of SEQ ID NO: 1 and ends with the amino acid aligned to Lys-119 of SEQ ID NO: 1.

Domain 'A$_{mature}$' in a given fHbp sequence is the fragment of that sequence which, when aligned to SEQ ID NO: 1 using a pairwise alignment algorithm, starts with the amino acid aligned to Cys-20 of SEQ ID NO: 1 and ends with the amino acid aligned to Lys-119 of SEQ ID NO: 1.

Domain 'B' in a given fHbp sequence is the fragment of that sequence which, when aligned to SEQ ID NO: 1 using a pairwise alignment algorithm, starts with the amino acid aligned to Gln-120 of SEQ ID NO: 1 and ends with the amino acid aligned to Gly-183 of SEQ ID NO: 1.

Domain 'C' in a given fHbp sequence is the fragment of that sequence which, when aligned to SEQ ID NO: 1 using a pairwise alignment algorithm, starts with the amino acid aligned to Lys-184 of SEQ ID NO: 1 and ends with the amino acid aligned to Gln-274 of SEQ ID NO: 1.

The preferred pairwise alignment algorithm for defining the domains is the Needleman-Wunsch global alignment algorithm [156], using default parameters (e.g. with Gap opening penalty=10.0, and with Gap extension penalty=0.5, using the EBLOSUM62 scoring matrix). This algorithm is conveniently implemented in the needle tool in the EMBOSS package [157].

In some embodiments, a mutant fHbp v2 or v3 amino acid sequence of the invention is truncated to remove its domain A. In general, however, it is preferred that the mutant fHbp v2 or v3 amino acid sequence should include both a N-terminal β-barrel and a C-terminal β-barrel.

In some embodiments, a polypeptide comprises an amino acid sequence as described above, except that up to 10 amino acids (i.e. 1, 2, 3, 4, 5, 6, 7, 8, 9 or 10) at the N-terminus and/or up to 10 amino acids (i.e. 1, 2, 3, 4, 5, 6, 7, 8, 9 or 10) at the C-terminus are deleted.

Nucleic Acids

The invention provides nucleic acids encoding a polypeptide of the invention as defined above.

Nucleic acids of the invention may be prepared in many ways, e.g. by chemical synthesis (e.g. phosphoramidite synthesis of DNA) in whole or in part, by digesting longer nucleic acids using nucleases (e.g. restriction enzymes), by joining shorter nucleic acids or nucleotides (e.g. using ligases or polymerases), from genomic or cDNA libraries, etc.

Nucleic acids of the invention can take various forms e.g. single-stranded, double-stranded, vectors, primers, probes, labelled, unlabelled, etc.

Nucleic acids of the invention are preferably in isolated or substantially isolated form.

The term "nucleic acid" includes DNA and RNA, and also their analogues, such as those containing modified backbones, and also peptide nucleic acids (PNA), etc.

Nucleic acid according to the invention may be labelled e.g. with a radioactive or fluorescent label.

The invention also provides vectors (such as plasmids) comprising nucleotide sequences of the invention (e.g. cloning or expression vectors, such as those suitable for nucleic acid immunisation) and host cells transformed with such vectors.

Bactericidal Responses

Preferred polypeptides of the invention can elicit antibody responses that are bactericidal against meningococci. Bactericidal antibody responses are conveniently measured in mice and are a standard indicator of vaccine efficacy (e.g. see end-note 14 of ref. 36; also ref. 37). Thus the antibodies will be bactericidal against a test strain in a suitable serum bactericidal assay (SBA).

Polypeptides of the first aspect of the invention can preferably elicit an antibody response, e.g., in a mouse, which is bactericidal against a N.meningitidis strain which expresses a v2 fHbp sequence e.g. one or more of strains 961-5945, 2996, 96217, 312294, 11327, a22, gb013 (=M01-240013), e32, m1090, m4287, 860800, 599, 95N477, 90-18311, c11, m986, m2671, 1000, m1096, m3279, bz232, dk353, m3697, ngh38, and/ or L93/4286. Bactericidal responses can for instance be assessed against var2 strain M2091 (ATCC 13091).

Preferred polypeptides of the first aspect of the invention can elicit antibodies in a mouse which are bactericidal against strain M2091 in a serum bactericidal assay.

Polypeptides of the second aspect of the invention can preferably elicit an antibody response, e.g., in a mouse, which is bactericidal against a N.meningitidis strain which expresses a v3 fHbp sequence e.g. one or more of strains M1239, 16889, gb355 (=M01-240355), m3369, m3813, ngp165. Bactericidal responses can for instance be assessed against var3 strain M01-240355, which is a Neisseria MLST reference strains (id 19265 in ref. 38) which has been fully sequenced (see EMBL ID CP002422 [39])

Preferred polypeptides of the second aspect of the invention can elicit antibodies in a mouse which are bactericidal against strain MO1-240355 in a serum bactericidal assay.

For example, an immunogenic composition comprising these polypeptides can provide a serum bactericidal titer of ≥1:4 using the Goldschneider assay with human complement [40-42], and/or providing a serum bactericidal titer of ≥1:128 using baby rabbit complement.

Immunisation

Polypeptides of the invention may be used as the active ingredient of immunogenic compositions, and so the invention provides an immunogenic composition (e.g. a vaccine) comprising a polypeptide of the invention.

The invention also provides a method for raising an antibody response in a mammal, e.g, a mouse or a human, comprising administering an immunogenic composition of the invention to the mammal. The antibody response is preferably a protective and/or bactericidal antibody response. The invention also provides polypeptides of the invention for use in such methods.

The invention also provides a method for protecting a mammal, e.g., a mouse or a human, against a Neisserial (e.g. meningococcal) infection, comprising administering to the mammal an immunogenic composition of the invention.

The invention provides polypeptides of the invention for use as medicaments (e.g. as immunogenic compositions or as vaccines) or as diagnostic reagents. It also provides the use of nucleic acid or polypeptide of the invention in the manufacture of a medicament for preventing Neisserial (e.g. meningococcal) infection in a mammal, e.g., a mouse or a human.

The mammal is preferably a human. The human may be an adult or, preferably, a child. Where the vaccine is for prophylactic use, the human is preferably a child (e.g. a toddler or infant); where the vaccine is for therapeutic use, the human is preferably an adult. A vaccine intended for children may also be administered to adults e.g. to assess safety, dosage, immunogenicity, etc.

The uses and methods are particularly useful for preventing/treating diseases including, but not limited to, meningitis (particularly bacterial, such as meningococcal, meningitis) and bacteremia. For instance, they are suitable for active immunisation of individuals against invasive meningococcal disease caused by *N.meningitidis* (for example in serogroup B).

Efficacy of therapeutic treatment can be tested by monitoring Neisserial infection after administration of the composition of the invention. Efficacy of prophylactic treatment can be tested by monitoring immune responses against fHbp after administration of the composition. Immunogenicity of compositions of the invention can be determined by administering them to test subjects (e.g. children 12-16 months age, or animal models) and then determining standard parameters including serum bactericidal antibodies (SBA) and ELISA titres (GMT). These immune responses will generally be determined around 4 weeks after administration of the composition, and compared to values determined before administration of the composition. A SBA increase of at least 4-fold or 8-fold is preferred. Where more than one dose of the composition is administered, more than one post-administration determination may be made.

Preferred compositions of the invention can confer an antibody titre in a human patient that is superior to the criterion for seroprotection for each antigenic component for an acceptable percentage of human subjects. Antigens with an associated antibody titre above which a host is considered to be seroconverted against the antigen are well known, and such titres are published by organisations such as WHO. Preferably more than 80% of a statistically significant sample of subjects is seroconverted, more preferably more than 90%, still more preferably more than 93% and most preferably 96-100%.

The invention may be used to elicit systemic and/or mucosal immunity.

Compositions of the invention will generally be administered directly to a human patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration to the thigh or the upper arm is preferred. Injection may be via a needle (e.g. a hypodermic needle), but needle-free injection may alternatively be used. A typical intramuscular dose is about 0.5 ml (e.g. as seen in the BEXSERO™ product).

Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined. For instance, the BEXSERO™ product is administered as two or three doses given note less than 1 month or not less than 2 months apart, depending on the subject (e.g. infants or others).

The immunogenic composition of the invention will generally include a pharmaceutically acceptable carrier, which can be any substance that does not itself induce the production of antibodies harmful to the patient receiving the composition, and which can be administered without undue toxicity. Pharmaceutically acceptable carriers can include liquids such as water, saline, glycerol and ethanol. Auxiliary substances, such as wetting or emulsifying agents, pH buffering substances, and the like, can also be present in such vehicles. A thorough discussion of suitable carriers is available in ref. 43. For example, the BEXSERO™ product includes sodium chloride, histidine, sucrose, aluminium hydroxide, and water for injections.

Neisserial infections affect various areas of the body and so the compositions of the invention may be prepared in various forms. For example, the compositions may be prepared as injectables, either as liquid solutions or suspensions. Solid forms suitable for solution in, or suspension in, liquid vehicles prior to injection can also be prepared. Compositions suitable for parenteral injection (e.g. into muscle) are most preferred. The composition is preferably sterile. It is preferably pyrogen-free. It is preferably buffered e.g. at between pH 6 and pH 8, generally around pH 7. Where a composition comprises an aluminium hydroxide salt, it is preferred to use a histidine buffer [44]. Compositions of the invention may be isotonic with respect to humans.

Immunogenic compositions comprise an immunologically effective amount of immunogen, as well as any other of other specified components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. Dosage treatment may be a single dose schedule or a multiple dose schedule (e.g. including booster doses). The composition may be administered in conjunction with other immunoregulatory agents.

Adjuvants which may be used in compositions of the invention include, but are not limited to insoluble metal salts, oil-in-water emulsions (e.g. MF59 or AS03, both containing squalene), saponins, non-toxic derivatives of LPS (such as monophosphoryl lipid A or 3-O-deacylated MPL), immunostimulatory oligonucleotides, detoxified bacterial ADP-ribosylating toxins, microparticles, liposomes, imidazoquinolones, or mixtures thereof. Other substances that act as immunostimulating agents are disclosed in chapter 7 of ref. 45.

The use of an aluminium hydroxide and/or aluminium phosphate adjuvant is particularly preferred, and polypeptides are generally adsorbed to these salts. These salts include oxyhydroxides and hydroxyphosphates (e.g. see chapters 8 & 9 of ref. 45). The salts can take any suitable form (e.g. gel, crystalline, amorphous, etc.). $Al^{+++}$ should be present at <1 mg/dose.

The most preferred adjuvant is aluminium hydroxide, as used in the BEXSERO™ product. Polypeptides in a composition of the invention can be adsorbed to this adjuvant, as seen in the BEXSERO™ product. It can be included at about 1 mg/ml $Al^{+++}$ (i.e. 0.5mg per 0.5ml dose)

Further Antigenic Components

Compositions of the invention include mutant v2 and/or v3 fHbp sequence. It is useful if the composition should not include complex or undefined mixtures of antigens e.g. it is preferred not to include outer membrane vesicles in the composition. Polypeptides of the invention are preferably expressed recombinantly in a heterologous host and then purified.

As well as including a fHbp polypeptide, a composition of the invention may also include one or more further neisserial immunogen(s), as a vaccine which targets more than one immunogen per bacterium decreases the possibility of selecting escape mutants. Thus a composition can include a second polypeptide that, when administered to a suitable mammal, elicits an antibody response that is bactericidal against meningococcus. The second polypeptide can be a meningococcal fHbp, but will often not be a fHbp e.g. it may be a NHBA sequence, a NadA sequence, etc.

A composition of the invention may include a NHBA antigen. The NHBA antigen was included in the published genome sequence for meningococcal serogroup B strain MC58 [46] as gene NMB2132 (GenBank accession number GI:7227388; SEQ ID NO: 6 herein). The sequences of NHBA antigen from many strains have been published since then. For example, allelic forms of NHBA can be seen in FIGS. 5 and 15 of reference 47, and in example 13 and FIG. 21 of reference 1 (SEQ IDs 3179 to 3184 therein). Various immunogenic fragments of the NHBA antigen have also been reported. Preferred 287 antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 6; and/or (b) comprising a fragment of at least 'n' consecutive amino acids of SEQ ID NO: 6, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 6. The most useful NHBA antigens of the invention can elicit antibodies which, after administration to a subject, can bind to a meningococcal polypeptide consisting of amino acid sequence SEQ ID NO: 6. Advantageous NHBA antigens for use with the invention can elicit bactericidal anti-meningococcal antibodies after administration to a subject.

A composition of the invention may include a NadA antigen. The NadA antigen was included in the published genome sequence for meningococcal serogroup B strain MC58 [46] as gene NMB1994 (GenBank accession number GI:7227256; SEQ ID NO: 7 herein). The sequences of NadA antigen from many strains have been published since then, and the protein's activity as a Neisserial adhesin has been well documented. Various immunogenic fragments of NadA have also been reported. Preferred NadA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 7; and/or (b) comprising a fragment of at least 'n' consecutive amino acids of SEQ ID NO: 7, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 7. The most useful NadA antigens of the invention can elicit antibodies which, after administration to a subject, can bind to a meningococcal polypeptide consisting of amino acid sequence SEQ ID NO: 7. Advantageous NadA antigens for use with the invention can elicit bactericidal anti-meningococcal antibodies after administration to a subject. SEQ ID NO: 15 is one such fragment.

A composition of the invention may include a NspA antigen. The NspA antigen was included in the published genome sequence for meningococcal serogroup B strain MC58 [46] as gene NMB0663 (GenBank accession number GI:7225888; SEQ ID NO: 8 herein). The antigen was previously known from references 48 & 49. The sequences of NspA antigen from many strains have been published since then. Various immunogenic fragments of NspA have also been reported. Preferred NspA antigens for use with the invention comprise n amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 8; and/or (b) comprising a fragment of at least 'n' consecutive amino acids of SEQ ID NO: 8, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 8. The most useful NspA antigens of the invention can elicit antibodies which, after administration to a subject, can bind to a meningococcal polypeptide consisting of amino acid sequence SEQ ID NO: 8. Advantageous NspA antigens for use with the invention can elicit bactericidal anti-meningococcal antibodies after administration to a subject.

Compositions of the invention may include a meningococcal HmbR antigen. The full-length HmbR sequence was included in the published genome sequence for meningococcal serogroup B strain MC58 [46] as gene NMB1668 (SEQ ID NO: 9 herein). The invention can use a polypeptide that comprises a full-length HmbR sequence, but it will often use a polypeptide that comprises a partial HmbR sequence. Thus in some embodiments a HmbR sequence used according to the invention may comprise an amino acid sequence having at least i % sequence identity to SEQ ID NO: 9, where the value of i is 50, 60, 70, 80, 90, 95, 99 or more. In other embodiments a HmbR sequence used according to the invention may comprise a fragment of at least j consecutive amino acids from SEQ ID NO: 9, where the value of j is 7, 8, 10, 12, 14, 16, 18, 20, 25, 30, 35, 40, 50, 60, 70, 80, 90, 100, 150, 200, 250 or more. In other embodiments a HmbR sequence used according to the invention may comprise an amino acid sequence (i) having at least i % sequence identity to SEQ ID NO: 9 and/or (ii) comprising a fragment of at least j consecutive amino acids from SEQ ID NO: 9. Preferred fragments of j amino acids comprise an epitope from SEQ ID NO: 9. Such epitopes will usually comprise amino acids that are located on the surface of HmbR. Useful epitopes include those with amino acids involved in HmbR's binding to haemoglobin, as antibodies that bind to these epitopes can block the ability of a bacterium to bind to host haemoglobin. The topology of HmbR, and its critical functional residues, were investigated in reference 50. The most useful HmbR antigens of the invention can elicit antibodies which, after administration to a subject, can bind to a meningococcal polypeptide consisting of amino acid sequence SEQ ID NO: 9. Advantageous HmbR antigens for use with the invention can elicit bactericidal anti-meningococcal antibodies after administration to a subject.

A composition of the invention may include a NhhA antigen. The NhhA antigen was included in the published genome sequence for meningococcal serogroup B strain MC58 [46] as gene NMB0992 (GenBank accession number GI:7226232; SEQ ID NO: 10 herein). The sequences of NhhA antigen from many strains have been published since e.g. refs 47 & 51, and various immunogenic fragments of NhhA have been reported. It is also known as Hsf. Preferred NhhA antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 10; and/or (b) comprising a fragment of at least 'n' consecutive amino acids of SEQ ID NO: 10, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 10. The most useful NhhA antigens of the invention can elicit antibodies which, after administration to a subject, can bind to a meningococcal polypeptide consisting of amino acid sequence SEQ ID NO: 10. Advantageous NhhA antigens for use with the invention can elicit bactericidal anti-meningococcal antibodies after administration to a subject.

A composition of the invention may include an App antigen. The App antigen was included in the published genome sequence for meningococcal serogroup B strain MC58 [46] as gene NMB1985 (GenBank accession number GI:7227246; SEQ ID NO: 11 herein). The sequences of App antigen from many strains have been published since then. Various immunogenic fragments of App have also been reported. Preferred App antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 11; and/or (b) comprising a fragment of at least 'n' consecutive amino acids of SEQ ID NO: 11, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 11. The most useful App antigens of the invention can elicit antibodies which, after administration to a subject, can bind to a meningococcal polypeptide consisting of amino acid sequence SEQ ID NO: 11. Advantageous App antigens for use with the invention can elicit bactericidal anti-meningococcal antibodies after administration to a subject.

A composition of the invention may include an Omp85 antigen. The Omp85 antigen was included in the published genome sequence for meningococcal serogroup B strain MC58 [46] as gene NMB0182 (GenBank accession number GI:7225401; SEQ ID NO: 12 herein). The sequences of Omp85 antigen from many strains have been published since then. Further information on Omp85 can be found in references 52 and 53. Various immunogenic fragments of Omp85 have also been reported. Preferred Omp85 antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 12; and/or (b) comprising a fragment of at least 'n' consecutive amino acids of SEQ ID NO: 12, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 12. The most useful Omp85 antigens of the invention can elicit antibodies which, after administration to a subject, can bind to a meningococcal polypeptide consisting of amino acid sequence SEQ ID NO: 12. Advantageous Omp85 antigens for use with the invention can elicit bactericidal anti-meningococcal antibodies after administration to a subject.

A composition of the invention may include a 936 antigen. The 936 antigen was included in the published genome sequence for meningococcal serogroup B strain MC58 [46] as gene NMB2091 (SEQ ID NO: 13 herein). Preferred 936 antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 13; and/or (b) comprising a fragment of at least 'n' consecutive amino acids of SEQ ID NO: 13, wherein 'n' is 7 or more (e.g. 8, 10, 12, 14, 16, 18, 20, 25, 30, 35, 40, 50, 60, 70, 80, 90, 100, 150, 200, 250 or more). Preferred fragments of (b) comprise an epitope from SEQ ID NO: 13. The most useful 936 antigens of the invention can elicit antibodies which, after administration to a subject, can bind to a meningococcal polypeptide consisting of amino acid sequence SEQ ID NO: 13. The 936 antigen is a good fusion partner for fHbp (e.g. see references 54 & 55).

A composition may comprise: a polypeptide comprising SEQ ID NO: 14; a polypeptide comprising SEQ ID NO: 15; and a polypeptide of the invention comprising a mutant fHbp v2 amino acid sequence and SEQ ID NO: 13 (cf. refs. 54 & 55).

A composition may comprise: a polypeptide comprising SEQ ID NO: 14; a polypeptide comprising SEQ ID NO: 15; and a polypeptide of the invention comprising a mutant fHbp v3 amino acid sequence and SEQ ID NO: 13 (cf. refs. 54 & 55).

In some embodiments, a polypeptide of the invention is combined with a further meningococcal fHbp sequence. In particular, a v2 polypeptide can be combined with a v1 and/or a v3 polypeptide to increase the spectrum of strain coverage [160]. Thus a composition can comprise: (i) a polypeptide of the invention comprising a mutant fHbp v2 amino acid sequence; and (ii) a v1 fHbp polypeptide and/or a v3 fHbp polypeptide. In other embodiments, a polypeptide of the invention can comprise (i) a mutant fHbp v2 amino acid sequence and (ii) a v1 fHbp amino acid sequence and/or a v3 fHbp amino acid sequence. Thus the v1 and/or v3 sequences can be combined with the mutant v2 sequence as separate entities in a composition (or within a fusion polypeptide, as discussed above).

Similarly, a v3 polypeptide can be combined with a v1 and/or a v2 polypeptide to increase the spectrum of strain coverage [160]. Thus a composition can comprise: (i) a polypeptide of the invention comprising a mutant fHbp v3 amino acid sequence; and (ii) a v1 fHbp polypeptide and/or a v2 fHbp polypeptide. In other embodiments, a polypeptide of the invention can comprise (i) a mutant fHbp v3 amino acid sequence and (ii) a v1 fHbp amino acid sequence and/or a v2 fHbp amino acid sequence. Thus the v1 and/or v2 sequences can be combined with the mutant v3 sequence as separate entities in a composition (or within a fusion polypeptide, as discussed above).

Moreover, mutant v2 and v3 polypeptides can be combined with each other to increase strain coverage. Thus a composition can comprise: (i) a polypeptide of the invention comprising a mutant fHbp v2 amino acid sequence; (ii) a polypeptide of the invention comprising a mutant fHbp v3 amino acid sequence; and (iii) a fHbp v1 polypeptide. In other embodiments, a polypeptide of the invention can comprise (i) a mutant fHbp v2 amino acid sequence (ii) a mutant v3 fHbp amino acid sequence and (iii) a fHbp v1 amino acid sequence. Thus the mutant v2 and v3 sequences can be combined with a v1 sequence as separate entities in a composition (or within a fusion polypeptide, as discussed above). The v1 sequence can be a wild-type sequence or a mutant sequence.

A v1 fHbp can comprise (a) an amino acid sequence which has at least k % identity to SEQ ID NO: 16, and/or (b) a fragment of SEQ ID NO: 16. Information about 'k' and fragments are given above. The fragment will typically include at least one epitope from SEQ ID NO: 16, and the v1 fHbp polypeptide will include at least one epitope which is not present in the v2 or v3 amino acid sequence of the invention, such that antibodies elicited by the v1 fHbp can recognise v1 strains. Ideally, the v1 fHbp can elicit antibodies which are bactericidal against v1 strains e.g. against strain MC58 (available from the ATCC as 'BAA-335'). The v1 fHbp can include an amino acid mutation which disrupts its ability to bind to fH.

A v2 fHbp can comprise (a) an amino acid sequence which has at least k % identity to SEQ ID NO: 5, and/or (b) a fragment of SEQ ID NO: 5. Information about 'k' and fragments are given above. The fragment will typically include at least one epitope from SEQ ID NO: 5, and the v2 fHbp polypeptide will include at least one epitope which is not present in the v3 amino acid sequence of the invention, such that antibodies elicited by the v2 fHbp can recognise v2 strains. Ideally, the v2 fHbp can elicit antibodies which are bactericidal against v2 strains e.g. against strain M2091 (ATCC 13091). The v2 fHbp can be a polypeptide of the first aspect of the invention.

A v3 fHbp can comprise (a) an amino acid sequence which has at least k % identity to SEQ ID NO: 17, and/or (b) a fragment of SEQ ID NO: 17. Information about 'k' and fragments are given above. The fragment will typically include at least one epitope from SEQ ID NO: 17, and the v3 fHbp polypeptide will include at least one epitope which is not present in the v2 amino acid sequence of the invention, such that antibodies elicited by the v3 fHbp can recognise v3 strains. Ideally, the v3 fHbp can elicit antibodies which are bactericidal against v3 strains e.g. against strain M01-240355.

The v3 fHbp can be a polypeptide of the second aspect of the invention.

In addition to Neisserial polypeptide antigens, the composition may include antigens for immunising against other diseases or infections. For example, the composition may include one or more of the following further antigens:

a saccharide antigen from *N.meningitidis* serogroup A, C, W135 and/or Y, such as the saccharide disclosed in ref. 56 from serogroup C (see also ref. 57) or in ref. 58.

a saccharide antigen from *Streptococcus pneumoniae* [e.g. 59, 60, 61].

an antigen from hepatitis A virus, such as inactivated virus [e.g. 62, 63].

an antigen from hepatitis B virus, such as the surface and/or core antigens [e.g. 63, 64].

a diphtheria antigen, such as a diphtheria toxoid [e.g. chapter 3 of ref. 65] e.g. the $CRM_{197}$ mutant [e.g. 66].

a tetanus antigen, such as a tetanus toxoid (e.g. chapter 4 of ref. 65).

an antigen from *Bordetella pertussis*, such as pertussis holotoxin (PT) and filamentous haemagglutinin (FHA) from *B.pertussis*, optionally also in combination with pertactin and/or agglutinogens 2 and 3 (e.g. refs. 67 & 68).

a saccharide antigen from *Haemophilus influenzae* B [e.g. 57].

polio antigen(s) [e.g. 69, 70] such as IPV.

measles, mumps and/or rubella antigens (e.g. chapters 9, 10 & 11 of ref. 65).

influenza antigen(s) (e.g. chapter 19 of ref. 65), such as the haemagglutinin and/or neuraminidase surface proteins.

an antigen from *Moraxella catarrhalis* [e.g. 71].

an protein antigen from *Streptococcus agalactiae* (group B streptococcus) [e.g. 72, 73].

a saccharide antigen from *Streptococcus agalactiae* (group B streptococcus).

an antigen from *Streptococcus pyogenes* (group A streptococcus) [e.g. 73, 74, 75].

an antigen from *Staphylococcus aureus* [e.g. 76].

The composition may comprise one or more of these further antigens.

Toxic protein antigens may be detoxified where necessary (e.g. detoxification of pertussis toxin by chemical and/or genetic means [68]).

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens. DTP combinations are thus preferred.

Saccharide antigens are preferably in the form of conjugates. Carrier proteins for the conjugates are discussed in more detail below.

Antigens in the composition will typically be present at a concentration of at least 1 µg/ml each. In general, the concentration of any given antigen will be sufficient to elicit an immune response against that antigen.

Immunogenic compositions of the invention may be used therapeutically (i.e. to treat an existing infection) or prophylactically (i.e. to prevent future infection).

As an alternative to using proteins antigens in the immunogenic compositions of the invention, nucleic acid (which could be RNA, such as a self-replicating RNA, or DNA, such as a plasmid) encoding the antigen may be used.

In some embodiments a composition of the invention comprises in addition to the fHbp sequence, conjugated capsular saccharide antigens from 1, 2, 3 or 4 of meningococcus serogroups A, C, W135 and Y. In other embodiments a composition of the invention comprises in addition to the fHbp sequence, at least one conjugated pneumococcal capsular saccharide antigen.

Meningococcus Serogroups Y, W135, C and A

Current serogroup C vaccines (MENJUGATE™ [56,77], MENINGITEC™ and NEISVAC-C™) include conjugated saccharides. Menjugate™ and Meningitec™ have oligosaccharide antigens conjugated to a $CRM_{197}$ carrier, whereas NEISVAC-C™ uses the complete polysaccharide (de-O-acetylated) conjugated to a tetanus toxoid carrier. The MENACTRA™ vaccine contains conjugated capsular saccharide antigens from each of serogroups Y, W135, C and A.

Compositions of the present invention may include capsular saccharide antigens from one or more of meningococcus serogroups Y, W135, C and A, wherein the antigens are conjugated to carrier protein(s) and/or are oligosaccharides. For example, the composition may include a capsular saccharide antigen from: serogroup C; serogroups A and C; serogroups A, C and W135; serogroups A, C and Y; serogroups C, W135 and Y; or from all four of serogroups A, C, W135 and Y.

A typical quantity of each meningococcal saccharide antigen per dose is between 1 μg and 20 μg e.g. about 1 μg, about 2.5 μg, about 4 μg, about 5 μg, or about 10 μg (expressed as saccharide).

Where a mixture comprises capsular saccharides from both serogroups A and C, the ratio (w/w) of MenA saccharide:MenC saccharide may be greater than 1 (e.g. 2:1, 3:1, 4:1, 5:1, 10:1 or higher). Where a mixture comprises capsular saccharides from serogroup Y and one or both of serogroups C and W135, the ratio (w/w) of MenY saccharide:MenW135 saccharide may be greater than 1 (e.g. 2:1, 3:1, 4:1, 5:1, 10:1 or higher) and/or that the ratio (w/w) of MenY saccharide:MenC saccharide may be less than 1 (e.g. 1:2, 1:3, 1:4, 1:5, or lower). Preferred ratios (w/w) for saccharides from serogroups A:C:W135:Y are: 1:1:1:1; 1:1:1:2; 2:1:1:1; 4:2:1:1; 8:4:2:1; 4:2:1:2; 8:4:1:2; 4:2:2:1; 2:2:1:1; 4:4:2:1; 2:2:1:2; 4:4:1:2; and 2:2:2:1. Preferred ratios (w/w) for saccharides from serogroups C:W135:Y are: 1:1:1; 1:1:2; 1:1:1; 2:1:1; 4:2:1; 2:1:2; 4:1:2; 2:2:1; and 2:1:1. Using a substantially equal mass of each saccharide is preferred.

Capsular saccharides may be used in the form of oligosaccharides. These are conveniently formed by fragmentation of purified capsular polysaccharide (e.g. by hydrolysis), which will usually be followed by purification of the fragments of the desired size.

Fragmentation of polysaccharides is preferably performed to give a final average degree of polymerisation (DP) in the oligosaccharide of less than 30 (e.g. between 10 and 20, preferably around 10 for serogroup A; between 15 and 25 for serogroups W135 and Y, preferably around 15-20; between 12 and 22 for serogroup C; etc.). DP can conveniently be measured by ion exchange chromatography or by colorimetric assays [78].

If hydrolysis is performed, the hydrolysate will generally be sized in order to remove short-length oligosaccharides [57]. This can be achieved in various ways, such as ultrafiltration followed by ion-exchange chromatography. Oligosaccharides with a degree of polymerisation of less than or equal to about 6 are preferably removed for serogroup A, and those less than around 4 are preferably removed for serogroups W135 and Y.

Preferred MenC saccharide antigens are disclosed in reference 77, as used in MENJUGATE™.

The saccharide antigen may be chemically modified. This is particularly useful for reducing hydrolysis for serogroup A [79]. De-O-acetylation of meningococcal saccharides can be performed. For oligosaccharides, modification may take place before or after depolymerisation.

Where a composition of the invention includes a MenA saccharide antigen, the antigen is preferably a modified saccharide in which one or more of the hydroxyl groups on the native saccharide has/have been replaced by a blocking group [79]. This modification improves resistance to hydrolysis.

Covalent Conjugation

Capsular saccharides in compositions of the invention will usually be conjugated to carrier protein(s). In general, conjugation enhances the immunogenicity of saccharides as it converts them from T-independent antigens to T-dependent antigens, thus allowing priming for immunological memory. Conjugation is particularly useful for paediatric vaccines and is a well known technique.

Typical carrier proteins are bacterial toxins, such as diphtheria or tetanus toxins, or toxoids or mutants thereof. The $CRM_{197}$ diphtheria toxin mutant [80] is useful, and is the carrier in the PREVNAR™ product. Other suitable carrier proteins include the *N.meningitidis* outer membrane protein complex [81], synthetic peptides [82,83], heat shock proteins [84,85], pertussis proteins [86,87], cytokines [88], lymphokines [88], hormones [88], growth factors [88], artificial proteins comprising multiple human $CD4^+$ T cell epitopes from various pathogen-derived antigens [89] such as N19 [90], protein D from *H.influenzae* [91-93], pneumolysin [94] or its non-toxic derivatives [95], pneumococcal surface protein PspA [96], iron-uptake proteins [97], toxin A or B from *C.difficile* [98], recombinant *P.aeruginosa* exoprotein A (rEPA) [99], etc.

Any suitable conjugation reaction can be used, with any suitable linker where necessary.

The saccharide will typically be activated or functionalised prior to conjugation. Activation may involve, for example, cyanylating reagents such as CDAP (e.g. 1-cyano-4-dimethylamino pyridinium tetrafluoroborate [100,101, etc.]). Other suitable techniques use carbodiimides, hydrazides, active esters, norborane, p-nitrobenzoic acid, N-hydroxysuccinimide, S-NHS, EDC, TSTU, etc.

Linkages via a linker group may be made using any known procedure, for example, the procedures described in references 102 and 103. One type of linkage involves reductive amination of the polysaccharide, coupling the resulting amino group with one end of an adipic acid linker group, and then coupling a protein to the other end of the adipic acid linker group [104,105]. Other linkers include B-propionamido [106], nitrophenyl-ethylamine [107], haloacylhalides [108], glycosidic linkages [109], 6-aminocaproic acid [110], ADH [111], $C_4$ to $C_{12}$ moieties [112] etc. As an alternative to using a linker, direct linkage can be used. Direct linkages to the protein may comprise oxidation of the polysaccharide followed by reductive amination with the protein, as described in, for example, references 113 and 114.

A process involving the introduction of amino groups into the saccharide (e.g. by replacing terminal =O groups with —$NH_2$) followed by derivatisation with an adipic diester (e.g. adipic acid N-hydroxysuccinimido diester) and reaction with carrier protein is preferred. Another preferred reaction uses CDAP activation with a protein D carrier e.g. for MenA or MenC.

Outer Membrane Vesicles (OMVs)

It is preferred that compositions of the invention should not include complex or undefined mixtures of antigens, which are typical characteristics of OMVs. However, the invention can be used in conjunction with OMVs, as fHbp has been found to enhance their efficacy [4], whether by simple mixing or by over-expressing the polypeptides of the invention in the strains used for OMV preparation.

This approach may be used in general to improve preparations of *N.meningitidis* serogroup B microvesicles [115], 'native OMVs' [116], blebs or outer membrane vesicles (e.g. refs. 117 to 123, etc.).

Typical outer membrane vesicles are prepared artificially from bacteria, and may be prepared using detergent treatment (e.g. with deoxycholate), or by non-detergent means (e.g. see reference 127). Techniques for forming OMVs include treating bacteria with a bile acid salt detergent (e.g. salts of lithocholic acid, chenodeoxycholic acid, ursodeoxycholic acid, deoxycholic acid, cholic acid, ursocholic acid, etc., with sodium deoxycholate [124 & 125] being preferred for treating *Neisseria*) at a pH sufficiently high not to precipitate the detergent [126]. Other techniques may be performed substantially in the absence of detergent [127, 128] using techniques such as sonication, homogenisation, microfluidisation, cavitation, osmotic shock, grinding, French press, blending, etc. Methods using no or low detergent can retain useful antigens such as NspA and fHbp [127]. Thus OMVs used with the invention may be prepared using an OMV extraction buffer having about 0.5% deoxycholate or lower e.g. about 0.2%, about 0.1%, <0.05% or even zero.

The vesicles known as MVs (membrane vesicles) and NOMVs (native outer membrane vesicles) are naturally-occurring membrane vesicles that form spontaneously during bacterial growth and are released into culture medium. MVs can be obtained by culturing *Neisseria* in broth culture medium, separating whole cells from the smaller MVs in the broth culture medium (e.g. by filtration or by low-speed centrifugation to pellet only the cells and not the smaller vesicles), and then collecting the MVs from the cell-depleted medium (e.g. by filtration, by differential precipitation or aggregation of MVs, by high-speed centrifugation to pellet the MVs). Strains for use in production of MVs can generally be selected on the basis of the amount of MVs produced in culture e.g. refs. 135 & 136 describe *Neisseria* with high MV production.

Vesicles may be prepared from bacteria which have been genetically manipulated [129-132] e.g. to increase immunogenicity (e.g. hyper-express immunogens), to reduce toxicity, to inhibit capsular polysaccharide synthesis, to down-regulate PorA expression, etc. They may be prepared from hyperblebbing strains [133-136]. Vesicles from bacteria with different class I outer membrane protein subtypes may be used e.g. six different subtypes [137,138] using two different genetically-engineered vesicle populations each displaying three subtypes, or nine different subtypes using three different genetically-engineered vesicle populations each displaying three subtypes, etc. Useful subtypes include: P1.7,16; P1.5-1,2-2; P1.19,15-1; P1.5-2,10; P1.12-1,13; P1.7-2,4; P1.22,14; P1.7-1,1; P1.18-1,3,6. In general, however, it is preferred for the present invention to prepare OMVs from a wild-type meningococcus strain.

Vesicles for use with the invention can thus be prepared from any wild-type meningococcal strain. The vesicles will usually be from a serogroup B strain, but it is possible to prepare them from serogroups other than B (e.g. reference discloses 126a process for serogroup A), such as A, C, W135 or Y. The strain may be of any serotype (e.g. 1, 2a, 2b, 4, 14, 15, 16, etc.), any serosubtype (e.g. P1.4), and any immunotype (e.g. L1; L2; L3; L3,7; L3,7,9; L10; etc.). The meningococci may be from any suitable lineage, including hyperinvasive and hypervirulent lineages e.g. any of the following seven hypervirulent lineages: subgroup I; subgroup III; subgroup IV-1; ET-5 complex; ET-37 complex; A4 cluster; lineage 3. Most preferably, OMVs are prepared from the strain NZ98/254, or another strain with the P1.4 PorA serosubtype. The invention advantageously uses the same OMVs which are used in the BEXSERO™ and MENZB™ products, prepared from the strain NZ98/254.

Vesicles will generally include meningococcal lipooligosaccharides (LOS, also known as LPS, lipopolysaccharide), but the pyrogenic effect of LOS in OMVs is much lower than seen with the same amount of purified LOS, and adsorption of OMVs to aluminium hydroxide further reduces pyrogenicity. LOS levels are expressed in International Units (IU) of endotoxin and can be tested by the LAL assay (limulus amebocyte lysate). Preferably, LOS is present at less than 2000 IU per µg of OMV protein.

When LOS is present in a vesicle it is possible to treat the vesicle so as to link its LOS and protein components ("intra-bleb" conjugation [139]).

A useful process for OMV purification is described in reference 140 and involves ultrafiltration on crude OMVs, rather than instead of high speed centrifugation. The process may involve a step of ultracentrifugation after the ultrafiltration takes place. The process may involve a step of ultracentrifugation after the ultrafiltration takes place. OMVs can also be purified using the two stage size filtration process described in ref. 152.

OMVs can usefully be suspended in a sucrose solution after they have been prepared.

Host Cells

The invention provides a bacterium which expresses a polypeptide of the invention. The bacterium may be a meningococcus or an *E.coli*. The bacterium may constitutively express the polypeptide, but in some embodiments expression may be under the control of an inducible promoter. The bacterium may hyper-express the polypeptide (cf. ref.141). Expression of the polypeptide is ideally not phase variable.

The invention also provides outer membrane vesicles prepared from a bacterium of the invention (particularly from a meningococcus). It also provides a process for producing vesicles from a bacterium of the invention. Vesicles prepared from these strains preferably include the polypeptide of the invention, which should be in an immunoaccessible form in the vesicles i.e. an antibody which can bind to purified polypeptide of the invention should also be able to bind to the polypeptide which is present in the vesicles.

Bacteria of the invention may, in addition to encoding a polypeptide of the invention, have one or more further modifications. For instance, they may have a modified fur gene [142]. Expression of nspA expression may be up-regulated with concomitant porA and cps knockout. Further knockout mutants of *N.meningitidis* for OMV production are disclosed e.g. in reference 139. Reference 143 discloses the construction of vesicles from strains modified to express six different PorA subtypes. Mutant *Neisseria* with low endotoxin levels, achieved by knockout of enzymes involved in LPS biosynthesis, may also be used [144,145]. Mutant *Neisseria* engineered to reduce or switch off expression of at least one gene involved in rendering toxic the lipid A portion of LPS, in particular of lpx/1 gene, can be used with the invention [146]. Similarly, mutant *Neisseria* engineered to reduce or switch off expression of at least one gene involved in the capsular polysaccharide synthesis or export, in particular of synX and/or ctrA genes can be used with the invention. These or others mutants can all be used with the invention.

In some embodiments a strain may have been down-regulated for PorA expression e.g. in which the amount of PorA has been reduced by at least 20% (e.g. ≥30%, ≥40%, ≥50%, ≥60%, ≥70%, ≥80%, ≥90%, ≥95%, etc.), or even knocked out, relative to wild-type levels (e.g. relative to strain H44/76).

In some embodiments a strain may hyper-express (relative to the corresponding wild-type strain) certain proteins. For instance, strains may hyper-express NspA, protein 287 [117], fHbp [141] (including fHbp of the invention), TbpA and/or TbpB [147], Cu,Zn-superoxide dismutase, HmbR, etc.

A gene encoding a polypeptide of the invention may be integrated into the bacterial chromosome or may be present in episomal form e.g. within a plasmid.

Advantageously for vesicle production, a meningococcus may be genetically engineered to ensure that expression of the polypeptide is not subject to phase variation. Methods for reducing or eliminating phase variability of gene expression in meningococcus are disclosed in reference 148.

For example, a gene may be placed under the control of a constitutive or inducible promoter, or by removing or replacing the DNA motif which is responsible for its phase variability.

In some embodiments a strain may include one or more of the knockout and/or hyper-expression mutations disclosed in references 122, 129, 133, and 139. For instance, following the guidance and nomenclature in these four documents, useful genes for down-regulation and/or knockout include: (a) Cps, CtrA, CtrB, CtrC, CtrD, FrpB, GalE, HtrB/MsbB, LbpA, LbpB, LpxK, Opa, Opc, PilC, PorB, SiaA, SiaB, SiaC, SiaD, TbpA, and/or TbpB; (b) CtrA, CtrB, CtrC, CtrD, FrpB, GalE, HtrB/MsbB, LbpA, LbpB, LpxK, Opa, Opc, PhoP, PilC, PmrE, PmrF, SiaA, SiaB, SiaC, SiaD, TbpA, and/or TbpB; (c) ExbB, ExbD, rmpM, CtrA, CtrB, CtrD, GalE, LbpA, LpbB, Opa, Opc, PilC, PorB, SiaA, SiaB, SiaC, SiaD, TbpA, and/or TbpB; or (d) CtrA, CtrB, CtrD, FrpB, OpA, OpC, PilC, PorB, SiaD, SynA, SynB, SynX and/or SynC.

Where a mutant strain is used, in some embodiments it may have one or more, or all, of the following characteristics: (i) down-regulated or knocked-out LgtB and/or GalE to truncate the meningococcal LOS; (ii) up-regulated TbpA; (iii) up-regulated NhhA; (iv) up-regulated Omp85; (v) up-regulated LbpA; (vi) up-regulated NspA; (vii) knocked-out PorA; (viii) down-regulated or knocked-out FrpB; (ix) down-regulated or knocked-out Opa; (x) down-regulated or knocked-out Opc; (xii) deleted cps gene complex. A truncated LOS can be one that does not include a sialyl-lacto-N-neotetraose epitope e.g. it might be a galactose-deficient LOS. The LOS may have no a chain.

Depending on the meningococcal strain used for preparing the vesicles, they may or may not include the strain's native fHbp antigen [149].

In one preferred embodiment, a meningococcus does not express a functional MltA protein. As discussed in refs. 150 & 151, knockout of MltA (the membrane-bound lytic transglycosylase, also known as GNA33) in meningococcus provides bacteria which spontaneously release large amounts of membrane vesicles into culture medium, from which they can be readily purified. For instance, the vesicles can be purified using the two stage size filtration process of ref. 152, comprising: (i) a first filtration step in which vesicles are separated from the bacteria based on their different sizes, with the vesicles passing into the filtrate; and (ii) a second filtration step in which the vesicles are retained in the retentate. The MltA mutation (down-regulation or knockout) has been used in 'GMMA' vaccines [153], and can conveniently be combined with further down regulation or knockout of in particular of at least one gene involved in rendering toxic the lipid A portion of LPS, particularly of lpxl1 and/or of at least one gene involved in the capsular polysaccharide synthesis or export, particularly of synX and/or ctrA genes.

A preferred meningococcal strain for a 'GMMA' (Generalized Module for Membrane Antigens) vaccine using this approach expresses a mutant v2 fHbp of the first, third or fifth aspect and/or a mutant v3 fHbp of the second, fourth or sixth aspect of the invention, and expression can be driven by strong promoters. Vesicles released by this strain include the mutant v2 and/or v3 fHbp proteins in immunogenic form, and administration of the vesicles can provide bactericidal antibody response as discussed in reference 153. The strain can also express a v1 fHbp, or a v1 fHbp can instead be provided as a separate recombinant protein in soluble form (and the v1 fHbp can be a wild-type or a mutant sequence e.g. mutated to disrupt its ability to bind to fH, as discussed above). The invention provides such strains, and also provides the vesicles which these strains release e.g. as purified from culture media after growth of the strains. A preferred v2 mutant for expression in these strains has a mutation at L123 and E240 (and optionally S32) as discussed herein, and a preferred v3 mutant for expression in these strains has a mutation at L126 and E243 (and optionally S32) as discussed herein. Thus vesicles prepared from meningococci expressing these v2 and v3 mutant fHbp sequences are particularly preferred immunogens for use in vaccines of the invention. A useful wild-type v2 sequence for mutagenesis in this way comprises SEQ ID NO: 35 or SEQ ID NO: 33 (comprising AG form SEQ ID NO: 34), and a useful wild-type v3 sequence for mutagenesis in this way comprises SEQ ID NO: 36.

Useful promoters for use in such strains include those disclosed in references 154 and 155. For instance, the promoter can be: (a) the promoters from a porin genes, preferably porA or porB, particularly from *N.meningitidis*; or (b) a rRNA gene promoter (such as a 16S rRNA gene), particularly from *N.meningitidis*. Where a meningococcal porin promoter is used, it is preferably from porA, and even more particularly a −10 region from a meningococcal porA gene promoter, and/or a −35 region from a meningococcal porA gene promoter (preferably wherein the -10 region and the −35 region are separated by an intervening sequence of 12-20 nucleotides, and wherein the intervening sequence either contains no poly-G sequence or includes a poly-G sequence having no more than eight consecutive G nucleotides). Where a rRNA gene promoter is used, it can comprise more particularly (i) a −10 region from a meningococcal rRNA gene promoter and/or (ii) a −35 region from a meningococcal rRNA gene promoter. It is also possible to use a hybrid of (a) and (b), for instance to have a −10 region from a porA promoter and a −35 region from a rRNA promoter (which can be a consensus −35 region). A useful promoter can thus be a promoter which includes either (i) a −10 region from a (particularly meningococcal) rRNA gene and a −35 region from a (particularly meningococcal) porA gene, or (ii) a −10 region from a (particularly meningococcal) porA gene and a −35 region from a (particularly meningococcal) rRNA gene.

General

The term "comprising" encompasses "including" as well as "consisting" e.g. a composition "comprising" X may consist exclusively of X or may include something additional e.g. X+Y. References to "comprising" (or "comprises", etc.) may optionally be replaced by references to "consisting of" (or "consists of", etc.).

The term "about" in relation to a numerical value x is optional and means, for example, x±10%.

The word "substantially" does not exclude "completely" e.g. a composition which is "substantially free" from Y may be completely free from Y. Where necessary, the word "substantially" may be omitted from the definition of the invention.

"Sequence identity" is preferably determined by the Needleman-Wunsch global alignment algorithm [156], using default parameters (e.g. with Gap opening penalty=10.0, and with Gap extension penalty=0.5, using the EBLOSUM62 scoring matrix). This algorithm is conveniently implemented in the needle tool in the EMBOSS package [157]. Where the application refers to sequence identity to a particular SEQ ID, the identity should be calculated over the entire length of that SEQ ID.

After serogroup, meningococcal classification includes serotype, serosubtype and then immunotype, and the standard nomenclature lists serogroup, serotype, serosubtype, and immunotype, each separated by a colon e.g. B:4:P1.15:L3,7,9. Within serogroup B, some lineages cause disease often (hyperinvasive), some lineages cause more severe forms of disease than others (hypervirulent), and others rarely cause disease at all. Seven hypervirulent lineages are recognised, namely subgroups I, III and IV-1, ET-5 complex, ET-37 complex, A4 cluster and lineage 3. These have been defined by multilocus enzyme electrophoresis (MLEE), but multilocus sequence typing (MLST) has also been used to classify meningococci. The four main hypervirulent clusters are ST32, ST44, ST8 and ST11 complexes.

In general, the invention does not encompass the various fHbp sequences specifically disclosed in references 2, 3, 5, 6, 7, 158, 159, 160, 161, 162, 163, 164, and 165.

EXAMPLES

Example 1

Mutagenesis for fH Binding

Wild-type v2 protein (SEQ ID NO:2) shows strong binding to fH when assessed by surface plasmon resonance (SPR) using immobilised human fH (FIG. 1, top line). To disrupt fHbp's ability to bind to fH, Glu-266 in v2 (E240 in SEQ ID NO: 5; corresponds to E248 in references 19 & 25) and Glu-274 in v3 (E243 in SEQ ID NO: 17) were mutated to Ala. The E266A mutation in v2 strongly reduced fH binding (FIG. 1, bottom line).

Similarly, the known 'R41S' mutation of v1 fHbp was introduced (SEQ ID NO: 52).

Example 2

Mutagenesis for Stability Increase

Figure 2:
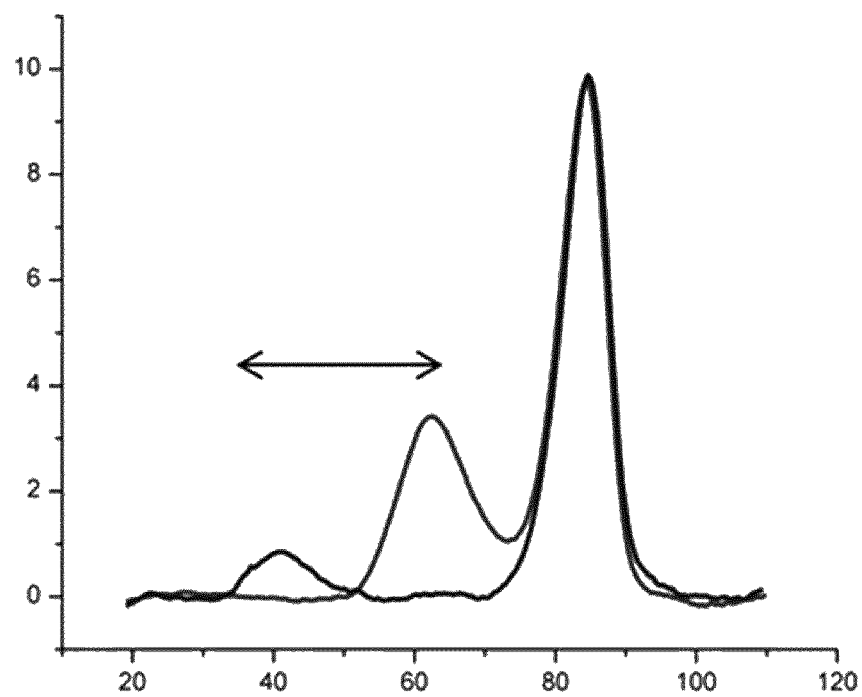
FIG. 2 shows DSC results for wild-type and S58V/L149R mutant v2 fHbp. The C-terminal domain was unaffected by the mutation, but the Tm of the N-terminal domain was increased by >20° C. (marked with the arrow). The y-axis shows Cp (kcal/mol/° C.), and the x-axis shows temperature (° C.).

Both v2 and v3 fHbp are significantly less stable than v1, particularly in their N-terminal domains, and v2 is the least stable of the three variants. To improve stability in v2, two residues were mutated: Ser-58 of SEQ ID NO:2 (S32 in SEQ ID NO: 5) and Leu-149 of SEQ ID NO:2 (L123 in SEQ ID NO: 5) were mutated to Val and Arg, respectively. The mutant v2 protein (SEQ ID NO: 19) was analysed by DSC and, compared to the wild-type sequence SEQ ID NO:2, the $T_m$ of the C-terminal domain was not affected by the mutation. The $T_m$ of the N-terminus domain is >20° C. higher (FIG. 2, increase marked with arrow).The equivalent mutations have also been introduced into v3 (SEQ ID NO: 44).

Surprisingly, although the S58V and L149R mutations had been introduced to improve stability, and did indeed achieve this goal, FIG. 1 (middle line) shows that the mutant polypeptide (SEQ ID NO:19) (even without the E266A mutation) also showed much reduced binding to fH. Furthermore, in a serum bactericidal assay this v2 mutant could compete for binding to human antibodies which had been raised against SEQ ID NO: 18:

| rSBA | Strain: Var 2.19 | Strain: Var 2.16 |
| --- | --- | --- |
| Competitor | Rabbit 20-1 741(2-3-1) | Rabbit 20-1 741(2-3-1) |
| None | 2048 | 4096 |
| 741 V2 S58/L149R | <16 | <16 |

Figure 3:
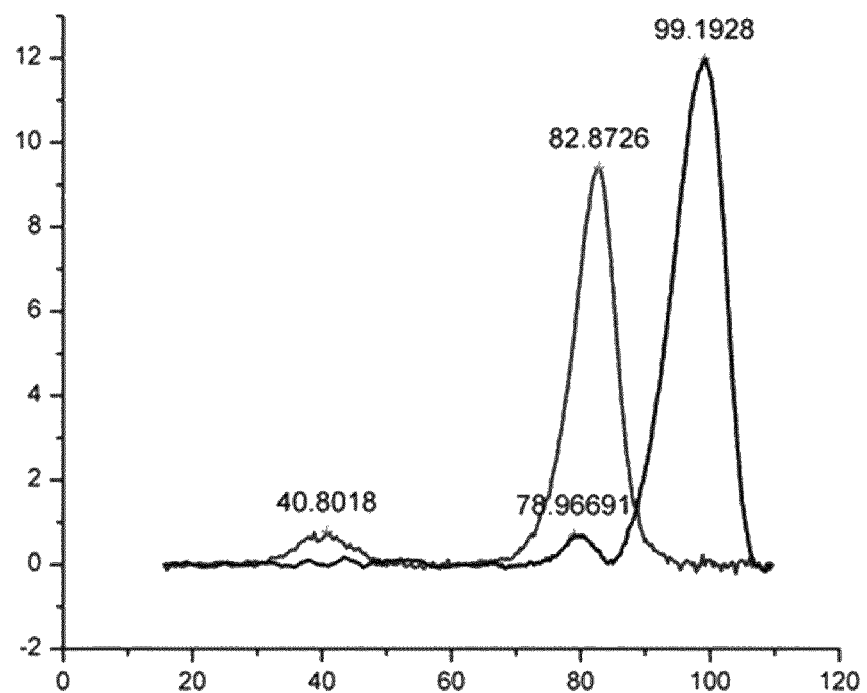
FIG. 3 shows DSC results for wild-type and E266A mutant v2 fHbp. The N-terminal transition vanishes in the mutant, but the Tm of the C-terminal domain was increased by >16° C.

The S58V/L149R stabilising mutation in v2 had a surprising impact on fH binding, so the effect of E266A on stability was also investigated. Unexpectedly, this mutation decreased the stability of the N-terminus domain, but increased stability of the C-terminus domain by >15° C. (from 83° C. up to 99° C., as shown in FIG. 3, compared to wild-type, thus suggesting a potential stabilisation of the beta barrel.

The effects of the individual S58V and L149R mutations on fH binding were studied in v3. Thus, numbered according to SEQ ID NO: 17, mutation S32V or L126R was introduced into the v3 sequence. These two mutants were compared to two different wild-type v3 sequences, and also to the 'E313A' mutant which is known to disrupt fH binding in v3 [23].

Figure 6:
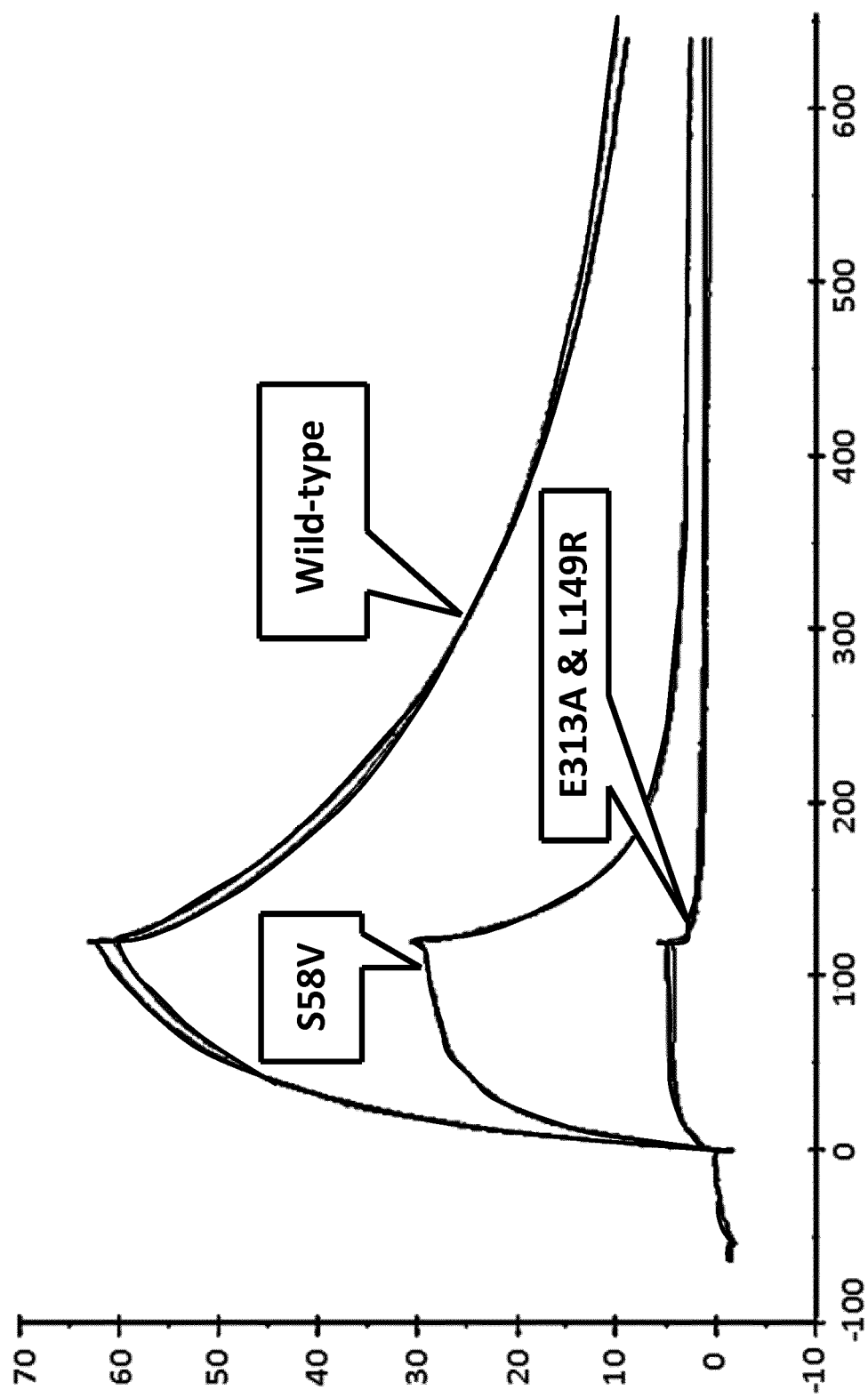
FIG. 6 shows the SPR response of v3 fHbp, either as wild-type (top) or with various mutations.

As shown in FIG. 6, both wild-type v3 bind fH (top two lines). The S58V mutation, which was designed to improve stability, reduced the SPR peak by about 2-fold. Most surprisingly, the L149R mutation (again, designed to improve stability) reduced fH affinity to a similar level to the known E313A mutant (bottom two lines). The S58V and L149R mutations in v3 were also studied by DSC, and were found to increase the N-terminal $T_m$ by 5.5° C. (S58V) or by 6.7° C. (L149R). The $T_m$ of each mutant was higher than seen in the v2 S58V/L149R double mutant. The L149R v3 mutant also showed a higher $T_m$ value for its C-terminal domain, whereas there was almost no shift for the S58V v3 mutant.

Example 3

Fusion Polypeptides

Figure 8A:
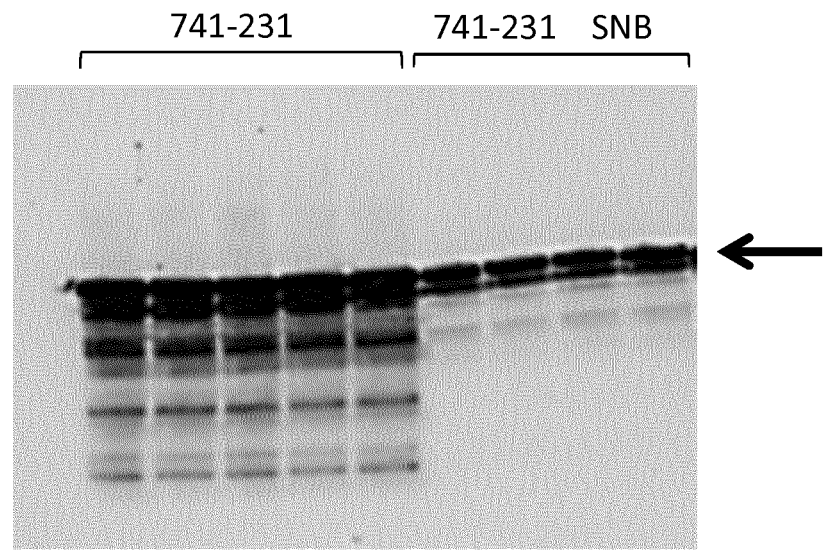
FIG. 8a shows that truncated forms of the stabilised non-binding fusion are less prevalent.
Figure 8B:
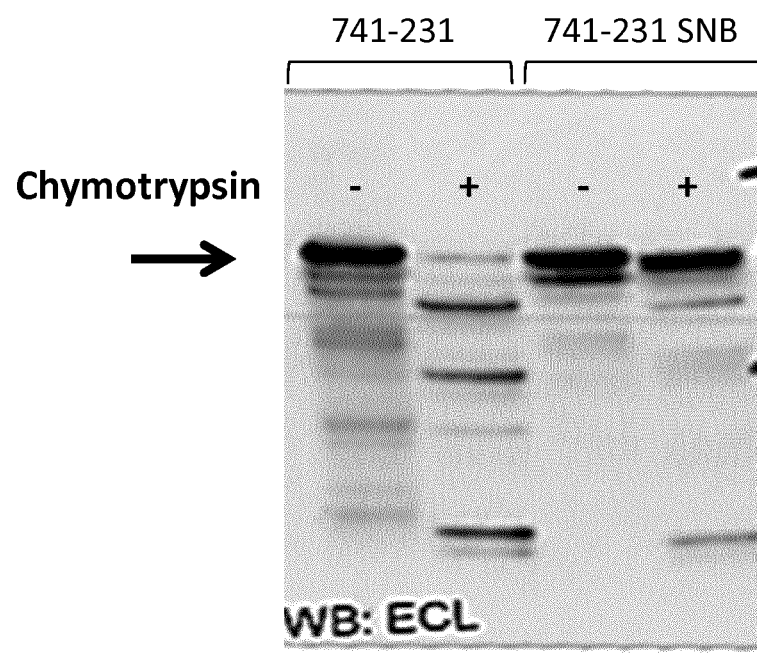
FIG. 8b demonstrates that the stabilised non-binding fusion is less prone to cleavage by chymotrypsin than the 'wild-type' fusion.
Figure 9:
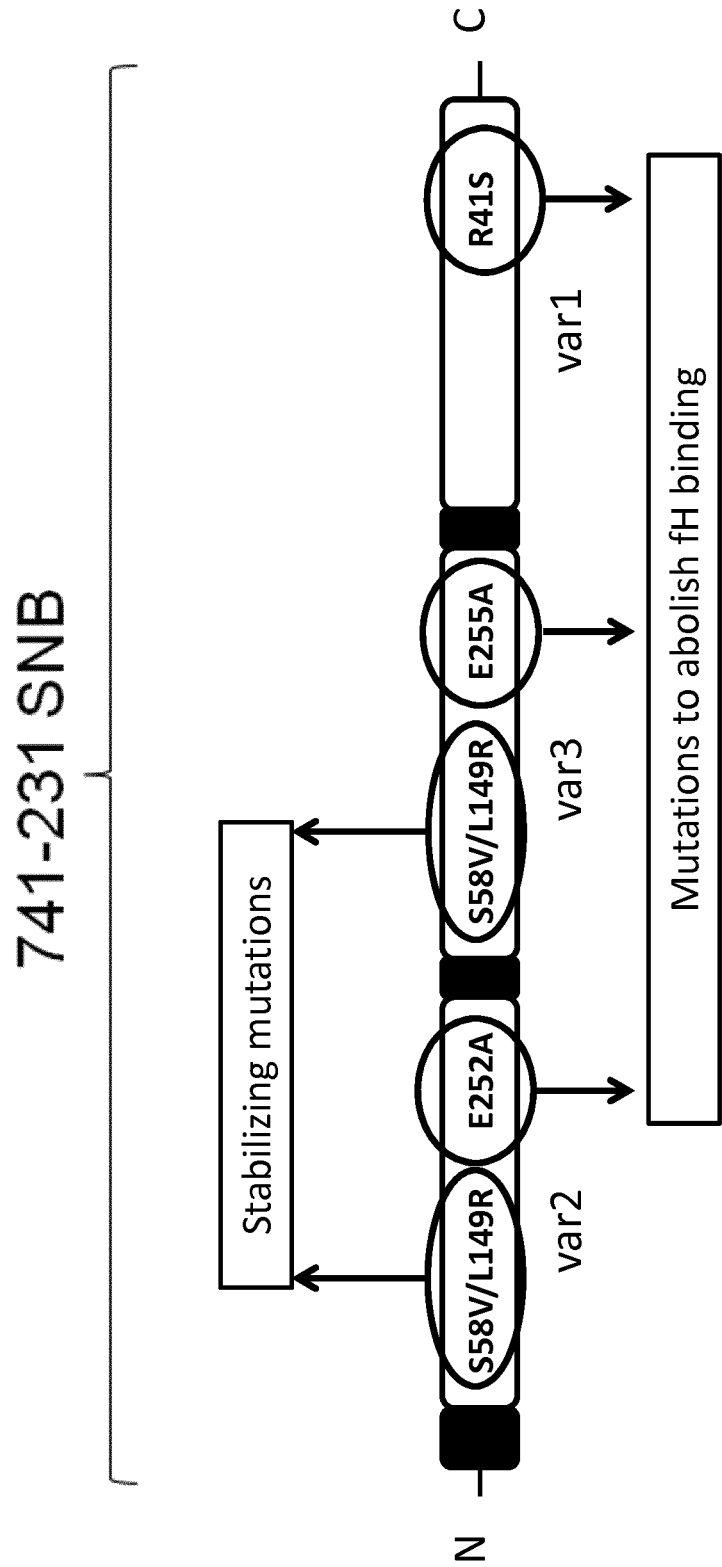
FIG. 9 provides a schematic of the 231 SNB fusion.

The mutations for stability and fHbp binding were combined into mutant forms of v2 (SEQ ID NO: 50) and v3 (SEQ ID NO: 51). These were fused with the mutant v1 sequence (SEQ ID NO:52) in the order v2-v3-v1 and were joined using linkers, to give SEQ ID NO: 27 ('SNB'). Thus, compared to the three wild-type sequences, this fusion polypeptide includes a total of 7 point mutations (FIG. 9). The SNB fusion was compared to a 'wild-type' fusion polypeptide without these point mutations (SEQ ID NO: 18; SEQ ID NO: 36 from reference 163). *E.coli* extracts expressing both forms of the protein were probed by western blot, and degradation forms of the protein were much less visible using the stabilised non-binding forms of the fusion (SEQ ID NO: 27) (FIG. 8).

Figure 4:
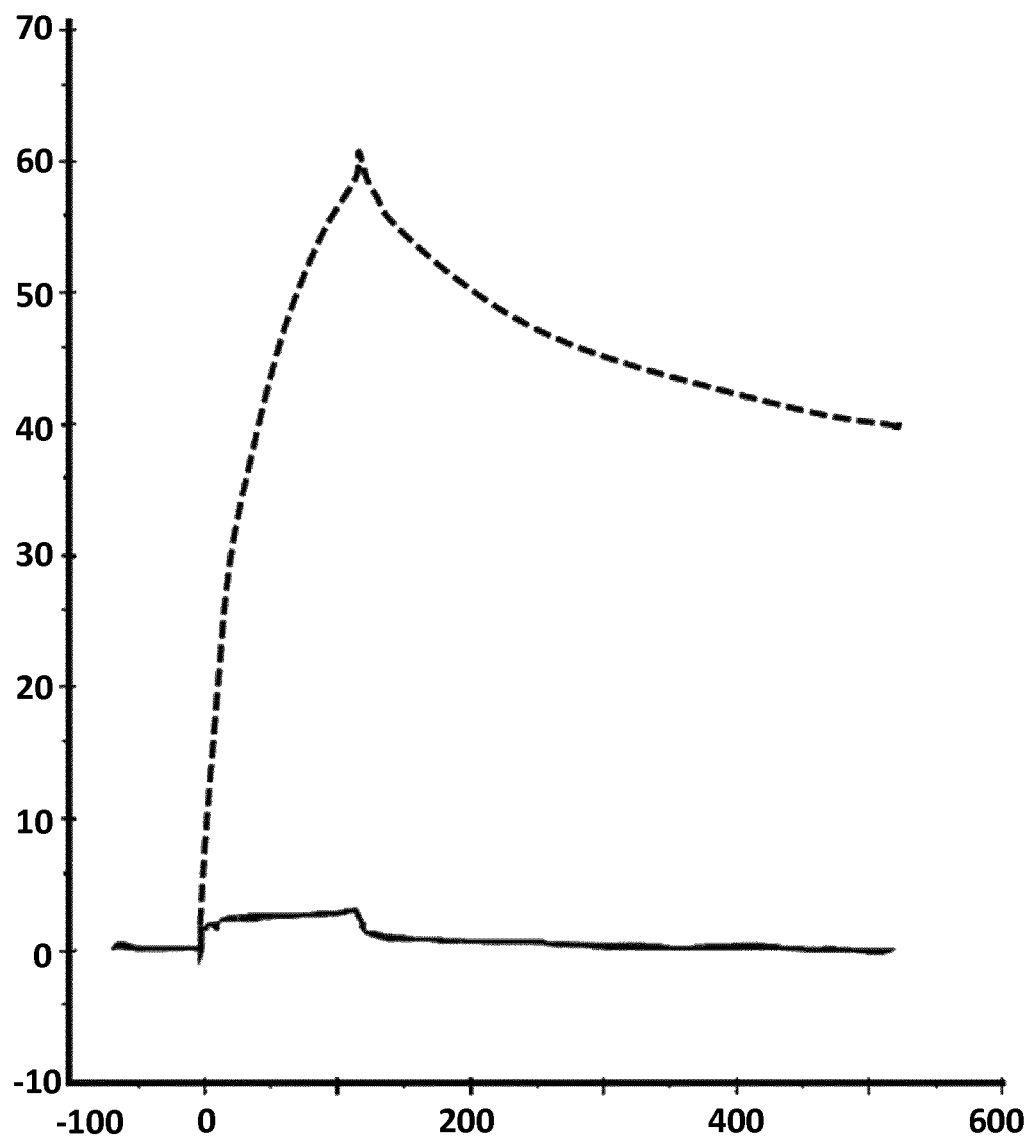
FIG. 4 shows the SPR response of the 'wild-type' (upper line, dashed) and 'SNB mutant' (lower line, solid) v2-v3-v1 fHbp fusion polypeptides.

Binding of the SNB fusion to fH was investigated by SPR, and compared to the 'wild-type' fusion. FIG. 4 shows that the 'wild-type' fusion shows strong binding to fH (top line), whereas the SNB mutant does not interact significantly with fH (bottom line).

Figure 5A:
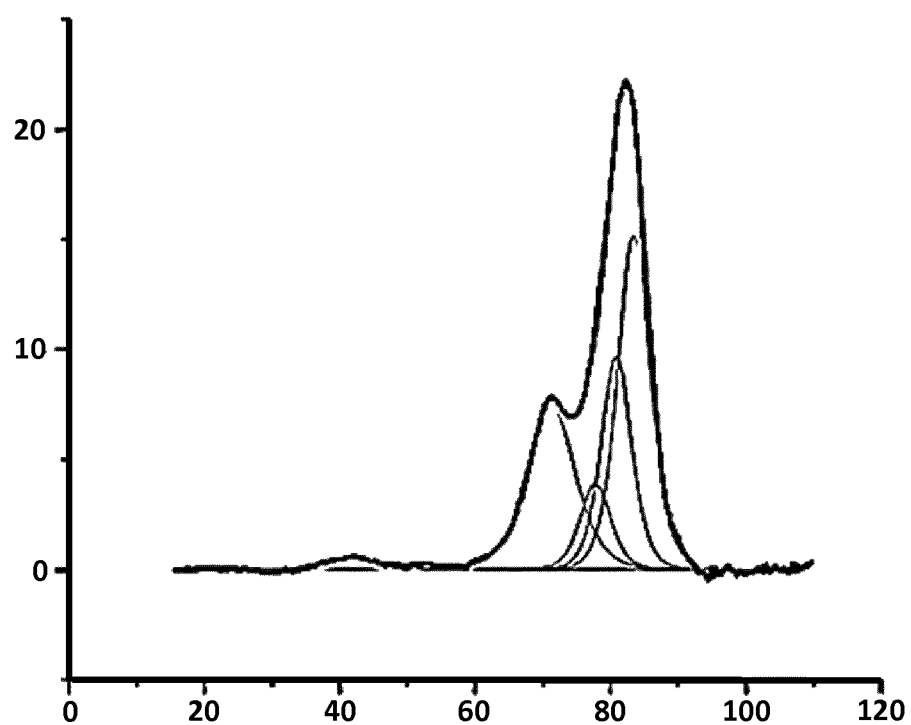
FIG. 5 shows DSC results for the (A) 'wild-type' and (B) 'SNB mutant' v2-v3-v1 fHbp fusion polypeptides.
Figure 5B:
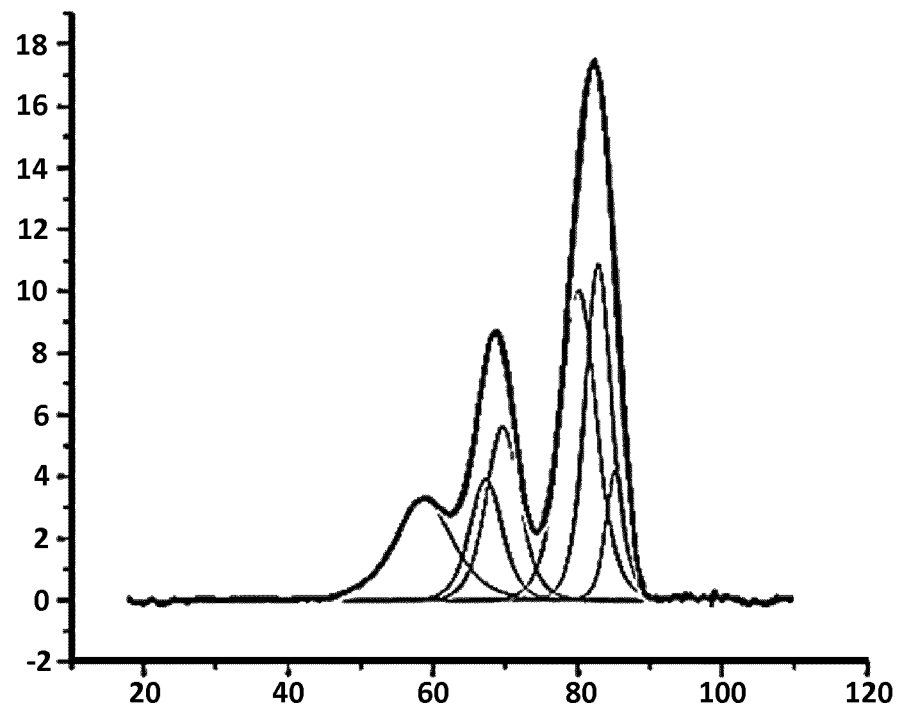

Stability of the two fusion polypeptides was investigated using DSC (FIG. 5). The thermogram for the 'wild-type' fusion (FIG. 5A) did not include any N-terminal transition attributable to v3, suggesting that this domain was not correctly folded. In contrast, with the 'SNB' mutant the thermogram showed transitions for all 6 domains (3 each for N- and C-termini), indicating that they are all correctly folded (FIG. 5B).

Separately, the mutations for stability in v2 (SEQ ID NO: 45) and v3 (SEQ ID NO: 44) were fused with the 'R41S' mutant v1 sequence (SEQ ID NO:52) in the order v2-v3-v1 and were joined using linkers, to give SEQ ID NO: 29. Thus, compared to the three wild-type sequences, this fusion polypeptide includes a total of 5 point mutations.

The ability of non-fH binding forms of fHbp to elicits SBA titers was tested in transgenic (Tg) mice:

|  | rSBA titers obtained against prototypic strains | | |
|---|---|---|---|
| Antigen | Var 1.1 | Var 2.16 | Var 3.42 |
| fHbp fusion SEQ ID NO: 18 | 1024* | 4096 | 8192 |
| fHbp fusion SEQ ID NO: 27 | 16384 | 32768 | >32768 |

These data indicate that non-binding forms of fHbp may be more immunogenic.

Example 4

3D Structures

Previously, the fHbp var.3 structure has been resolved only in complex with fH. For the v2 fHbp-fH complex, only the C-terminal domain of fHbp was detectable in previous studies.

Crystals of the V2 and V3 fHbp mutants were prepared as followed: Crystallization experiments were performed using a Gryphon crystallization robot (Art Robbins Instruments). X-ray diffraction data were collected at the Swiss Light Source (Paul Scherrer Institute, Villigen, Switzerland) beamline X06DA on a Pilatus 2M detector or collected on beamline BM30A of European Synchrotron Radiation Facility (ESRF), Grenoble, France. All diffraction data were processed with iMosflm, scaled with Aimless and crystallographic manipulations were carried out with the CCP4 package.

| fHbp Construct | Crystals | Structure (Å) |
|---|---|---|
| fHbp v2.1 S58V/L149R | YES | YES (1.7) |
| fHbp v3.1 S58V/L149R | YES | YES (3.3) |

Figure 7A:
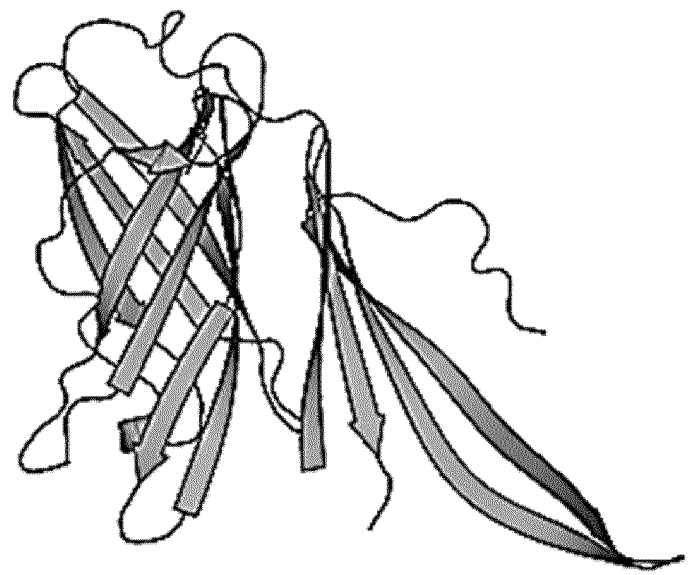
FIG. 7 shows the structures of v2 (FIG. 7a) and v3 (FIG. 7b) fHbp determined by X-ray crystallography in the absence of factor H following stabilisation of fHbp using the S58 and L149 mutations.
Figure 7B:

Stabilizing mutations potentiate structure determination of var.2 Nterminus and the X-ray structure of fHbp var.3 S58V has been solved in the absence of fH. fHbp var.2 and var.3 are characterized by a less stable folding in comparison with var.1. In line with this observation, the full length structure of fHbp var2 and var3 has been difficult to determine. Stabilization of protein translates into preservation of both structure and functionality, coupled to the establishment of a better thermodynamic equilibrium with the (micro)environment. As a result, protein stabilization often results in the obtainment of crystals suitable for structure determination. The S58V and L149R stabilized substitutions enabled determination of the entire fHbp var.3 crystal structure and the resolution of the segment 81-254 of fhbp var.2. By introducing stabilising mutations the almost complete structure of the N-terminal has been obtained in the absence of fH (FIG. 7).

Example 5

Surface Plasmon Resonance (SPR) Analysis

SPR was used to analyze the binding of 231 chimeric proteins to fH proteins. All SPR experiments were performed using a Biacore T200 instrument at 25° C. (GE Healthcare). In brief a carboxymethylated dextran sensor chip (CM-5; GE Healthcare) was prepared where similar densities (~400-500 response units (RUs)) of 231 proteins were immobilized by amine coupling. The proteins immobilized were:

231 wt (SEQ ID NO: 18) purification MenB 547 (0.26 mg/ml) immobilized on Flow cell 2

231 S, comprising R41S, S58V and L149 for both v2 and v3, (SEQ ID NO: 29) purification MenB 532 (0.68 mg/ml) immobilized on Flow cell 3

231 SNB, comprising R41S, S58V and L149 for both v2 and v3, E252A and E255A (SEQ ID NO: 27) purification MenB 512 (0.78 mg/ml) immobilized on Flow cell 4

These proteins were diluted to 5 ug/ml in Acetate pH 5.5 and a standard amine coupling protocol was followed to reach target density. Flow cell 1 was prepared as the other Fcs but no protein was used. Flow cell 1 was then used as reference cell and resulting signal was subtracted from the signal resulting from other flow cells. Running buffer contained 10 mM Hepes, 150 mM NaCl, 0.05% (vol/vol) P20 surfactant, pH 7.4 (HBS-P- GE-Healthcare). Then fH proteins were injected as a range of five injections of increasing analyte concentration with a 2 fold dilution (62.5 nM to 1M) for binding experiments. The following fH constructs were tested: factor H full length (Calbiochem) and factor H comprising only domains 6-7 (Schneider et al., Nature 458, 890-893) provided by C. Tang.

After each injection surfaces were then regenerated with an injection of 20 seconds of 10 mM glycine pH 1.7. A blank injection of buffer only was subtracted from each curve, and reference sensorgrams were subtracted from experimental sensorgrams to yield curves representing specific binding. The data shown are representative of two independent experiments. SPR data were analyzed using the Biacore T200 Evaluation software (GE Healthcare). Resulting sensorgrams were fitted with the 1:1 Langmuir binding model, including a term to account for potential mass transfer, to obtain the individual kon and koff kinetic constants; the individual values were then combined to derive the single averaged KD values (KD=koff/kon) reported. Steady-state analysis was also used to obtain thermodynamic dissociation constants (KD) at pH 7.4. Results of Titration with injections of fH domains 6-7are shown below:

| Fusion | fH prot. | $K_{on}$ (1/Ms) | $K_{off}$ (1/s) | $K_D$ from 1:1 fitting (M) | $K_D$ from steady state analysis (M) | Ration $K_D$ wt/x (residual binding) |
|---|---|---|---|---|---|---|
| 231 WT | fH 67 | 6.4 E+5 | 0.008 | 1.24 E−8 | 2.1 E−8 | 1 (wt/wt) |
| 231 S | fH 67 | 7.1 E+5 | 0.11 | 1.58 E−7 | 2.8 E−7 | 0.076 (wt/S) |
| 231 SNB | fH 67 | 2.8 E+5 | 0.29 | 1.05 E−6 | 2.0 E−6 | 0.011 (wt/SNB) |

From binding tests a strong reduction of at least 90% of the binding to fH was observed for the 231 S protein compared to 231 wt and of at least 98% for the 231 SNB protein compared to 231 wt.

Results of the titration with fH full length are provided below:

| Fusion | fH prot. | $K_{on}$ (1/Ms) | $K_{off}$ (1/s) | $K_D$ from 1:1 fitting (M) | Ration $K_D$ wt/x (residual binding) |
|---|---|---|---|---|---|
| 231 WT | fH f.1. | 1.1E+4 | 0.003 | 3.1E−7 | 1 (wt/wt) |
| 231 S | fH f.1. | 2.1E+4 | 0.064 | 3.1E−6 | 0.1 (wt/S) |
| 231 SNB | fH f.1. | 2.7E+3 | 0.06 | 2.1E−5 | 0.015 (wt/SNB) |

From both binding tests we observe a strong reduction of at least 90% of the binding to fH for the 231 S protein compared to 231 wt and of 98% for the 231 SNB protein compared to 231 wt.

It will be understood that the invention is described above by way of example only and modifications may be made whilst remaining within the scope and spirit of the invention.

REFERENCES

[1] WO99/57280.
[2] Masignani et al. (2003) *J Exp Med* 197:789-799.
[3] Welsch et al. (2004) *J Immunol* 172:5605-15.
[4] Hou et al. (2005) *J Infect Dis* 192(4):580-90.
[5] WO03/063766.
[6] Fletcher et al. (2004) *Infect Immun* 72:2088-2100.
[7] Zhu et al. (2005) *Infect Immun* 73(10):6838-45.
[8] Cendron et al. (2011) *Acta Crystallogr Sect F Struct Biol Cryst Commun.* 67:531-5.
[9] Mascioni et al. (2009) *J Biol Chem* 284:8738-46.
[10] Pizza et al. (2008) *Vaccine* 26 Suppl 8:I46-8.
[11] Malito et al. (2013) *PNAS USA* 110:3304-9.
[12] Marshall et al. (2012) *Pediatr Infect Dis J* 31:1061-8.
[13] McNeil et al. (2013) *Microbiol Mol Biol Rev* 77:234-52.
[14] Serruto et al. (2012) *Vaccine* 30 Suppl 2: B87-97.
[15] Scarselli et al. (2011) *Sci Transl Med* 3:91ra62.
[16] WO2011/051893.
[17] WO2010/046715.
[18] Schneider et al. (2009) *Nature* 458:890-5.
[19] WO2011/126863.
[20] Beernink et al. (2010) *Clin Vaccine Immunol* 17:1074-8.
[21] Beernink et al. (2011) *J Immunol* 186:3606-14.
[22] Rossi et al. (2013) *Vaccine* 31:5451-7.
[23] van der Veen et al. (2014) *Infect Immun PMID* 24379280.
[24] Johnson et al. (2012) *PLoS Pathogen* 8:e1002981.
[25] Pajon et al. (2012) *Infect Immun* 80:2667-77.
[26] Granoff et al. (2013) *Clin Vaccine Immunol* 20:1099-107.
[27] WO2014/030003.
[28] Beernink et al. (2008) *Infect Immun* 76:4232-40.
[29] Scarselli et al. (2009) *J Mol Biol* 386:97-108.
[30] Giuntini et al. (2012) *PLoS One* 7:e34272.
[31] Vu et al. (2012) *Sci Rep* 2:341.
[32] Faleri et al. (2013) *FASEB J* fj.13-239012.
[33] Johnson (2013) *Arch Biochem Biophys* 531:100-9.
[34] Bruylants et al. (2005) *Current Medicinal Chemistry* 12:2011-20.
[35] Veggi et al. (2012) *Biochemistry* 51:9384-93.
[36] Pizza et al. (2000) *Science* 287:1816-1820.
[37] WO2007/028408.
[38] http://pubmist.org/neisseria/
[39] Budroni et al. (2011) *PNAS USA* 108:4494-99.
[40] Goldschneider et al. (1969) *J. Exp. Med.* 129:1307-26.
[41] Santos et al. (2001) *Clinical and Diagnostic Laboratory Immunology* 8:616-23.
[42] Frasch et al. (2009) *Vaccine* 27S:B112-6.
[43] Gennaro (2000) *Remington: The Science and Practice of Pharmacy.* 20th edition, ISBN: 0683306472.
[44] WO03/009869.
[45] *Vaccine Design* . . . (1995) eds. Powell & Newman. ISBN: 030644867X. Plenum.
[46] Tettelin et al. (2000) *Science* 287:1809-1815.
[47] WO00/66741.
[48] Martin et al. (1997) *J Exp Med* 185(7):1173-83.
[49] WO96/29412.
[50] Perkins-Balding et al. (2003) *Microbiology* 149:3423-35.
[51] WO01/55182.
[52] WO01/38350.
[53] WO00/23595.
[54] Giuliani et al. (2006) *Proc Natl Acad Sci USA.* 103: 10834-9.
[55] WO2004/032958.
[56] Costantino et al. (1992) *Vaccine* 10:691-698.
[57] Costantino et al. (1999) *Vaccine* 17:1251-1263.
[58] WO03/007985.
[59] Watson (2000) *Pediatr Infect Dis J*19:331-332.
[60] Rubin (2000) *Pediatr Clin North Am* 47:269-285, v.
[61] Jedrzejas (2001) *Microbiol Mol Biol Rev* 65:187-207.
[62] Bell (2000) *Pediatr Infect Dis J*19:1187-1188.
[63] Iwarson (1995) *APMIS* 103:321-326.
[64] Gerlich et al. (1990) *Vaccine* 8 Suppl:S63-68 & 79-80.
[65] *Vaccines* (1988) eds. Plotkin & Mortimer. ISBN 0-7216-1946-0.
[66] Del Guidice et al. (1998) *Molecular Aspects of Medicine* 19:1-70.
[67] Gustafsson et al. (1996) *N. Engl. J. Med.* 334:349-355.
[68] Rappuoli et al. (1991) *TIBTECH* 9:232-238.
[69] Sutter et al. (2000) *Pediatr Clin North Am* 47:287-308.
[70] Zimmerman & Spann (1999) *Am Fam Physician* 59:113-118, 125-126.
[71] McMichael (2000) *Vaccine* 19 Suppl 1:S101-107.
[72] Schuchat (1999) *Lancet* 353(9146):51-6.
[73] WO02/34771.
[74] Dale (1999) *Infect Dis Clin North Am* 13:227-43, viii.
[75] Ferretti et al. (2001) *PNAS USA* 98: 4658-4663.
[76] Kuroda et al. (2001) *Lancet* 357(9264):1225-1240; see also pages 1218-1219.
[77] Jones (2001) *Curr Opin Investig Drugs* 2:47-49.
[78] Ravenscroft et al. (1999) *Vaccine* 17:2802-2816.
[79] WO03/080678.
[80] *Research Disclosure,* 453077 (January 2002).
[81] EP-A-0372501.
[82] EP-A-0378881.
[83] EP-A-0427347.
[84] WO93/17712.
[85] WO94/03208.
[86] WO98/58668.
[87] EP-A-0471177.
[88] WO91/01146.
[89] Falugi et al. (2001) *Eur J Immunol* 31:3816-3824.
[90] Baraldo et al. (2004) *Infect Immun* 72(8):4884-7.
[91] EP-A-0594610.
[92] Ruan et al. (1990) *J Immunol* 145:3379-3384.
[93] WO00/56360.
[94] Kuo et al. (1995) *Infect Immun* 63:2706-13.

[95] Michon et al. (1998) *Vaccine.* 16:1732-41.
[96] WO02/091998.
[97] WO01/72337.
[98] WO00/61761.
[99] WO00/33882
[100] Lees et al. (1996) *Vaccine* 14:190-198.
[101] WO95/08348.
[102] U.S. Pat. No. 4,882,317
[103] U.S. Pat. No. 4,695,624
[104] Porro et al. (1985) *Mol Immunol* 22:907-919.s
[105] EP-A-0208375
[106] WO00/10599
[107] Gever et al. *Med. Microbiol. Immunol,* 165: 171-288 (1979).
[108] U.S. Pat. No. 4,057,685.
[109] U.S. Pat. Nos. 4,673,574; 4,761,283; 4,808,700.
[110] U.S. Pat. No. 4,459,286.
[111] U.S. Pat. No. 4,965,338
[112] U.S. Pat. No. 4,663,160.
[113] U.S. Pat. No. 4,761,283
[114] U.S. Pat. No. 4,356,170
[115] WO02/09643.
[116] Katial et al. (2002) *Infect Immun* 70:702-707.
[117] WO01/52885.
[118] European patent 0301992.
[119] Bjune et al. (1991) *Lancet* 338(8775):1093-1096.
[120] Frasch et al. (2001) chapter 7 of *Methods in Molecular Medicine,* volume 66 ('Meningococcal Vaccines: Methods and Protocols', eds. Pollard & Maiden).
[121] Fukasawa et al. (1999) *Vaccine* 17:2951-2958.
[122] WO02/09746.
[123] Rosenqvist et al. (1998) *Dev. Biol. Stand.* 92:323-333.
[124] European patent 0011243.
[125] Fredriksen et al. (1991) *NIPH Ann.* 14(2):67-80.
[126] WO01/91788.
[127] WO2004/019977.
[128] U.S. Pat. No. 6,558,677.
[129] WO01/09350.
[130] European patent 0449958.
[131] EP-A-0996712.
[132] EP-A-0680512.
[133] WO02/062378.
[134] WO99/59625.
[135] U.S. Pat. No. 6,180,111.
[136] WO01/34642.
[137] Peeters et al. (1996) *Vaccine* 14:1008-1015.
[138] Vermont et al. (2003) *Infect Immun* 71:1650-1655.
[139] WO2004/014417.
[140] WO2005/004908.
[141] WO2006/081259.
[142] WO98/56901.
[143] Claassen et al. (1996) 14(10):1001-8.
[144] WO99/10497.
[145] Steeghs et al. (2001) *The EMBO Journal* 20:6937-6945.
[146] Fisseha et al. (2005) *Infect Immun* 73:4070-80.
[147] WO00/25811.
[148] WO2004/015099.
[149] WO2004/046177.
[150] WO2006/046143.
[151] Adu-Bobie et al. (2004) *Infect Immun* 72:1914-19.
[152] WO2011/036562.
[153] Koeberling et al. (2014) *Vaccine* 32:2688-95.
[154] WO2013/033398.
[155] WO2013/113917.
[156] Needleman & Wunsch (1970) *J. Mol. Biol.* 48, 443-453.
[157] Rice et al. (2000) *Trends Genet* 16:276-277.
[158] WO01/64920.
[159] WO03/020756.
[160] WO2004/048404.
[161] WO2004/094596
[162] WO2006/024954.
[163] WO2007/060548.
[164] WO2009/104097.
[165] WO2013/132452.

```
                              SEQUENCE LISTING

>SEQ ID NO: 1  |MC58, v1|
MNRTAFCCLSLTTALILTACSSGGGGVAADIGAGLADALTAPLDHKDKGLQSLTLDQSVRKNE
KLKLAAQGAEKTYGNGDSLNTGKLKNDKVSRFDFIRQIEVDGQLITLESGEFQVYKQSHSALT
AFQTEQIQDSEHSGKMVAKRQFRIGDIAGEHTSFDKLPEGGRATYRGTAFGSDDAGGKLTYTI
DFAAKQGNGKIEHLKSPELNVDLAAADIKPDGKRHAVISGSVLYNQAEKGSYSLGIFGGKAQE
VAGSAEVKTVNGIRHIGLAAKQ

>SEQ ID NO: 2  |2996, v2|
MNRTAFCCLSLTAALILTACSSGGGGVAADIGAGLADALTAPLDHKDKSLQSLTLDQSVRKNE
KLKLAAQGAEKTYGNGDSLNTGKLKNDKVSRFDFIRQIEVDGQLITLESGEFQIYKQDHSAVV
ALQIEKINNPDKIDSLINQRSFLVSGLGGEHTAFNQLPDGKAEYHGKAFSSDDAGGKLTYTID
FAAKQGHGKIEHLKTPEQNVELAAAELKADEKSHAVILGDTRYGSEEKGTYHLALFGDRAQEI
AGSATVKIGEKVHEIGIAGKQ

>SEQ ID NO: 3  |M1239, v3|
MNRTAFCCLSLTTALILTACSSGGGGSGGGGVAADIGTGLADALTAPLDHKDKGLKSLTLEDS
IPQNGTLTLSAQGAEKTFKAGDKDNSLNTGKLKNDKISREDEVQKIEVDGQTITLASGEFQTY
KQNHSAVVALQIEKINNPDKTDSLINQRSFLVSGLGGEHTAFNQLPGGKAEYHGKAFSSDDPN
GRLHYSIDFTKKQGYGRIEHLKTLEQNVELAAAELKADEKSHAVILGDTRYGSEEKGTYHLAL
FGDRAQEIAGSATVKIGEKVHEIGIAGKQ

>SEQ ID NO: 4  |2996 mature|
CSSGGGGVAADIGAGLADALTAPLDHKDKSLQSLTLDQSVRKNEKLKLAAQGAEKTYGNGDSL
NTGKLKNDKVSRFDFIRQIEVDGQLITLESGEFQIYKQDHSAVVALQIEKINNPDKIDSLINQ
RSFLVSGLGGEHTAFNQLPDGKAEYHGKAFSSDDAGGKLTYTIDFAAKQGHGKIEHLKTPEQN
VELAAAELKADEKSHAVILGDTRYGSEEKGTYHLALFGDRAQEIAGSATVKIGEKVHEIGIAG
KQ >SEQ ID NO: 5  |2996 ΔG|
VAADIGAGLADALTAPLDHKDKSLQSLTLDQSVRKNEKLKLAAQGAEKTYGNGDSLNTGKLKN
DKVSRFDFIRQIEVDGQLITLESGEFQIYKQDHSAVVALQIEKINNPDKIDSLINQRSFLVSG
```

SEQUENCE LISTING

```
LGGEHTAFNQLPDGKAEYHGKAFSSDDAGGKLTYTIDFAAKQGHGKIEHLKTPEQNVELAAAE
LKADEKSHAVILGDTRYGSEEKGTYHLALFGDRAQEIAGSATVKIGEKVHEIGIAGKQ

>SEQ ID NO: 6 |NHBA|
MFKRSVIAMACIFALSACGGGGGGSPDVKSADTLSKPAAPVVSEKETEAKEDAPQAGSQGQGA
PSAQGSQDMAAVSEENTGNGGAVTADNPKNEDEVAQNDMPQNAAGTDSSTPNHTPDPNMLAGN
MENQATDAGESSQPANQPDMANAADGMQGDDPSAGGQNAGNTAAQGANQAGNNQAAGSSDPIP
ASNPAPANGGSNFGRVDLANGVLIDGPSQNITLTHCKGDSCSGNNFLDEEVQLKSEFEKLSDA
DKISNYKKDGKNDKFVGLVADSVQMKGINQYIIFYKPKPTSFARFRRSARSRRSLPAEMPLIP
VNQADTLIVDGEAVSLTGHSGNIFAPEGNYRYLTYGAEKLPGGSYALRVQGEPAKGEMLAGAA
VYNGEVLHFHTENGRPYPTRGRFAAKVDEGSKSVDGIIDSGDDLHMGTQKFKAAIDGNGFKGT
WTENGSGDVSGKFYGPAGEEVAGKYSYRPTDAEKGGFGVFAGKKEQD

>SEQ ID NO: 7 |NadA|
MSMKHFPSKVLTTAILATFCSGALAATSDDDVKKAATVAIVAAYNNGQEINGFKAGETIYDIG
EDGTITQKDATAADVEADDFKGLGLKKVVTNLTKTVNENKQNVDAKVKAAESEIEKLTTKLAD
TDAALADTDAALDETTNALNKLGENITTFAEETKTNIVKIDEKLEAVADTVDKHAEAFNDIAD
SLDETNTKADEAVKTANEAKQTAEETKQNVDAKVKAAETAAGKAEAAAGTANTAADKAEAVAA
KVTDIKADIATNKADIAKNSARIDSLDKNVANLRKETRQGLAEQAALSGLFQPYNVGRENVTA
AVGGYKSESAVAIGTGFRFTENFAAKGAVAVGTSSGSSAAYHVGVNYEW

>SEQ ID NO: 8 |NspA|
MKKALATLIALALPAAALAEGASGFYVQADAAHAKASSSLGSAKGFSPRISAGYRINDLRFAV
DYTRYKNYKAPSTDFKLYSIGASAIYDFDTQSPVKPYLGARLSLNRASVDLGGSDSFSQTSIG
LGVLTGVSYAVTPNVDLDAGYRYNYIGKVNTVKNVRSGELSAGVRVKF

>SEQ ID NO: 9 |HmbR|
MKPLQMLPIAALVGSIFGNPVLAADEAATETTPVKAEIKAVRVKGQRNAPAAVERVNLNRIKQ
EMIRDNKDLVRYSTDVGLSDSGRHQKGFAVRGVEGNRVGVSIDGVNLPDSEENSLYARYGNFN
SSRLSIDPELVRNIEIVKGADSFNTGSGALGGGVNYQTLQGRDLLLDDRQFGVMMKNGYSTRN
REWTNTLGFGVSNDRVDAALLYSQRRGHETESAGNRGYAVEGEGSGANIRGSARGIPDSSKHK
YNHHALGKIAYQINDNHRIGASLNGQQGHNYTVEESYNLTASSWREADDVNRRRNANLFYEWM
PDSNWLSSLKADFDYQKTKVAAVNNKGSFPMDYSTWTRNYNQKDLDEIYNRSMDTRFKRFTLR
LDSHPLQLGGGRHRLSFKTFVSRRDFENLNRDDYYFSGRVVRTTSSIQHPVKTTNYGFSLSDQ
IQWNDVFSSRAGIRYDHTKMTPQELNAECHACDKTPPAANTYKGWSGFVGLAAQLNQAWRVGY
DITSGYRVPNASEVYFTYNHGSGNWLPNPNLKAERSTTHTLSLQGRSEKGMLDANLYQSNYRN
FLSEEQKLTTSGTPGCTEENAYYGICSDPYKEKLDWQMKNIDKARIRGIELTGRLNVDKVASF
VPEGWKLFGSLGYAKSKLSGDNSLLSTQPLKVIAGIDYESPSEKWGVFSRLTYLGAKKVKDAQ
YTVYENKGWGTPLQKKVKDYPWLNKSAYVFDMYGFYKPAKNLTLRAGVYNLFNRKYTTWDSLR
GLYSYSTTNAVDRDGKGLDRYRAPGRNYAVSLEWKF

>SEQ ID NO: 10 |NhhA|
MNKIYRIIWNSALNAWVVVSELTRNHTKRASATVKTAVLATLLFATVQASANNEEQEEDLYLD
PVQRTVAVLIVNSDKEGTGEKEKVEENSDWAVYFNEKGVLTAREITLKAGDNLKIKQNGTNFT
YSLKKDLTDLTSVGTEKLSFSANGNKVNITSDTKGLNFAKETAGTNGDTTVHLNGIGSTLTDT
LLNTGATTNVTNDNVTDDEKKRAASVKDVLNAGWNIKGVKPGTTASDNVDFVRTYDTVEFLSA
DTKTTTVNVESKDNGKKTEVKIGAKTSVIKEKDGKLVTGKDKGENGSSTDEGEGLVTAKEVID
AVNKAGWRMKTTTANGQTGQADKFETVTSGTNVTFASGKGTTATVSKDDQGNITVMYDVNVGD
ALNVNQLQNSGWNLDSKAVAGSSGKVISGNVSPSKGKMDETVNINAGNNIEITRNGKNIDIAT
SMTPQFSSVSLGAGADAPTLSVDGDALNVGSKKDNKPVRITNVAPGVKEGDVTNVAQLKGVAQ
NLNNRIDNVDGNARAGIAQAIATAGLVQAYLPGKSMMAIGGGTYRGEAGYAIGYSSISDGGNW
IIKGTASGNSRGHFGASASVGYQW

>SEQ ID NO: 11 |App|
MKTTDKRTTETHRKAPKTGRIRFSPAYLAICLSFGILPQAWAGHTYFGINYQYYRDFAENKGK
FAVGAKDIEVYNKKGELVGKSMTKAPMIDFSVVSRNGVAALVGDQYIVSVAHNGGYNNVDFGA
EGRNPDQHRFTYKIVKRNNYKAGTKGHPYGGDYHMPRLHKEVTDAEPVEMTSYMDGRKYIDQN
NYPDRVRIGAGRQYWRSDEDEPNNRESSYHIASAYSWLVGPNTFAQNGSGGGTVNLGSEKIKH
SPYGFLPTGGSFGDSGSPMFIYDAQKQKWLINGVLQTGNPYIGKSNGFQLVRKDWFYDEIFAG
DTHSVFYEPRQNGKYSENDDNNGTGKINAKHEHNSLPNRLKTRTVQLENVSLSETAREPVYHA
AGGVNSYRPRLNNGENISFIDEGKGELILTSNINQGAGGLYFQGDFTVSPENNETWQGAGVHI
SEDSTVTWKVNGVANDRLSKIGKGTLHVQAKGENQGSISVGDGTVILDQQADDKGKKQAFSEI
GLVSGRGTVQLNADNQFNPDKLYFGERGGRLDLNGHSLSFHRIQNTDEGAMIVNHNQDKESTV
TITGNKDIATTGNNNSLDSKKEIAYNGWFGEKDTTKTNGRLNLVYQPAAEDRTLLLSGGTNLN
GNITQTNGKLFFSGRPTPHAYNHLNDHWSQKEGIPRGEIVWDNDWINRTFKAENFQIKGGQAV
VSRNVAKVKGDWHLSNHAQAVFGVAPHQSHTICTRSDWTGLTNCVEKTITDDKVIASLTKTDI
SGNVDLADHAHLNLTGLATLNGNLSANGDTRYTVSHNATQNGNLSLVGNAQATFNQATLNGNT
SASGNASFNLSDHAVQNGSLTLSGNAKANVSHSALNGNVSLADKAVFHFESSRFTGQISGGKD
TALHLKDSEWTLPSGTELGNLNLDNATITLNSAYRHDAAGAQTGSATDAPRRRSRRSRRSLLS
VTPPTSVESRFNTLTVNGKLNGQGTFRFMSELFGYRSDKLKLAESSEGTYTLAVNNTGNEPAS
LEQLTVVEGKDNKPLSENLNFTLQNEHVDAGAWRYQLIRKDGEFRLHNPVKEQELSDKLGKAE
AKKQAEKDNAQSLDALIAAGRDAVEKTESVAEPARQAGGENVGIMQAEEEKKRVQADKDTALA
KQREAETRPATTAFPRARRARRDLPQLQPQPQPQRDLISRYANSGLSEFSATLNSVFAVQD
ELDRVFAEDRRNAVWTSGIRDTKHYRSQDFRAYRQQTDLRQIGMQKNLGSGRVGILESHNRTE
```

```
                        SEQUENCE LISTING

NTFDDGIGNSARLAHGAVFGQYGIDRFYIGISAGAGFSSGSLSDGIGGKIRRRVLHYGIQARY
RAGEGGEGIEPHIGATRYFVQKADYRYENVNIATPGLAFNRYRAGIKADYSFKPAQHISITPY
LSLSYTDAASGKVRTRVNTAVLAQDFGKTRSAEWGVNAEIKGFTLSLHAAAAKGPQLEAQHSA
GIKLGYRW

>SEQ ID NO: 12 |Omp85|
MKLKQIASALMMLGISPLALADFTIQDIRVEGLQRTEPSTVFNYLPVKVGDTYNDTHGSAIIK
SLYATGEFDDVRVETADGQLLLTVIERPTIGSLNITGAKMLQNDAIKKNLESFGLAQSQYFNQ
ATLNQAVAGLKEEYLGRGKLNIQITPKVTKLARNRVDIDITIDEGKSAKITDIEFEGNQVYSD
RKLMRQMSLTEGGIWTWLTRSNQFNEQKFAQDMEKVTDFYQNNGYFDFRILDTDIQTNEDKTK
QTIKITVHEGGRFRWGKVSIEGDTNEVPKAELEKLLTMKPGKWYERQQMTAVLGEIQNRMGSA
GYAYSEISVQPLPNAETKTVDFVLHIEPGRKIYVNEIHITGNNKTRDEVVRRELRQMESAPYD
TSKLQRSKERVELLGYFDNVQFDAVPLAGTPDKVDLNMSLTERSTGSLDLSAGWVQDTGLVMS
AGVSQDNLFGTGKSAALRASRSKTTLNGSLSFTDPYFTADGVSLGYDVYGKAFDPRKASTSIK
QYKTTTAGAGIRMSVPVTEYDRVNEGLVAEHLTVNTYNKAPKHYADFIKKYGKTDGTDGSFKG
WLYKGTVGWGRNKTDSALWPTRGYLTGVNAEIALPGSKLQYYSATHNQTWFFPLSKTFTLMLG
GEVGIAGGYGRTKEIPFFENFYGGGLGSVRGYESGTLGPKVYDEYGEKISYGGNKKANVSAEL
LFPMPGAKDARTVRLSLFADAGSVWDGKTYDDNSSSATGGRVQNIYGAGNTHKSTFTNELRYS
AGGAVTWLSPLGPMKFSYAYPLKKKPEDEIQRFQFQLGTTF

>SEQ ID NO: 13 |NMB2091|
MVSAVIGSAAVGAKSAVDRRTTGAQTDDNVMALRIETTARSYLRQNNQTKGYTPQISVVGYDR
HLLLLGQVATEGEKQFVGQIARSEQAAEGVYNYITVASLPRTAGDIAGDTWNTSKVRATLLGI
SPATRARVKIVTYGNVTYVMGILTPEEQAQITQKVSTTVGVQKVITLYQNYVQR

>SEQ ID NO: 14 |NHBA fusion|
MASPDVKSADTLSKPAAPVVSEKETEAKEDAPQAGSQGQGAPSAQGGQDMAAVSEENTGNGGA
AATDKPKNEDEGAQNDMPQNAADTDSLTPNHTPASNMPAGNMENQAPDAGESEQPANQPDMAN
TADGMQGDDPSAGGENAGNTAAQGTNQAENNQTAGSQNPASSTNPSATNSGGDFGRTNVGNSV
VIDGPSQNITLTHCKGDSCSGNNFLDEEVQLKSEFEKLSDADKISNYKKDGKNDGKNDKFVGL
VADSVQMKGINQYIIFYKPKPTSFARFRRSARSRRSLPAEMPLIPVNQADTLIVDGEAVSLTG
HSGNIFAPEGNYRYLTYGAEKLPGGSYALRVQGEPSKGEMLAGTAVYNGEVLHFHTENGRPSP
SRGRFAAKVDFGSKSVDGIIDSGDGLHMGTQKFKAAIDGNGFKGTWTENGGGDVSGKFYGPAG
EEVAGKYSYRPTDAEKGGEGVFAGKKEQDGSGGGGATYKVDEYHANARFAIDHENTSTNVGGF
YGLTGSVEFDQAKRDGKIDITIPVANLQSGSQHFTDHLKSADIFDAAQYPDIREVSTKENENG
KKLVSVDGNLTMHGKTAPVKLKAEKFNCYQSPMAKTEVCGGDFSTTIDRTKWGVDYLVNVGMT
KSVRIDIQIEAAKQ >SEQ ID NO: 15 |NadA fragment|
ATNDDDVKKAATVAIAAAYNNGQEINGFKAGETIYDIDEDGTITKKDATAADVEADDFKGLGL
KKVVTNLTKTVNENKQNVDAKVKAAESEIEKLTTKLADTDAALADTDAALDATTNALNKLGEN
ITTFAEETKTNIVKIDEKLEAVADTVDKHAEAFNDIADSLDETNTKADEAVKTANEAKQTAEE
TKQNVDAKVKAAETAAGKAEAAAGTANTAADKAEAVAAKVTDIKADIATNKDNIAKKANSADV
YTREESDSKFVRIDGLNATTEKLDTRLASAEKSIADHDTRLNGLDKTVSDLRKETRQGLAEQA
ALSGLFQPYNVG >SEQ ID NO: 16 |MC58, ΔG|
VAADIGAGLADALTAPLDHKDKGLQSLTLDQSVRKNEKLKLAAQGAEKTYGNGDSLNTGKLKN
DKVSRFDFIRQIEVDGQLITLESGEFQVYKQSHSALTAFQTEQIQDSEHSGKMVAKRQFRIGD
IAGEHTSFDKLPEGGRATYRGTAFGSDDAGGKLTYTIDFAAKQGNGKIEHLKSPELNVDLAAA
DIKPDGKRHAVISGSVLYNQAEKGSYSLGIFGGKAQEVAGSAEVKTVNGIRHIGLAAKQ >SEQ ID NO: 17|M1239, AG|
VAADIGTGLADALTAPLDHKDKGLKSLTLEDSIPQNGTLTLSAQGAEKTFKAGDKDNSLNTGK
LKNDKISREDEVQKIEVDGQTITLASGEFQIYKQNHSAVVALQIEKINNPDKTDSLINQRSFL
VSGLGGEHTAFNQLPGGKAEYHGKAFSSDDPNGRLHYSIDFTKKQGYGRIEHLKTLEQNVELA
AAELKADEKSHAVILGDTRYGSEEKGTYHLALFGDRAQEIAGSATVKIGEKVHEIGIAGKQ >SEQ ID NO: 18 |'wild-type' fusion|
MGPDSDRLQQRRVAADIGAGLADALTAPLDHKDKSLQSLTLDQSVRKNEKLKLAAQGAEKTYG
NGDSLNTGKLKNDKVSRFDFIRQIEVDGQLITLESGEFQIYKQDHSAVVALQIEKINNPDKID
SLINQRSFLVSGLGGEHTAFNQLPDGKAEYHGKAFSSDDAGGKLTYTIDFAAKQGHGKIEHLK
TPEQNVELAAAELKADEKSHAVILGDTRYGSEEKGTYHLALFGDRAQEIAGSATVKIGEKVHE
IGIAGKQGSGPDSDRLQQRRVAADIGTGLADALTAPLDHKDKGLKSLTLEDSIPQNGTLTLSA
QGAEKTFKAGDKDNSLNTGKLKNDKISREDEVQKIEVDGQTITLASGEFQIYKQNHSAVVALQ
IEKINNPDKTDSLINQRSFLVSGLGGEHTAFNQLPGGKAEYHGKAFSSDDPNGRLHYSIDFTK
KQGYGRIEHLKTLEQNVELAAAELKADEKSHAVILGDTRYGSEEKGTYHLALFGDRAQEIAGS
ATVKIGEKVHEIGIAGKQGSGGGGVAADIGAGLADALTAPLDHKDKGLQSLTLDQSVRKNEKL
KLAAQGAEKTYGNGDSLNTGKLKNDKVSRFDFIRQIEVDGQLITLESGEFQVYKQSHSALTAF
QTEQIQDSEHSGKMVAKRQFRIGDIAGEHTSFDKLPEGGRATYRGTAFGSDDAGGKLTYTIDF
AAKQGNGKIEHLKSPELNVDLAAADIKPDGKRHAVISGSVLYNQAEKGSYSLGIFGGKAQEVA
GSAEVKTVNGIRHIGLAAKQ >SEQ ID NO: 19 |S58V/L149R mutant v2|
MNRTAFCCLSLTAALILTACSSGGGGVAADIGAGLADALTAPLDHKDKSLQSLTLDQVVRKNE
KLKLAAQGAEKTYGNGDSLNTGKLKNDKVSRFDFIRQIEVDGQLITLESGEFQIYKQDHSAVV
ALQIEKINNPDKIDSLINQRSFRVSGLGGEHTAFNQLPDGKAEYHGKAFSSDDAGGKLTYTID
```

SEQUENCE LISTING

```
FAAKQGHGKIEHLKTPEQNVELAAAELKADEKSHAVILGDTRYGSEEKGTYHLALFGDRAQEI
AGSATVKIGEKVHEIGIAGKQ

>SEQ ID NO: 20 |linker|
GSGGGG

>SEQ ID NO: 21 |linker|
GPDSDRLQQRR

>SEQ ID NO: 22 |linker|
GSGPDSDRLQQRR

>SEQ ID NO: 23 |linker|
GKGPDSDRLQQRR

>SEQ ID NO: 24 |N-terminal sequence|
MGPDSDRLQQRR

>SEQ ID NO: 25 |N-terminal sequence|
MAS

>SEQ ID NO: 26 |linker|
LEHHHHHH

>SEQ ID NO: 27 |mutant 2-3-1 sequence, A|
MGPDSDRLQQRRVAADIGAGLADALTAPLDHKDKSLQSLTLDQVVRKNEKLKLAAQGAEKTYG
NGDSLNTGKLKNDKVSRFDFIRQIEVDGQLITLESGEFQIYKQDHSAVVALQIEKINNPDKID
SLINQRSFRVSGLGGEHTAFNQLPDGKAEYHGKAFSSDDAGGKLTYTIDFAAKQGHGKIEHLK
TPEQNVELAAAELKADEKSHAVILGDTRYGSEEKGTYHLALFGDRAQEIAGSATVKIGEKVHA
IGIAGKQGSGGGGVAADIGTGLADALTAPLDHKDKGLKSLTLEDVIPQNGTLTLSAQGAEKTF
KAGDKDNSLNTGKLKNDKISREDEVQKIEVDGQTITLASGEFQIYKQNHSAVVALQIEKINNP
DKTDSLINQRSFRVSGLGGEHTAFNQLPGGKAEYHGKAFSSDDPNGRLHYSIDFTKKQGYGRI
EHLKTLEQNVELAAAELKADEKSHAVILGDTRYGSEEKGTYHLALFGDRAQEIAGSATVKIGE
KVHAIGIAGKQGSGGGGVAADIGAGLADALTAPLDHKDKGLQSLTLDQSVSKNEKLKLAAQGA
EKTYGNGDSLNTGKLKNDKVSRFDFIRQIEVDGQLITLESGEFQVYKQSHSALTAFQTEQIQD
SEHSGKMVAKRQFRIGDIAGEHTSFDKLPEGGRATYRGTAFGSDDAGGKLTYTIDFAAKQGNG
KIEHLKSPELNVDLAAADIKPDGKRHAVISGSVLYNQAEKGSYSLGIFGGKAQEVAGSAEVKT
VNGIRHIGLAAKQ >SEQ ID NO: 28 |mutant 2-3-1 sequence, A, without leader|
VAADIGAGLADALTAPLDHKDKSLQSLTLDQVVRKNEKLKLAAQGAEKTYGNGDSLNTGKLKN
DKVSRFDFIRQIEVDGQLITLESGEFQIYKQDHSAVVALQIEKINNPDKIDSLINQRSFRVSG
LGGEHTAFNQLPDGKAEYHGKAFSSDDAGGKLTYTIDFAAKQGHGKIEHLKTPEQNVELAAAE
LKADEKSHAVILGDTRYGSEEKGTYHLALFGDRAQEIAGSATVKIGEKVHAIGIAGKQGSGGG
GVAADIGTGLADALTAPLDHKDKGLKSLTLEDVIPQNGTLTLSAQGAEKTFKAGDKDNSLNTG
KLKNDKISREDEVQKIEVDGQTITLASGEFQIYKQNHSAVVALQIEKINNPDKTDSLINQRSF
RVSGLGGEHTAFNQLPGGKAEYHGKAFSSDDPNGRLHYSIDFTKKQGYGRIEHLKTLEQNVEL
AAAELKADEKSHAVILGDTRYGSEEKGTYHLALFGDRAQEIAGSATVKIGEKVHAIGIAGKQG
SGGGGVAADIGAGLADALTAPLDHKDKGLQSLTLDQSVSKNEKLKLAAQGAEKTYGNGDSLNT
GKLKNDKVSRFDFIRQIEVDGQLITLESGEFQVYKQSHSALTAFQTEQIQDSEHSGKMVAKRQ
FRIGDIAGEHTSFDKLPEGGRATYRGTAFGSDDAGGKLTYTIDFAAKQGNGKIEHLKSPELNV
DLAAADIKPDGKRHAVISGSVLYNQAEKGSYSLGIFGGKAQEVAGSAEVKTVNGIRHIGLAAK
Q >SEQ ID NO: 29 |mutant 2-3-1 sequence, B|
MGPDSDRLQQRRVAADIGAGLADALTAPLDHKDKSLQSLTLDQVVRKNEKLKLAAQGAEKTYG
NGDSLNTGKLKNDKVSRFDFIRQIEVDGQLITLESGEFQIYKQDHSAVVALQIEKINNPDKID
SLINQRSFRVSGLGGEHTAFNQLPDGKAEYHGKAFSSDDAGGKLTYTIDFAAKQGHGKIEHLK
TPEQNVELAAAELKADEKSHAVILGDTRYGSEEKGTYHLALFGDRAQEIAGSATVKIGEKVHE
IGIAGKQGSGGGGVAADIGTGLADALTAPLDHKDKGLKSLTLEDVIPQNGTLTLSAQGAEKTF
KAGDKDNSLNTGKLKNDKISREDEVQKIEVDGQTITLASGEFQIYKQNHSAVVALQIEKINNP
DKTDSLINQRSFRVSGLGGEHTAFNQLPGGKAEYHGKAFSSDDPNGRLHYSIDFTKKQGYGRI
EHLKTLEQNVELAAAELKADEKSHAVILGDTRYGSEEKGTYHLALFGDRAQEIAGSATVKIGE
KVHEIGIAGKQGSGGGGVAADIGAGLADALTAPLDHKDKGLQSLTLDQSVSKNEKLKLAAQGA
EKTYGNGDSLNTGKLKNDKVSRFDFIRQIEVDGQLITLESGEFQVYKQSHSALTAFQTEQIQD
SEHSGKMVAKRQFRIGDIAGEHTSFDKLPEGGRATYRGTAFGSDDAGGKLTYTIDFAAKQGNG
KIEHLKSPELNVDLAAADIKPDGKRHAVISGSVLYNQAEKGSYSLGIFGGKAQEVAGSAEVKT
VNGIRHIGLAAKQ >SEQ ID NO: 30 |mutant 2-3-1 sequence, B, without leader|
VAADIGAGLADALTAPLDHKDKSLQSLTLDQVVRKNEKLKLAAQGAEKTYGNGDSLNTGKLKN
DKVSRFDFIRQIEVDGQLITLESGEFQIYKQDHSAVVALQIEKINNPDKIDSLINQRSFRVSG
LGGEHTAFNQLPDGKAEYHGKAFSSDDAGGKLTYTIDFAAKQGHGKIEHLKTPEQNVELAAAE
LKADEKSHAVILGDTRYGSEEKGTYHLALFGDRAQEIAGSATVKIGEKVHEIGIAGKQGSGGG
GVAADIGTGLADALTAPLDHKDKGLKSLTLEDVIPQNGTLTLSAQGAEKTFKAGDKDNSLNTG
KLKNDKISREDEVQKIEVDGQTITLASGEFQIYKQNHSAVVALQIEKINNPDKTDSLINQRSF
RVSGLGGEHTAFNQLPGGKAEYHGKAFSSDDPNGRLHYSIDFTKKQGYGRIEHLKTLEQNVEL
```

SEQUENCE LISTING

```
AAAELKADEKSHAVILGDTRYGSEEKGTYHLALFGDRAQEIAGSATVKIGEKVHEIGIAGKQG
SGGGGVAADIGAGLADALTAPLDHKDKGLQSLTLDQSVSKNEKLKLAAQGAEKTYGNGDSLNT
GKLKNDKVSRFDFIRQIEVDGQLITLESGEFQVYKQSHSALTAFQTEQIQDSEHSGKMVAKRQ
FRIGDIAGEHTSFDKLPEGGRATYRGTAFGSDDAGGKLTYTIDFAAKQGNGKIEHLKSPELNV
DLAAADIKPDGKRHAVISGSVLYNQAEKGSYSLGIFGGKAQEVAGSAEVKTVNGIRHIGLAAK
Q

>SEQ ID NO: 31 |mutant v2, Xaa 32 is any amino acid, Xaa 123 is not L|
VAADIGAGLADALTAPLDHKDKSLQSLTLDQXVRKNEKLKLAAQGAEKTYGNGDSLNTGKLKN
DKVSRFDFIRQIEVDGQLITLESGEFQIYKQDHSAVVALQIEKINNPDKIDSLINQRSFXVSG
LGGEHTAFNQLPDGKAEYHGKAFSSDDAGGKLTYTIDFAAKQGHGKIEHLKTPEQNVELAAAE
LKADEKSHAVILGDTRYGSEEKGTYHLALFGDRAQEIAGSATVKIGEKVHEIGIAGKQ >SEQ ID NO: 32 |mutant v3, Xaa 32 is any amino acid, Xaa 126 is not L|
VAADIGTGLADALTAPLDHKDKGLKSLTLEDXIPQNGTLTLSAQGAEKTFKAGDKDNSLNTGK
LKNDKISRFDFVQKIEVDGQTITLASGEFQIYKQNHSAVVALQIEKINNPDKTDSLINQRSFX
VSGLGGEHTAFNQLPGGKAEYHGKAFSSDDPNGRLHYSIDFTKKQGYGRIEHLKTLEQNVELA
AAELKADEKSHAVILGDTRYGSEEKGTYHLALFGDRAQEIAGSATVKIGEKVHEIGIAGKQ >SEQ ID NO: 33 |v2, 8047 strain, wild-type|
MNRTAFCCLSLTTALILTACSSGGGGVAADIGARLADALTAPLDHKDKSLQSLTLDQSVRKNE
KLKLAAQGAEKTYGNGDSLNTGKLKNDKVSRFDFIRQIEVDGQLITLESGEFQIYKQDHSAVV
ALQIEKINNPDKIDSLINQRSFLVSGLGGEHTAFNQLPDGKAEYHGKAFSSDDAGGKLTYTID
FAAKQGHGKIEHLKTPEQNVELAAAELKADEKSHAVILGDTRYGSEEKGTYHLALFGDRAQEI
AGSATVKIGEKVHEIGIAGKQ >SEQ ID NO: 34 |v2, 8047 strain, AG|
VAADIGARLADALTAPLDHKDKSLQSLTLDQSVRKNEKLKLAAQGAEKTYGNGDSLNTGKLKN
DKVSRFDFIRQIEVDGQLITLESGEFQIYKQDHSAVVALQIEKINNPDKIDSLINQRSFLVSG
LGGEHTAFNQLPDGKAEYHGKAFSSDDAGGKLTYTIDFAAKQGHGKIEHLKTPEQNVELAAAE
LKADEKSHAVILGDTRYGSEEKGTYHLALFGDRAQEIAGSATVKIGEKVHEIGIAGKQ >SEQ ID NO: 35 |wild-type v2 for mutagenesis e.g. for GMMA approach|
VAADIGARLADALTAPLDHKDKSLQSLTLDQSVRKNEKLKLAAQGAEKTYGNGDSLNTGKLKN
DKVSRFDFIRQIEVDGQLITLESGEFQIYKQDHSAVVALQIEKINNPDKIDSLINQRSFLVSG
LGGEHTAFNQLPDGKAEYHGKAFSSDDAGGKLTYTIDFAAKQGHGKIEHLKTPEQNVELAAAE
LKADEKSHAVILGDTRYGSEEKGTYHLALFGDRAQEIAGSATVKIGEKVHEIGIAGKQ >SEQ ID NO: 36 |wild-type v3 for mutagenesis e.g. for GMMA approach|
VAADIGAGLADALTAPLDHKDKGLQSLTLDQSVRKNEKLKLAAQGAEKTYGNGDSLNTGKLKN
DKVSRFDFIRQIEVDGKLITLESGEFQVYKQSHSALTALQTEQVQDSEDSGKMVAKRQFRIGD
IAGEHTSFDKLPKGGSATYRGTAFGSDDAGGKLTYTIDFAAKQGHGKIEHLKSPELNVELATA
ELKADEKSHAVILGDTRYGGEEKGTYHLALFGDRAQEIAGSATVKIREKVHEIGIAGKQ >SEQ ID NO:37: variant fHbp v3 from N. meningitidis where residue 32 is
not S, residue 126 not L
VAADIGTGLA DALTAPLDHK DKGLKSLTLE DXIPQNGTLT LSAQGAEKTF KAGDKDNSLN    60
TGKLKNDKIS RFDFVQKIEV DGQTITLASG EFQIYKQNHS AVVALQIEKI NNPDKTDSLI   120
NQRSFXVSGL GGEHTAFNQL PGGKAEYHGK AFSSDDPNGR LHYSIDFTKK QGYGRIEHLK   180
TLEQNVELAA AELKADEKSH AVILGDTRYG SEEKGTYHLA LFGDRAQEIA GSATVKIGEK   240
VHEIGIAGKQ >SEQ ID NO:38: fHbp v3 from N. meningitidis where residue 32
is not S, residue 123 is not L, residue 240 is not E
VAADIGAGLA DALTAPLDHK DKSLQSLTLD QXVRKNEKLK LAAQGAEKTY GNGDSLNTGK    60
LKNDKVSRFD FIRQIEVDGQ LITLESGEFQ IYKQDHSAVV ALQIEKINNP DKIDSLINQR   120
SFXVSGLGGE HTAFNQLPDG KAEYHGKAFS SDDAGGKLTY TIDFAAKQGH GKIEHLKTPE   180
QNVELAAAEL KADEKSHAVI LGDTRYGSEE KGTYHLALFG DRAQEIAGSA TVKIGEKVHX   240
IGIAGKQ >SEQ ID NO: 39 |fHbp variant v2, where residue 32 is not S, residue 123 is
not L, residue 240 is not E|
CSSGGGGSGG GGVAADIGTG LADALTAPLD HXDKGLKSLT LEDSIPQNGT LTLSAQGAEK    60
TFKAGDKDNS LNTGKLKNDK ISRFDFVQKI EVDGQTITLA SGEFQIYKQN HSAVVALQIE   120
KIXNPDKTDS LINQRSFLVS GLGGEHTAFN QLPGGKAEYH GKAFSSDDPN GRLHYSIDFT   180
KKQGYGRIEH LKTLEQNVEL AAAELKADEK SHAVILGDIR YGSEEKGTYH LALFGDRAQX   240
IAGSATVKIG EKVHEIGIAG KQ >SEQ ID NO: 40 |M1239, mature|
CSSGGGGSGGGGVAADIGTGLADALTAPLDHKDKGLKSLTLEDSIPQNGTLTLSAQGAEKTFK
AGDKDNSLNTGKLKNDKISRFDFVQKIEVDGQTITLASGEFQIYKQNHSAVVALQIEKINNPD
KTDSLINQRSFLVSGLGGEHTAFNQLPGGKAEYHGKAFSSDDPNGRLHYSIDFTKKQGYGRIE
HLKTLEQNVELAAAELKADEKSHAVILGDTRYGSEEKGTYHLALFGDRAQEIAGSATVKIGEK
VHEIGIAGKQ
```

SEQUENCE LISTING

```
>SEQ ID NO: 41 |M1239, E243A, ΔG|
VAADIGTGLADALTAPLDHKDKGLKSLTLEDSIPQNGTLTLSAQGAEKTFKAGDKDNSLNTGK
LKNDKISRFDFVQKIEVDGQTITLASGEFQIYKQNHSAVVALQIEKINNPDKTDSLINQRSFL
VSGLGGEHTAFNQLPGGKAEYHGKAFSSDDPNGRLHYSIDFTKKQGYGRIEHLKTLEQNVELA
AAELKADEKSHAVILGDTRYGSEEKGTYHLALFGDRAQEIAGSATVKIGEKVHAIGIAGKQ

>SEQ ID NO: 42 |M1239, S32V + E243A, ΔG|
VAADIGTGLADALTAPLDHKDKGLKSLTLEDVIPQNGTLTLSAQGAEKTFKAGDKDNSLNTGK
LKNDKISRFDFVQKIEVDGQTITLASGEFQIYKQNHSAVVALQIEKINNPDKTDSLINQRSFL
VSGLGGEHTAFNQLPGGKAEYHGKAFSSDDPNGRLHYSIDFTKKQGYGRIEHLKTLEQNVELA
AAELKADEKSHAVILGDTRYGSEEKGTYHLALFGDRAQEIAGSATVKIGEKVHAIGIAGKQ

>SEQ ID NO: 43 |M1239, S32V + L126R + E243A, ΔG|
VAADIGTGLADALTAPLDHKDKGLKSLTLEDVIPQNGTLTLSAQGAEKTFKAGDKDNSLNTGK
LKNDKISRFDFVQKIEVDGQTITLASGEFQIYKQNHSAVVALQIEKINNPDKTDSLINQRSFR
VSGLGGEHTAFNQLPGGKAEYHGKAFSSDDPNGRLHYSIDFTKKQGYGRIEHLKTLEQNVELA
AAELKADEKSHAVILGDTRYGSEEKGTYHLALFGDRAQEIAGSATVKIGEKVHAIGIAGKQ

>SEQ ID NO: 44 |M1239, S32V + L126R, ΔG|
VAADIGTGLADALTAPLDHKDKGLKSLTLEDVIPQNGTLTLSAQGAEKTFKAGDKDNSLNTGK
LKNDKISRFDFVQKIEVDGQTITLASGEFQIYKQNHSAVVALQIEKINNPDKTDSLINQRSFR
VSGLGGEHTAFNQLPGGKAEYHGKAFSSDDPNGRLHYSIDFTKKQGYGRIEHLKTLEQNVELA
AAELKADEKSHAVILGDTRYGSEEKGTYHLALFGDRAQEIAGSATVKIGEKVHEIGIAGKQ

>SEQ ID NO: 45 |v2 MUTANT|
VAADIGAGLADALTAPLDHKDKSLQSLTLDQVVRKNEKLKLAAQGAEKTYGNGDSLNTGKLKN
DKVSRFDFIRQIEVDGQLITLESGEFQIYKQDHSAVVALQIEKINNPDKIDSLINQRSFRVSG
LGGEHTAFNQLPDGKAEYHGKAFSSDDAGGKLTYTIDFAAKQGHGKIEHLKTPEQNVELAAAE
LKADEKSHAVILGDTRYGSEEKGTYHLALFGDRAQEIAGSATVKIGEKVHEIGIAGKQ

>SEQ ID NO: 46 |MC58, v1, mature|
CSSGGGGVAADIGAGLADALTAPLDHKDKGLQSLTLDQSVRKNEKLKLAAQGAEKTYGNGDSL
NTGKLKNDKVSRFDFIRQIEVDGQLITLESGEFQVYKQSHSALTAFQTEQIQDSEHSGKMVAK
RQFRIGDIAGEHTSFDKLPEGGRATYRGTAFGSDDAGGKLTYTIDFAAKQGNGKIEHLKSPEL
NVDLAAADIKPDGKRHAVISGSVLYNQAEKGSYSLGIFGGKAQEVAGSAEVKTVNGIRHIGLA
AKQ >SEQ ID NO: 47 |mutant v2, Xaa 32 is any amino acid, 123 is not L,
240 is not E|
VAADIGAGLADALTAPLDHKDKSLQSLTLDQXVRKNEKLKLAAQGAEKTYGNGDSLNTGKLKN
DKVSRFDFIRQIEVDGQLITLESGEFQIYKQDHSAVVALQIEKINNPDKIDSLINQRSFXVSG
LGGEHTAFNQLPDGKAEYHGKAFSSDDAGGKLTYTIDFAAKQGHGKIEHLKTPEQNVELAAAE
LKADEKSHAVILGDTRYGSEEKGTYHLALFGDRAQEIAGSATVKIGEKVHXIGIAGKQ >SEQ ID NO: 48 |mutant v3, Xaa 32 is any amino acid, 126 is not L,
243 is not E|
VAADIGTGLADALTAPLDHKDKGLKSLTLEDXIPQNGTLTLSAQGAEKTFKAGDKDNSLNTGK
LKNDKISREDEVQKIEVDGQTITLASGEFQIYKQNHSAVVALQIEKINNPDKTDSLINQRSFX
VSGLGGEHTAFNQLPGGKAEYHGKAFSSDDPNGRLHYSIDFTKKQGYGRIEHLKTLEQNVELA
AAELKADEKSHAVILGDTRYGSEEKGTYHLALFGDRAQEIAGSATVKIGEKVHXIGIAGKQ >SEQ ID NO: 49 |mutant v1, Xaa 34 is not R|
VAADIGAGLADALTAPLDHKDKGLQSLTLDQSVXKNEKLKLAAQGAEKTYGNGDSLNTGKLKN
DKVSRFDFIRQIEVDGQLITLESGEFQVYKQSHSALTAFQTEQIQDSEHSGKMVAKRQFRIGD
IAGEHTSFDKLPEGGRATYRGTAFGSDDAGGKLTYTIDFAAKQGNGKIEHLKSPELNVDLAAA
DIKPDGKRHAVISGSVLYNQAEKGSYSLGIFGGKAQEVAGSAEVKTVNGIRHIGLAAKQ >SEQ ID NO: 50 |mutant v2|
VAADIGAGLADALTAPLDHKDKSLQSLTLDQVVRKNEKLKLAAQGAEKTYGNGDSLNTGKLKN
DKVSRFDFIRQIEVDGQLITLESGEFQIYKQDHSAVVALQIEKINNPDKIDSLINQRSFRVSG
LGGEHTAFNQLPDGKAEYHGKAFSSDDAGGKLTYTIDFAAKQGHGKIEHLKTPEQNVELAAAE
LKADEKSHAVILGDTRYGSEEKGTYHLALFGDRAQEIAGSATVKIGEKVHAIGIAGKQ >SEQ ID NO: 51 |mutant v3|
VAADIGTGLADALTAPLDHKDKGLKSLTLEDVIPQNGTLTLSAQGAEKTFKAGDKDNSLNTGK
LKNDKISREDEVQKIEVDGQTITLASGEFQIYKQNHSAVVALQIEKINNPDKTDSLINQRSFR
VSGLGGEHTAFNQLPGGKAEYHGKAFSSDDPNGRLHYSIDFTKKQGYGRIEHLKTLEQNVELA
AAELKADEKSHAVILGDTRYGSEEKGTYHLALFGDRAQEIAGSATVKIGEKVHAIGIAGKQ >SEQ ID NO: 52 |R41S mutant v1|
VAADIGAGLADALTAPLDHKDKGLQSLTLDQSVSKNEKLKLAAQGAEKTYGNGDSLNTGKLKN
DKVSRFDFIRQIEVDGQLITLESGEFQVYKQSHSALTAFQTEQIQDSEHSGKMVAKRQFRIGD
IAGEHTSFDKLPEGGRATYRGTAFGSDDAGGKLTYTIDFAAKQGNGKIEHLKSPELNVDLAAA
DIKPDGKRHAVISGSVLYNQAEKGSYSLGIFGGKAQEVAGSAEVKTVNGIRHIGLAAKQ
```

SEQUENCE LISTING

```
>SEQ ID NO: 53 |mutant v2|
VAADIGAGLADALTAPLDHKDKSLQSLTLDQSVRKNEKLKLAAQGAEKTYGNGDSLNTGKLKN
DKVSRFDFIRQIEVDGQLITLESGEFQIYKQDHSAVVALQIEKINNPDKIDSLINQRSFRVSG
LGGEHTAFNQLPDGKAEYHGKAFSSDDAGGKLTYTIDFAAKQGHGKIEHLKTPEQNVELAAAE
LKADEKSHAVILGDTRYGSEEKGTYHLALFGDRAQEIAGSATVKIGEKVHAIGIAGKQ >SEQ ID NO: 54 |mutant v2|
VAADIGAGLADALTAPLDHKDKSLQSLTLDQSVRKNEKLKLAAQGAEKTYGNGDSLNTGKLKN
DKVSRFDFIRQIEVDGQLITLESGEFQIYKQDHSAVVALQIEKINNPDKIDSLINQRSFRVSG
LGGEHTAFNQLPDGKAEYHGKAFSSDDAGGKLTYTIDFAAKQGHGKIEHLKTPEQNVELAAAE
LKADEKSHAVILGDTRYGSEEKGTYHLALFGDRAQEIAGSATVKIGEKVHEIGIAGKQ >SEQ ID NO: 55 |mutant v3|
VAADIGTGLADALTAPLDHKDKGLKSLTLEDSIPQNGTLTLSAQGAEKTFKAGDKDNSLNTGK
LKNDKISREDEVQKIEVDGQTITLASGEFQIYKQNHSAVVALQIEKINNPDKTDSLINQRSFR
VSGLGGEHTAFNQLPGGKAEYHGKAFSSDDPNGRLHYSIDFTKKQGYGRIEHLKTLEQNVELA
AAELKADEKSHAVILGDTRYGSEEKGTYHLALFGDRAQEIAGSATVKIGEKVHAIGIAGKQ >SEQ ID NO: 56 |mutant v3|
VAADIGTGLADALTAPLDHKDKGLKSLTLEDSIPQNGTLTLSAQGAEKTFKAGDKDNSLNTGK
LKNDKISREDEVQKIEVDGQTITLASGEFQIYKQNHSAVVALQIEKINNPDKTDSLINQRSFR
VSGLGGEHTAFNQLPGGKAEYHGKAFSSDDPNGRLHYSIDFTKKQGYGRIEHLKTLEQNVELA
AAELKADEKSHAVILGDTRYGSEEKGTYHLALFGDRAQEIAGSATVKIGEKVHEIGIAGKQ >SEQ ID NO: 57 |mutant v3, where residue 32 is any amino except S,
residue 126 is not L, residue 243 is not E|
VAADIGTGLA DALTAPLDHK DKGLKSLTLE DXIPQNGTLT LSAQGAEKTF KAGDKDNSLN
TGKLKNDKIS RFDFVQKIEV DGQTITLASG EFQIYKQNHS AVVALQIEKI NNPDKTDSLI
NQRSFXVSGL GGEHTAFNQL PGGKAEYHGK AFSSDDPNGR LHYSIDFTKK QGYGRIEHLK
TLEQNVELAA AELKADEKSH AVILGDTRYG SEEKGTYHLA LFGDRAQEIA GSATVKIGEK
VHXIGIAGKQ                                                      -250
```

The invention claimed is:

1. A polypeptide comprising an amino acid sequence having at least 95% sequence identity to SEQ ID NO: 5, wherein the amino acid sequence differs from SEQ ID NO: 5 by S32V, L123R, and E240A substitutions numbered relative to SEQ ID NO: 5.

2. The polypeptide of claim 1, wherein the amino acid sequence comprises SEQ ID NO: 50.

3. An immunogenic composition comprising a pharmaceutically acceptable carrier, a polypeptide according to claim 1, and optionally an adjuvant.

* * * * *